(12) United States Patent
Curiel et al.

(10) Patent No.: US 12,404,332 B2
(45) Date of Patent: Sep. 2, 2025

(54) METHODS FOR DIAGNOSING AND TREATING CANCERS

(71) Applicant: Research Development Foundation, Carson City, NV (US)

(72) Inventors: Tyler J. Curiel, San Antonio, TX (US); Anand Kornepati, San Antonio, TX (US)

(73) Assignee: Research Development Foundation, Carson City, NV (US)

(*) Notice: Subject to any disclaimer, the term of this patent is extended or adjusted under 35 U.S.C. 154(b) by 438 days.

(21) Appl. No.: 17/200,729

(22) Filed: Mar. 12, 2021

(65) Prior Publication Data

US 2021/0332136 A1 Oct. 28, 2021

Related U.S. Application Data

(60) Provisional application No. 63/000,187, filed on Mar. 26, 2020, provisional application No. 62/989,164, filed on Mar. 13, 2020.

(51) Int. Cl.

| | |
|---|---|
| *C07K 16/28* | (2006.01) |
| *A61K 31/196* | (2006.01) |
| *A61K 31/437* | (2006.01) |
| *A61K 31/519* | (2006.01) |
| *A61K 31/5377* | (2006.01) |
| *A61K 31/675* | (2006.01) |
| *A61K 39/00* | (2006.01) |
| *A61K 45/06* | (2006.01) |
| *A61P 35/00* | (2006.01) |
| *G01N 33/68* | (2006.01) |

(52) U.S. Cl.
CPC ........ *C07K 16/2827* (2013.01); *A61K 31/196* (2013.01); *A61K 31/437* (2013.01); *A61K 31/519* (2013.01); *A61K 31/5377* (2013.01); *A61K 31/675* (2013.01); *A61K 45/06* (2013.01); *A61P 35/00* (2018.01); *C07K 16/2818* (2013.01); *G01N 33/68* (2013.01); *A61K 2039/505* (2013.01); *G01N 2333/4703* (2013.01); *G01N 2800/7028* (2013.01)

(58) Field of Classification Search
CPC ..... C07K 16/2827; A61P 35/00; G01N 33/68; G01N 2800/7028; A61K 2039/505; C12N 15/1138; C12Q 1/6886; C12Q 2600/158
See application file for complete search history.

(56) References Cited

U.S. PATENT DOCUMENTS

| 4,636,505 A | 1/1987 | Tucker | |
|---|---|---|---|
| 5,869,467 A | 2/1999 | Holy et al. | |
| 8,779,105 B2 * | 7/2014 | Korman | C07K 16/18 |
| | | | 530/388.1 |
| 2003/0082229 A1 * | 5/2003 | Anderson | A61K 47/10 |
| | | | 514/567 |
| 2009/0143357 A1 * | 6/2009 | Diaz | A61P 35/04 |
| | | | 514/227.8 |
| 2019/0054090 A1 | 2/2019 | Venkataraman et al. | |

FOREIGN PATENT DOCUMENTS

| WO | WO-9502603 A2 * | 1/1995 | ........... A61K 31/545 |
|---|---|---|---|
| WO | WO-2015061668 A1 * | 4/2015 | ......... C07K 16/2827 |

OTHER PUBLICATIONS

Brandsma et al Expert Opinion on Investigational Drugs vol. 26 p. 1341 (2017) (Year: 2017).*
Qu et al Cellular Physiology and Biochemistry vol. 43 p. 1893 (2017), (Year: 2017).*
Sen et al AACR p. 647-661 (May 2019). (Year: 2019).*
Wu et al Frontiers in Immunology vol. 10 p. 1 (Aug. 2019) (Year: 2019).*
Stella et al, Urologic Oncology: Seminars and Original Investigations vol. 28 p. 260 (2010) (Year: 2010).*
Hau et al Urologic Oncology: Seminars and Original Investigations vol. 35 p. 593 (2017) (Year: 2017).*
Rose et al Journal of the National Cancer Institute vol. 82 p. 510 (1990) (Year: 1990).*
Burr, M. L. et al., "CMTM6 maintains the expression of PD-L1 and regulates anti-tumour immunity," *Nature*, 549.7670 (2017): 101-105.
Cao, D. et al., "Retinoic Acid-Related Orphan Receptor C Regulates Proliferation, Glycolysis, and Chemoresistance via the PD-L1/ITGB6/STAT3 Signaling Axis in Bladder Cancer," *Molecular Cell Biology*, 79.10 (2019): 2604-2618.
Caulfield, S. E. et al., "Olaparib: A Novel Therapy for Metastatic Breast Cancer in Patients with BRCA1/2 Mutation," *J Adv Pract Oncol*, 10.2 (2019): 167-174.
Chang, C-H. et al., "Metabolic competition in the tumor microenvironment is a driver of cancer progression" *Cell*, 162 (2015): 1229-1241.
Clark, C. A. et al., "Tumor-intrinsic PD-L1 signals regulate cell growth, pathogenesis and autophagy in ovarian cancer and melanoma," *Cancer Res* 76.23 (2016): 6964-6974.
Ding, L. et al., "PARP Inhibition Elicits STING-Dependent Antitumor Immunity in Brca1-Deficient Ovarian Cancer," *Cell Reports*, 25 (2018): 2972-2980.
Dong, H. et al., "B7-H1, a third member of the B7 family, co-stimulates T-cell proliferation and interleukin-10 secretion," *Nat Med.*, 5.12 (1999): 1365-1369.
Escors, D. et al., "The intracellular signalosome of PD-L1 in cancer cells," *Signal Transduction and Targeted Therapy*, 3.26 (2018): 1-9.
Filipek, P. A. et al., "LAMTOR/Ragulator is a negative regulator of Arl8band BORC-dependent late endosomal positioning," *J Cell Biol*, 216.12 (2017): 4199-4215.

(Continued)

Primary Examiner — Sheela J. Huff
(74) Attorney, Agent, or Firm — Parker Highlander PLLC

(57) ABSTRACT

Provided herein are methods for the diagnosis, assessment, and treatment of cancer. In some aspects, detection of intracellular or cytoplasmic PD-L1, or measuring the ratio of cytoplasmic to surface PD-L1, can be used to identify cancers that may respond to immunotherapies or a DDR inhibitor such as, e.g., a Chk1 inhibitor, a PARP inhibitor, an ATM inhibitor, or an ATR inhibitor.

48 Claims, 72 Drawing Sheets
(49 of 72 Drawing Sheet(s) Filed in Color)
Specification includes a Sequence Listing.

(56) References Cited

OTHER PUBLICATIONS

Fong, P. C. et al., "Inhibition of Poly(ADP-Ribose) Polymerase in Tumors from BRCA Mutation Carriers," *The New England Journal of Medicine*, 361.2 (2009): 123-134.

Gao, Y. et al., "Acetylation-dependent regulation of PD-L1 nuclear translocation dictates the efficacy of anti-PD-1 immunotherapy," *Nat Cell Biol*, 22.9 (2020): 1064-1075.

Gato-Canas, M. et al., "PDL1 Signals through Conserved Sequence Motifs to Overcome Interferon-Mediated Cytotoxicity," *Cell Reports*, 20 (2017): 1818-1829.

Ghebeh, H. et al., "Doxorubicin downregulates cell surface B7-H1 expression and upregulates its nuclear expression in breast cancer cells: role of B7-H1 as an anti-apoptotic molecule," *Breast Cancer Research*, 12 (2010): 1-12.

Gupta, H. B. et al., "Tumor cell-intrinsic PD-L1 promotes tumor-initiating cell generation and functions in melanoma and ovarian cancer," *Signal Transduction and Targeted Therapy*, 1 (2016): 1-9.

He, X-h. et al., "Identification of a novel splice variant of human PD-LI mRNA encoding an isoform-lacking Igv-like domain," *Acta Pharmacologica Sinica*, 26.4 (2005): 462-468.

Hennessey, R. C., "Ultraviolet radiation accelerates NR as-mutant melanomagenesis: A cooperative effect blocked by sunscreen," *Pigment Cell Melanoma Res.*, 30.5 (2017): 477-487.

Hou, J. et al., "PD-L1-Mediated Gasdermin C Expression Switches Apoptosis to Pyroptosis in Cancer Cells and Facilitates Tumor Necrosis," *Nat Cell Biol*, 22.10 (2020): 1264-1275.

Kleffel, S. et al., "Melanoma Cell-Intrinsic PD-1 Receptor Functions Promote Tumor Growth," *Cell*, 162 (2015): 1242-1256.

Lee, E. K. et al., "Combined PARP and Immune Checkpoint Inhibition in Ovarian Cancer," *Trends in Cancer*, 5.9 (2019): 524-528.

Messing, E. M. et al., "Effect of Intravesical Instillation of Gemcitabine vs Saline Immediately Following Resection of Suspected Low-Grade Non-Muscle-Invasive Bladder Cancer on Tumor Recurrence SWOG S0337 Randomized Clinical Trial," *JAMA*, 319 (2018): 1880-1888.

Mezzadra, R. et al., "Identification of CMTM6 and CMTM4 as PD-L1 protein regulators," *Nature*, 549.7670 (2017): 106-110.

Overbye. A. et al., "Identification of prostate cancer biomarkers in urinary exosomes," *Oncotarget*, 6.30 (2015): 30357-30376.

Pantelidou, C. et al., "PARP inhibitor efficacy depends on CD8+ T cell recruitment via intratumoral STING pathway activation in BRCA-deficient models of triple-negative breast cancer," *Cancer Discov.*, 9.6 (2019): 722-737.

PCT International Search Report and Written Opinion issued in International Patent Application No. PCT/US2021/022244, dated Jun. 25, 2021.

Pilié. P. G. et al., "State-of-the-art strategies for targeting the DNA damage response in cancer," *Nat Rev Clin Oncol.*, 16.2 (2018): 81-104.

Qu, Q-X. et al., "Membranous and Cytoplasmic Expression of PD-L1 in Ovarian Cancer Cells," *Cell Physiol Biochem*, 43 (2017): 1893-1906.

Sancak, Y. et al., "Ragulator-RagComplex Targets mTORC1 to the Lysosomal Surface and Is Necessary for Its Activation by Amino Acids," *Cell*, 141 (2010): 290-303.

Sen, T. et al., "Targeting DNA Damage Response Promotes Anti-tumor Immunity through STING-Mediated T-cell Activation in Small Cell Lung Cancer," *Cancer Discovery*, 9 (2019): 646-661.

Topalian, S. L. et al., "Targeting the PD-1/B7-H1(PD-L1) pathway to activate anti-tumor Immunity," *Curr Opin Immunol.*, 24.2 (2012): 207-212.

Tu, X. et al., "PD-L1 (B7-H1) competes with the RNA exosome to regulate the DNA damage response and can be targeted to sensitize to radiation or chemotherapy," *Mol Cell*, 74.6 (2019): 1215-1226.

Wang, L. et al., "Inhibition of the ATM/Chk2 axis promotes cGAS/STING signaling in ARID1A-deficient tumors," *The Journal of Clinical Investigation*, 130.11 (2020): 5951-5966.

Wang, X. et al., "PD-L1 expression in human cancers and its association with clinical outcomes," *Onco Targets and Therapy*, 9 (2016): 5023-5039.

Wang, X. et al., "Tumor cell-intrinsic PD-1 receptor is a tumor suppressor and mediates resistance to PD-1 blockade therapy," *PNAS*, 117.12 (2020): 6640-6650.

Wu, X. et al., "B7-H1(PD-L1) confers chemoresistance through ERK and p38 MAPK pathway in tumor cells," *BioRxiv*, 308601 (2018): 1-26.

Wu, X. et al., "Targeting B7-H1 (PD-L1) sensitizes cancer cells to chemotherapy," *Heliyon*, 4 (2018): 1-24.

Wu, Y. et al., "PD-L1 Distribution and Perspective for Cancer Immunotherapy—Blockade, Knockdown, or Inhibition," *Frontiers in Immunology*, 10 (2019): 1-15.

Zhang, D. et al., "Association between Body Mass Index and Immune-Related Adverse Events (irAEs) among Advanced-Stage Cancer Patients Receiving Immune Checkpoint Inhibitors: A Pan-Cancer Analysis," *Cancers*, 13 (2021): 1-12.

Zhang, J. et al., "Biochemical Aspects of PD-L1 Regulation in Cancer Immunotherapy," *Trends Biochem Sci.*, 43.12 (2018): 1014-1032.

Abaza et al., "Programmed Cell Death Protein 1 (PD-1) and Programmed Cell Death Ligand 1 (PD-L1) Immunotherapy: A promising Breakthrough in Cancer Therapeutics", *Cureus*, 15(():e44582, 2023.

Carlsen et al., "Anti-cancer immune responses to DNA damage response inhibitors: Molecular mechanisms and progress toward clinical translation", *Frontiers in Oncology*, 12:998388, 2022.

Elkamhawy et al., "The Journey of DDR1 and DD$2 Kinase Inhibitors as Rising Stars in the Fight against Cancer", *Molecular Sciences*, 22, 6535, 2021.

Huang et al., "DNA damage response signaling pathways and targets for radiotherapy sensitization in cancer", *Signal Transduction and Targeted Therapy*, 5:60, 2020.

Minchom et al., "Dancing with the DNA damage response: next-generation anti-cancer therapeutic strategies", *Therapeutic Advances in Medical Oncology*, 10:1-18, 2018.

Neizer-Ashun et al. "Reality CHEK: Understanding the biology and clinical potential of CHK1", *Cancer Letters*, 497, 202-211, 2021.

O'Malley et al., "PARP Inhibitors in Ovarian Cancer: A Review", *Targeted Oncology*, 18:471-503, 2023.

Peng et al., "A narrative review of immune checkpoint mechansims and current immune checkpoint therapy", *Ann Blood*, 7:33, 2022.

Sun et al., "Immune checkpoint therapy for solid tumours: clinical dilemmas and future trends", *Signal Transduction an Targeted Therapy*, 8:320, 2023.

Wojtukiewica et al., "Inhibitors of immune checkpoints—PD-1, PD-L1, CTLA-4-new opportunities of cancer patients and a new challenge for internists and general practitioners", *Cancer and Metastasis Reviews*, 40:949-982, 2021.

Yano et al., "Emerging strategies for cancer therapy by ATR inhibitors", *Cancer Science*, 114:2709-2721, 2023.

\* cited by examiner

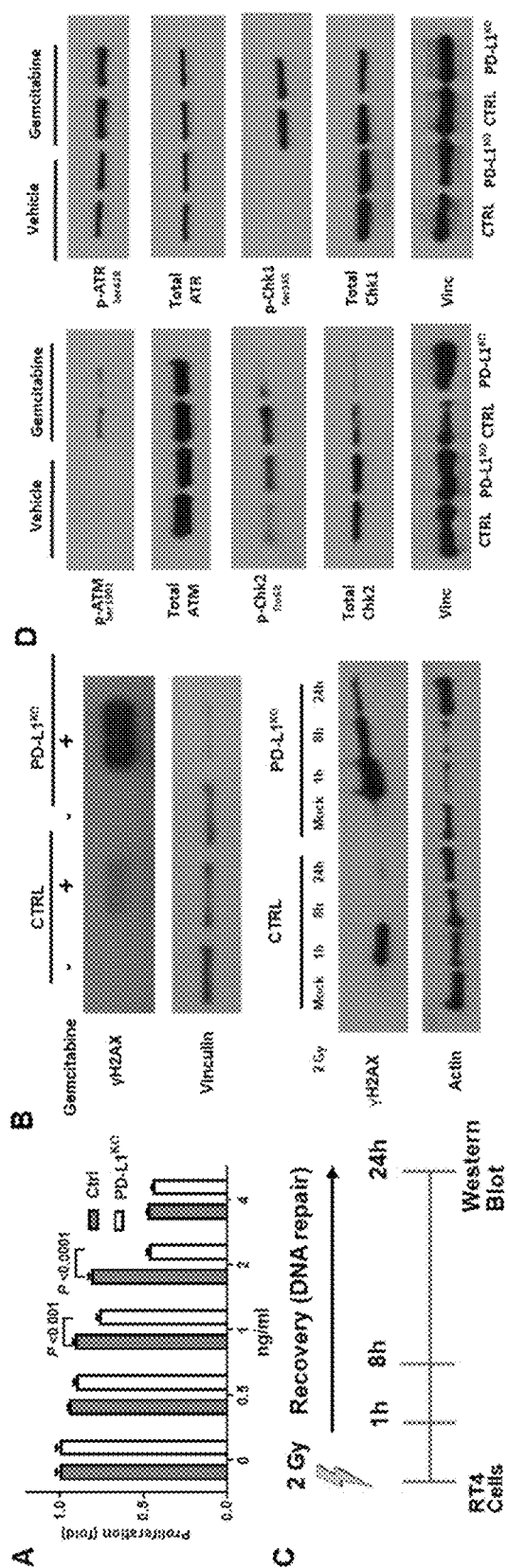
FIG. 1A-D

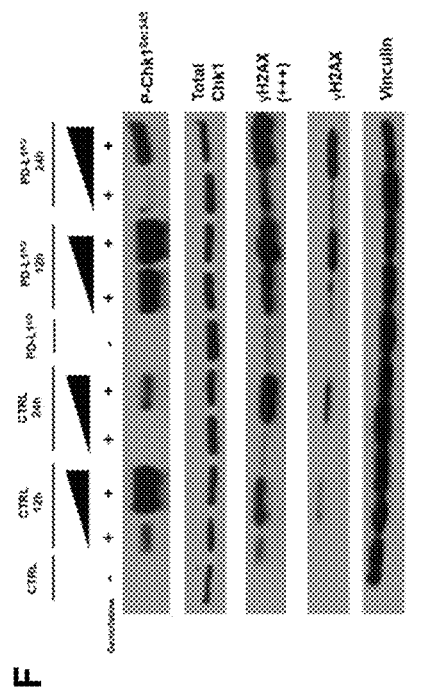
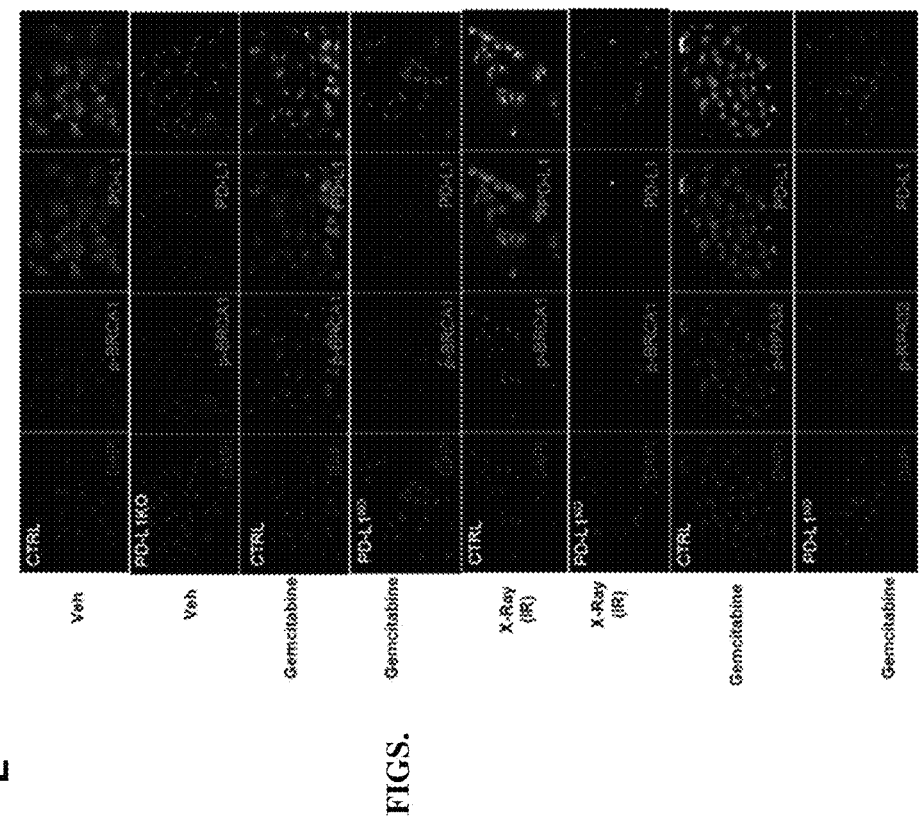
FIGS. 1E-F

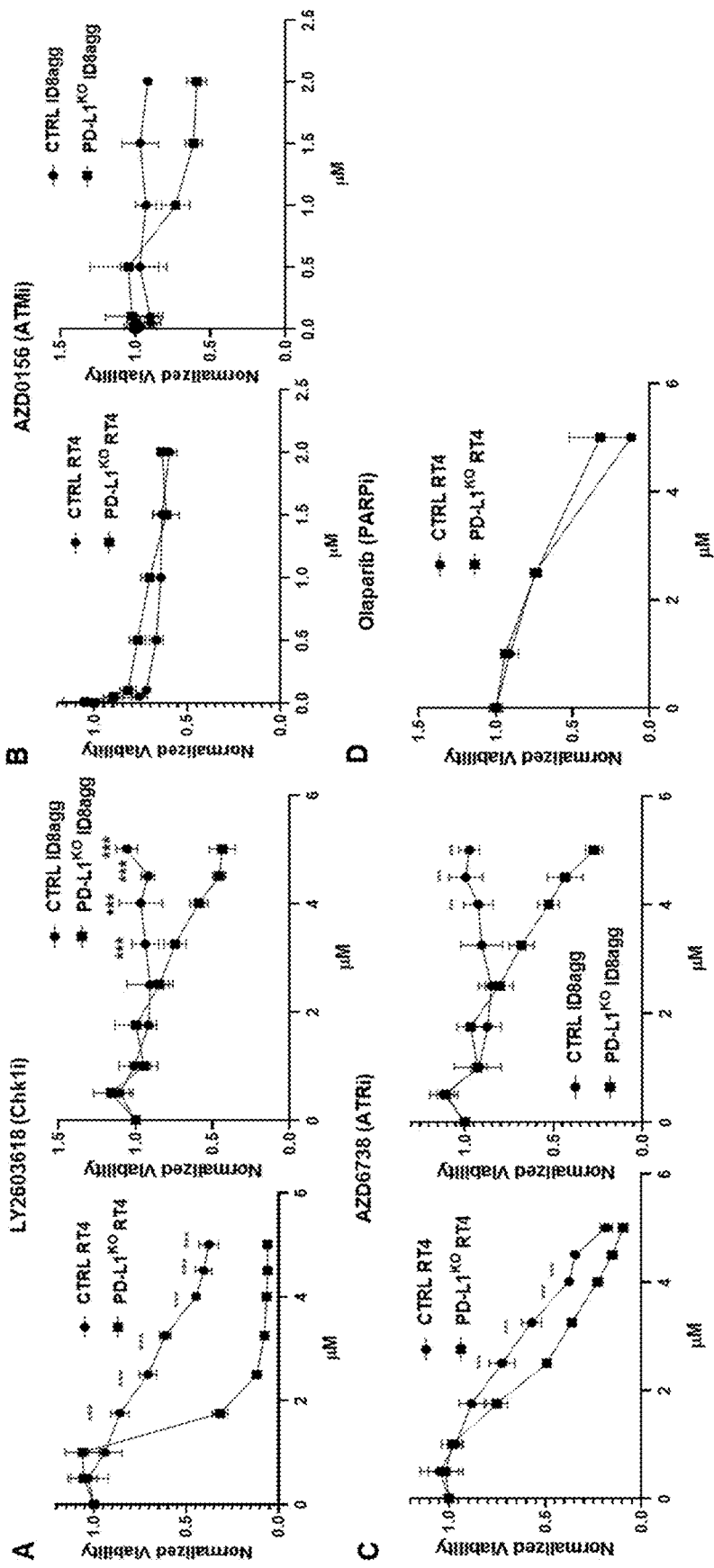
FIGS. 2A-D

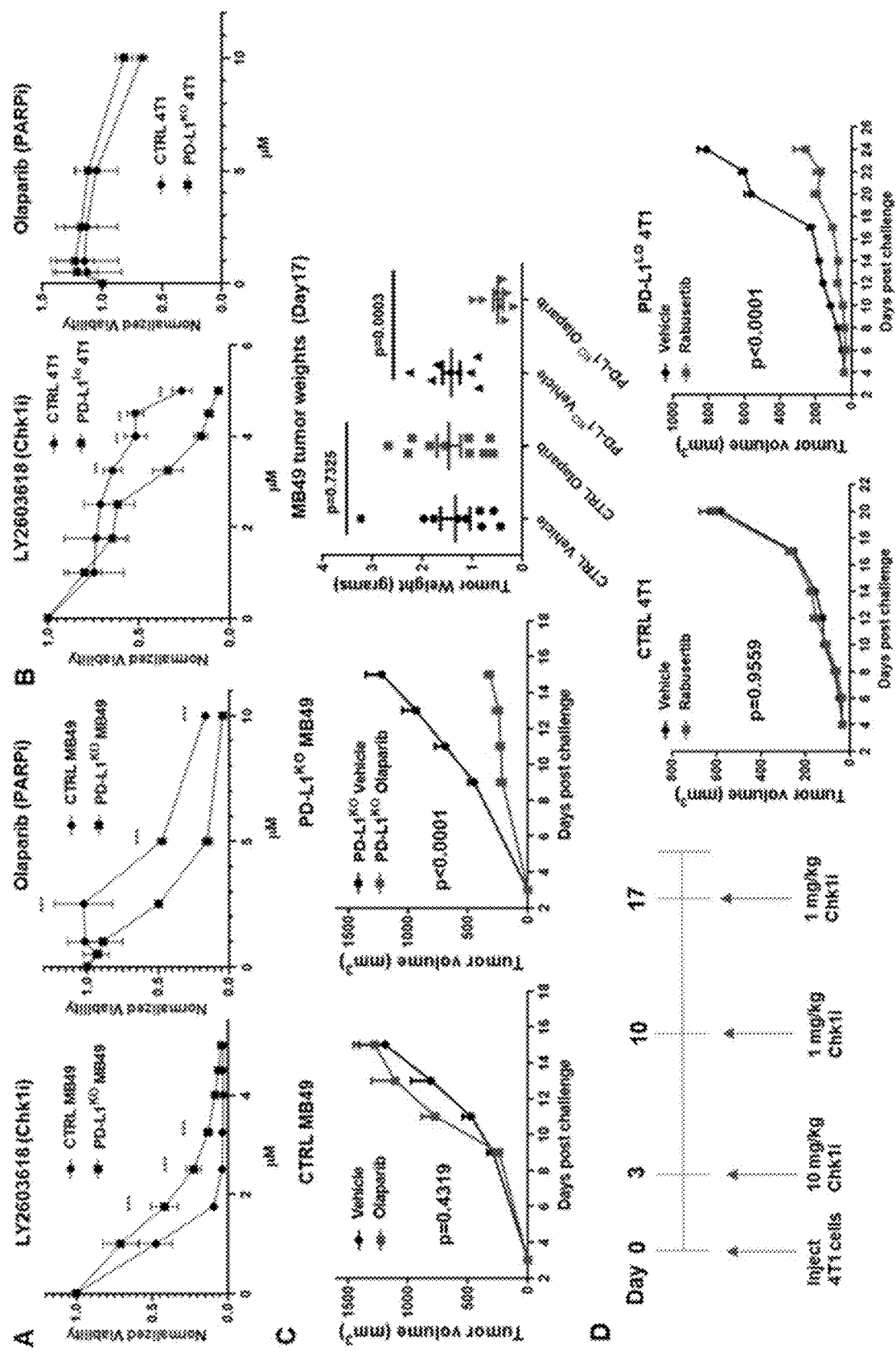
FIGS. 3A-D

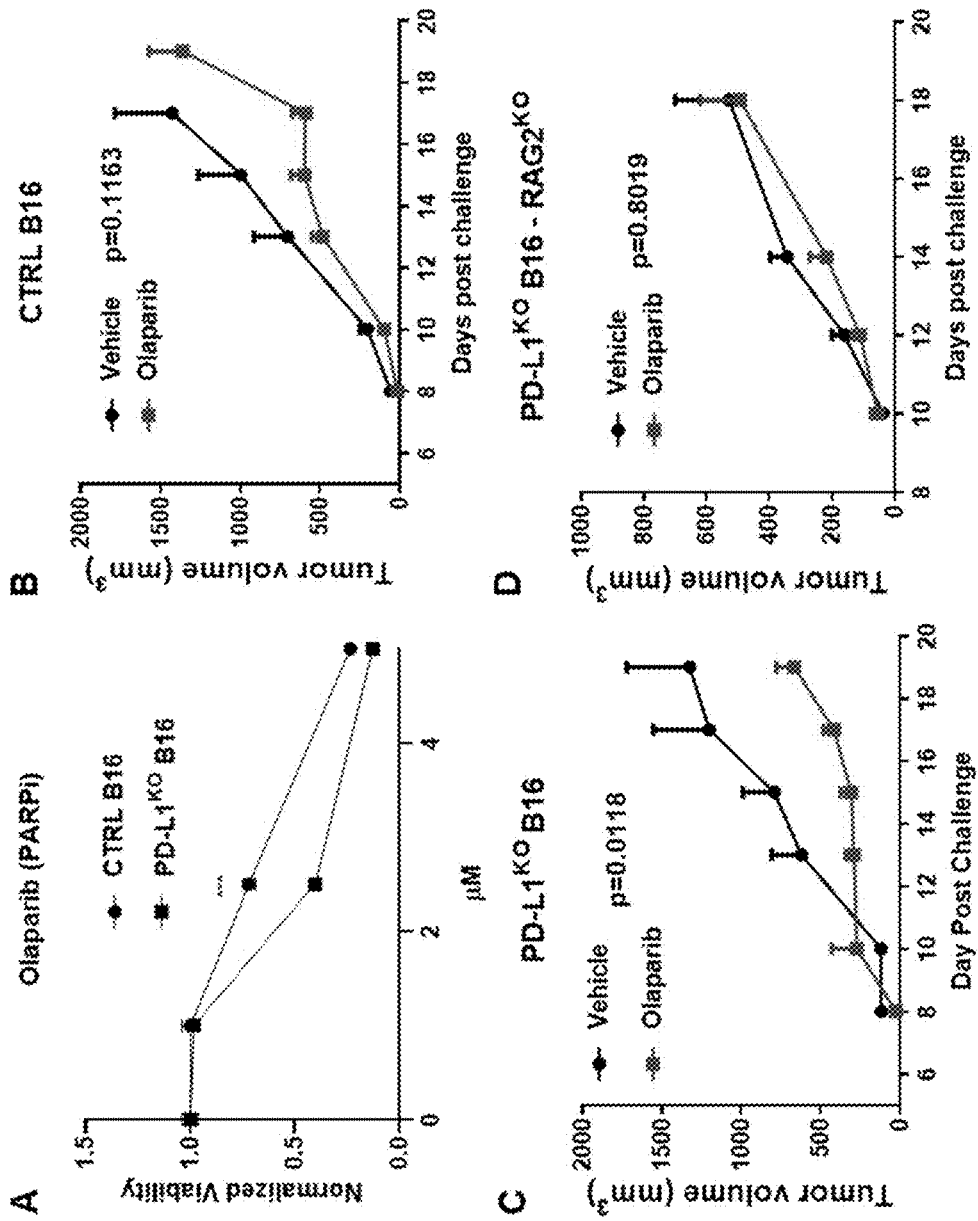
FIGS. 4A-D

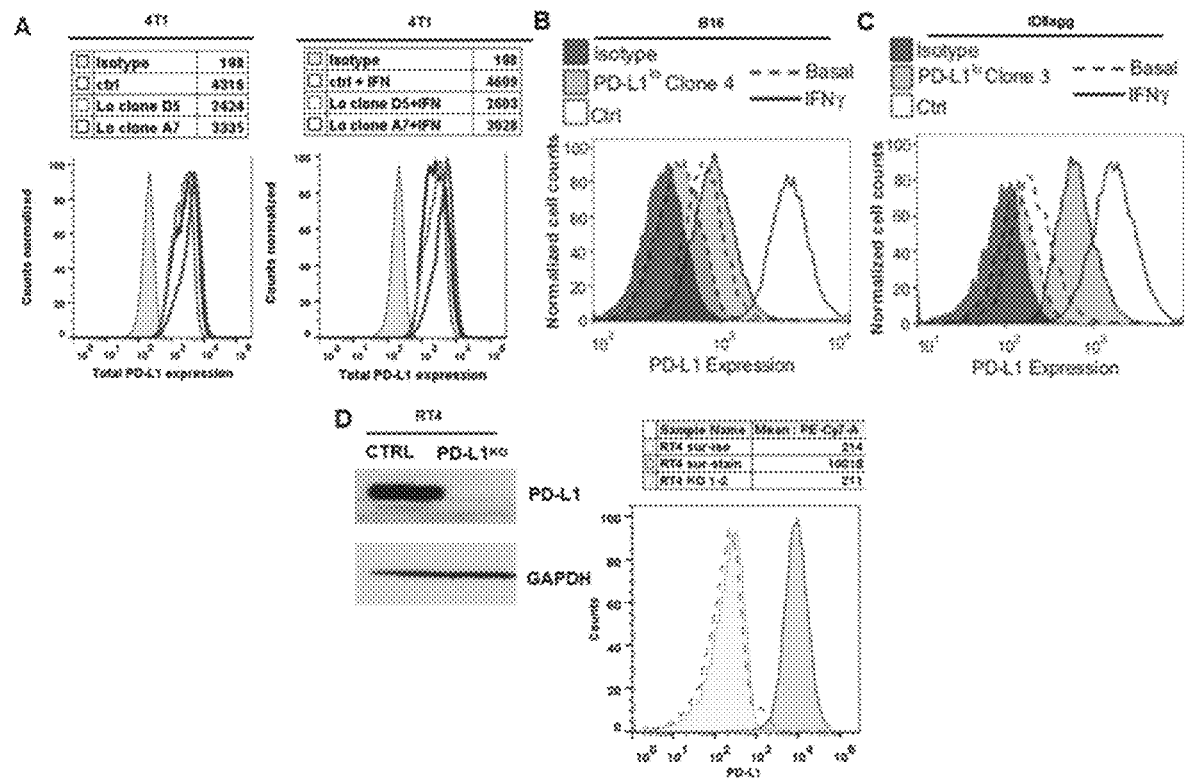
FIGS. 5A-D

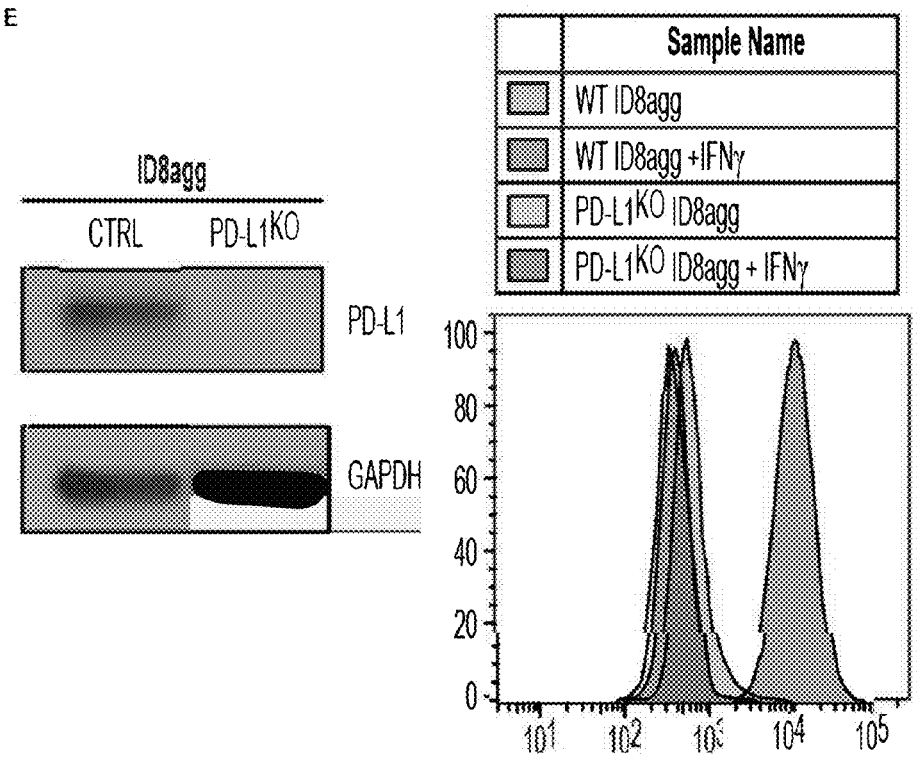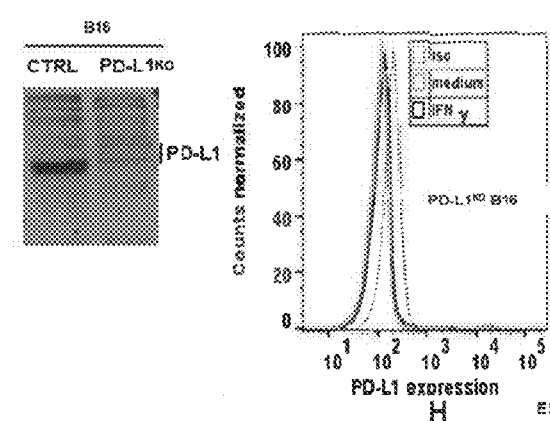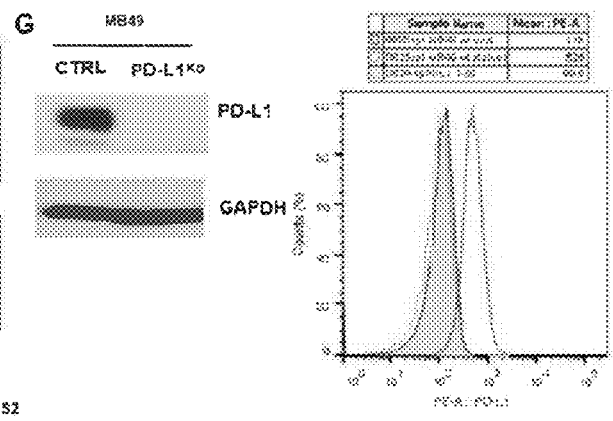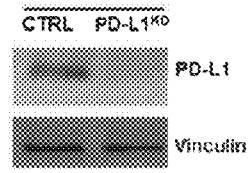
FIGS. 5E-H

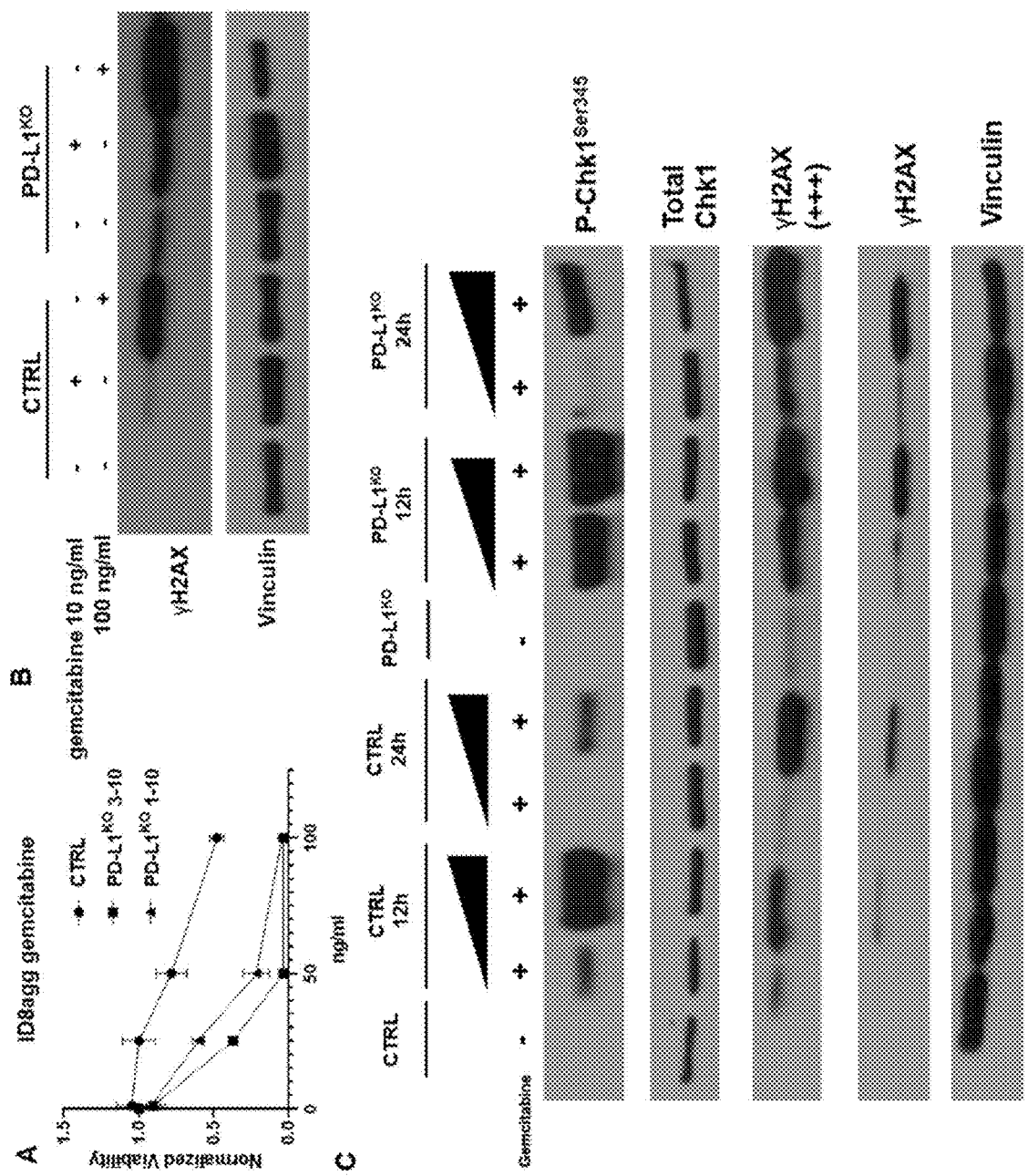
FIGS. 6A-C

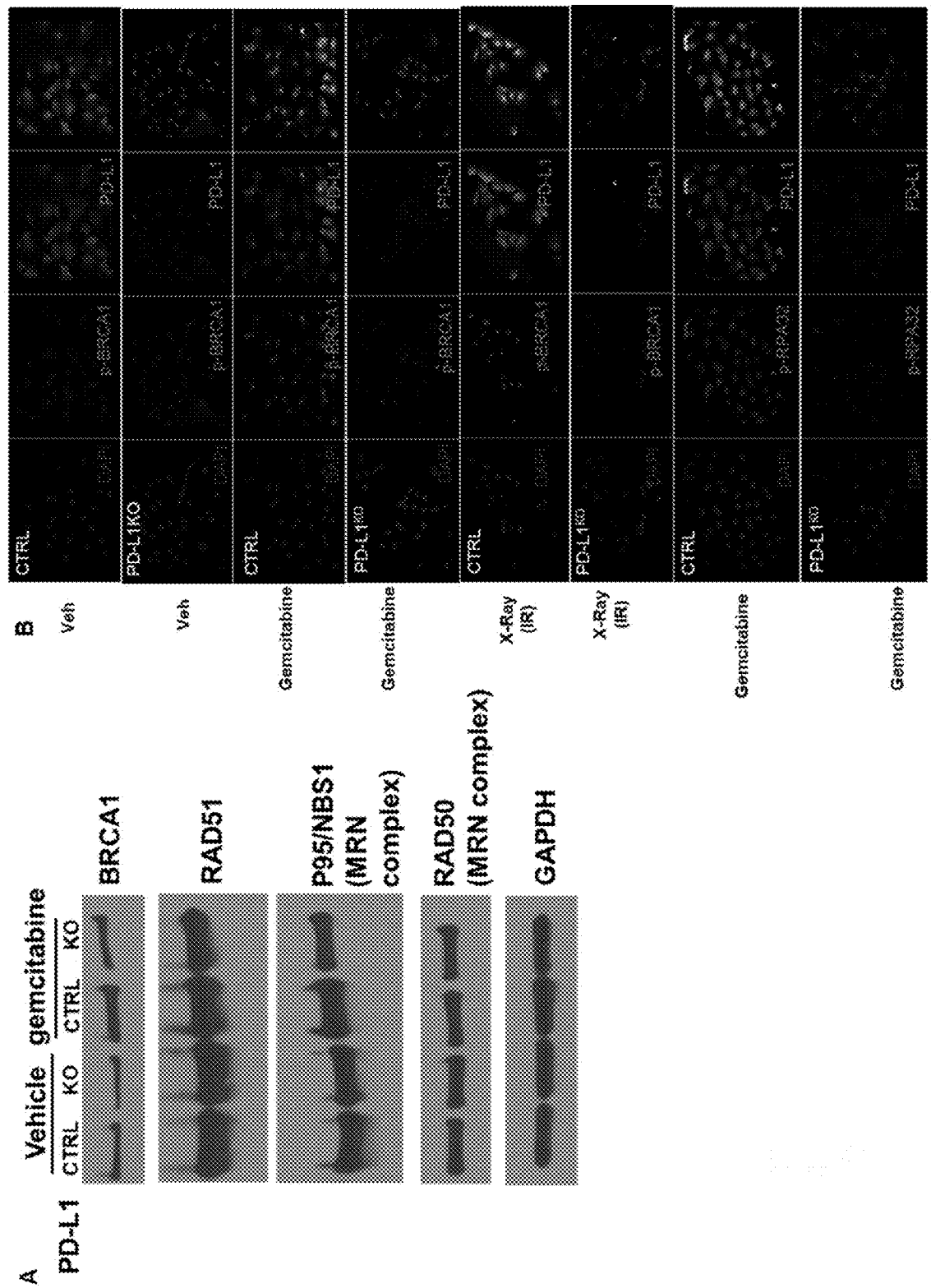
FIGS. 7A-B

FIG. 8F
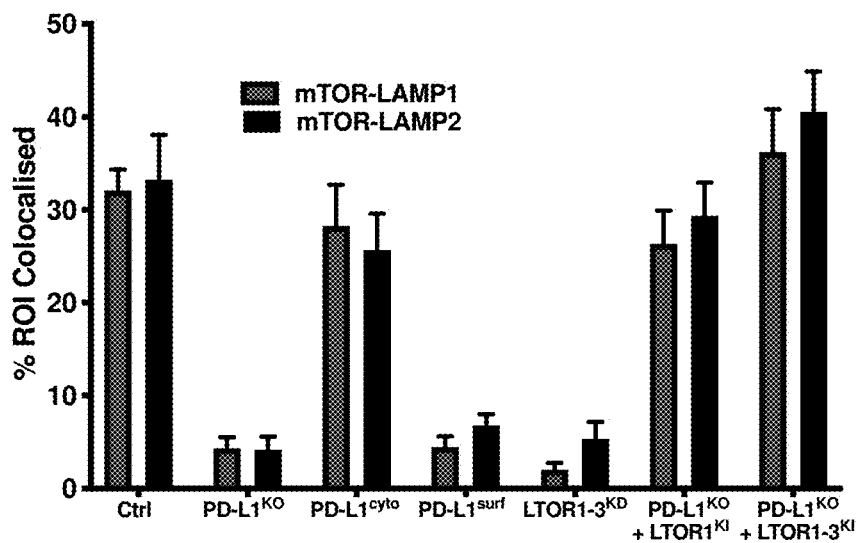
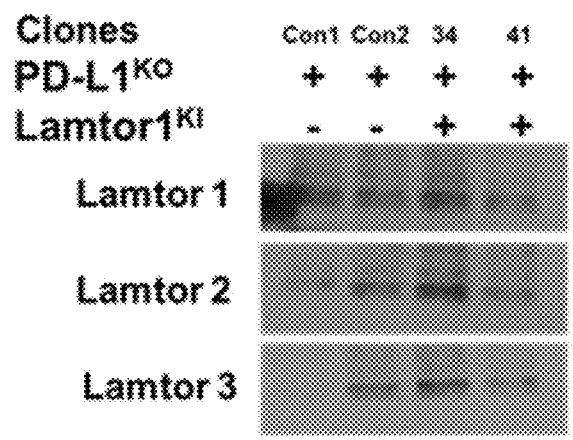

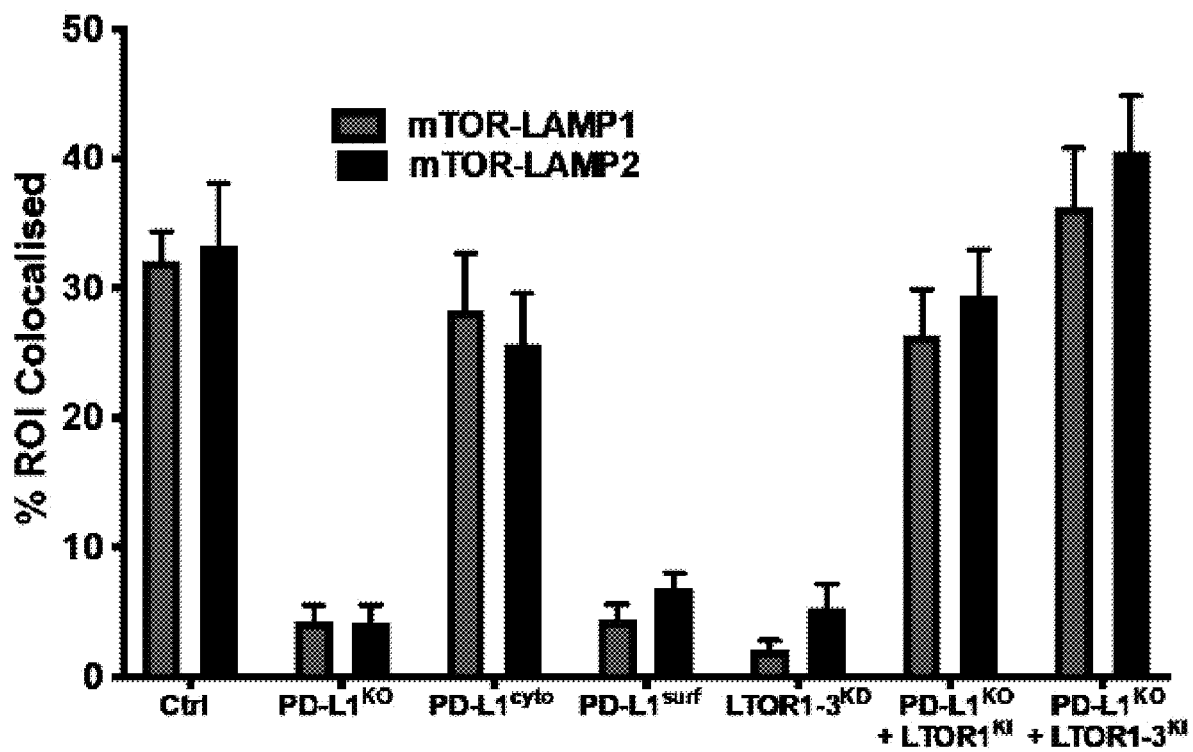
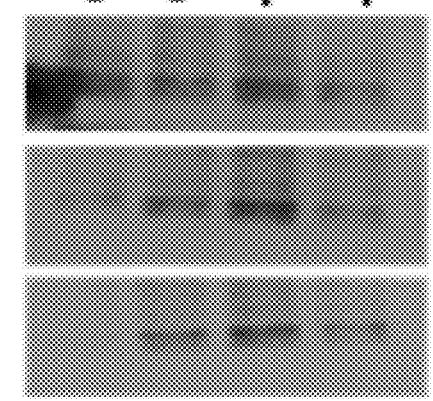
FIG. 8F (continued)

PD-L1<sup>tot</sup>   PD-L1<sup>surf</sup>   PD-L1<sup>cyto</sup>

FIG. 12A
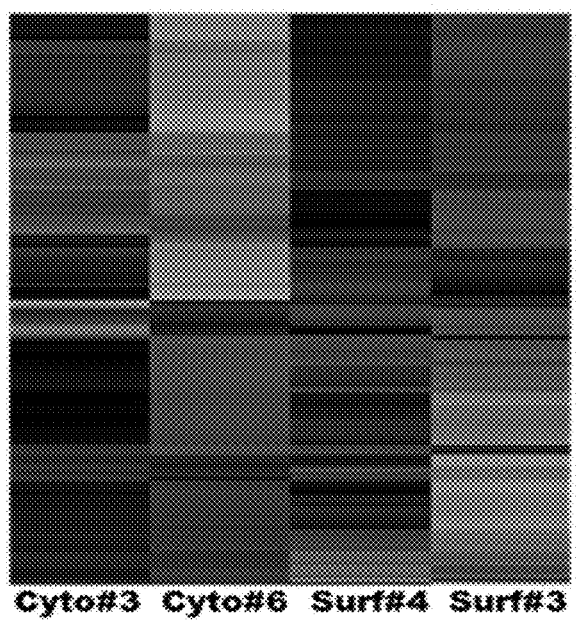
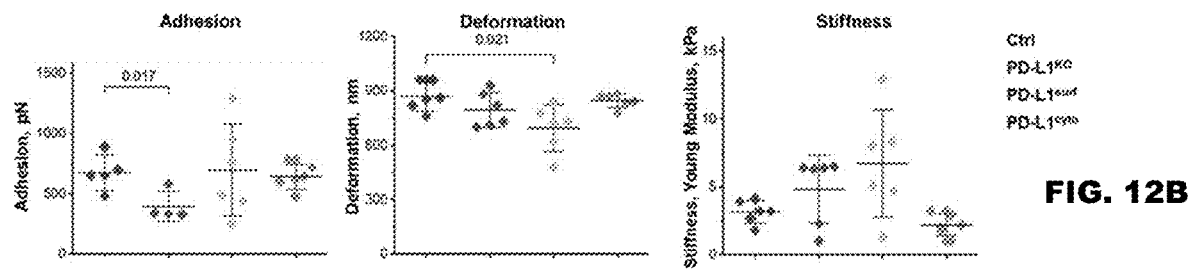
FIG. 12B

FIG. 15
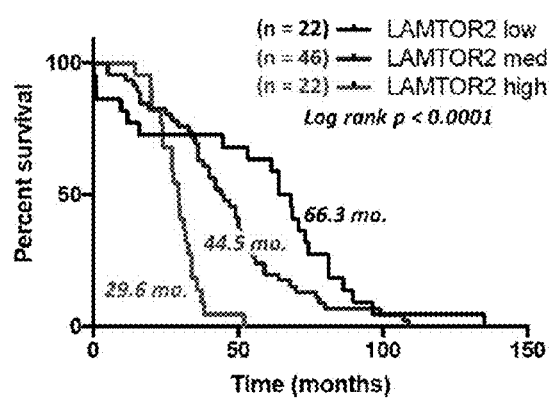
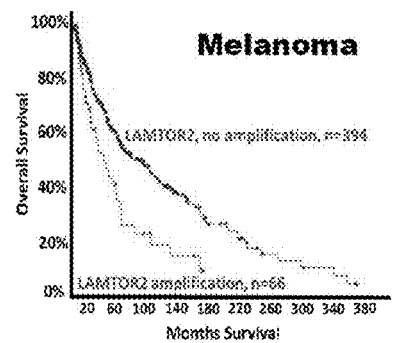
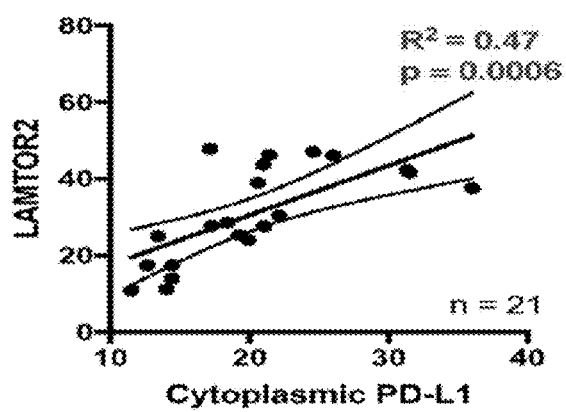
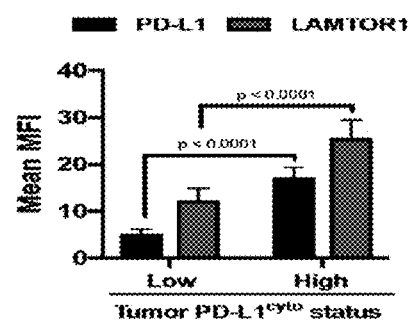

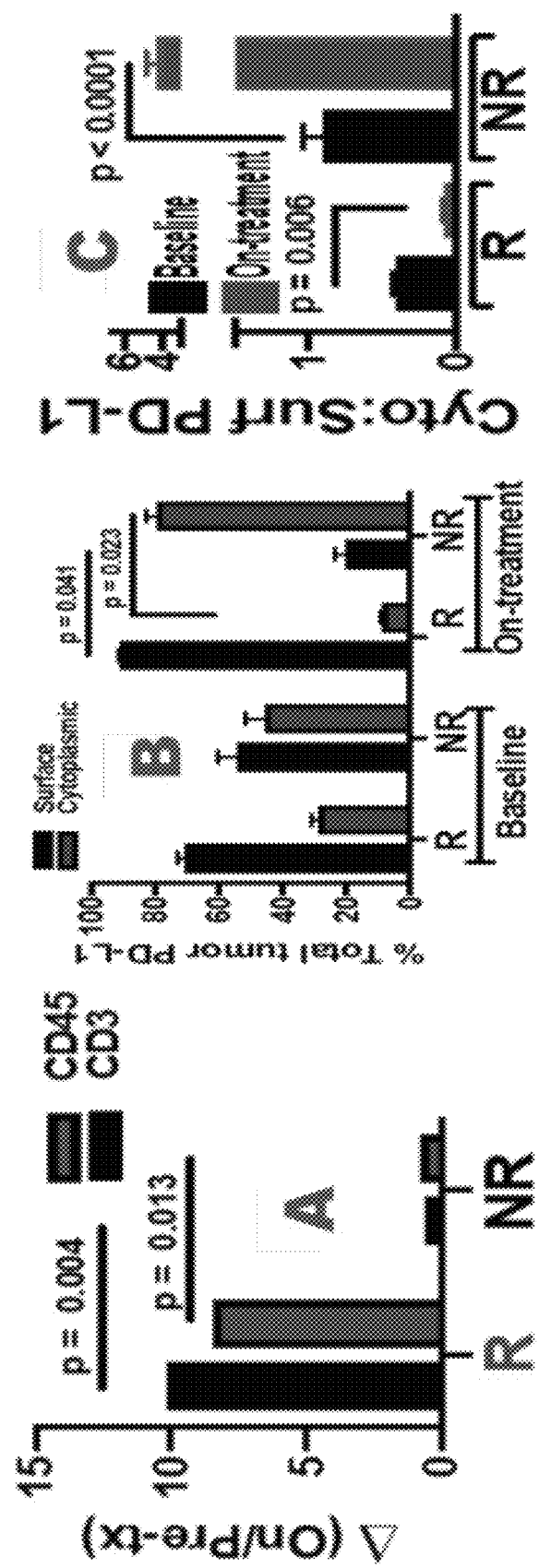
FIGS. 19A-C

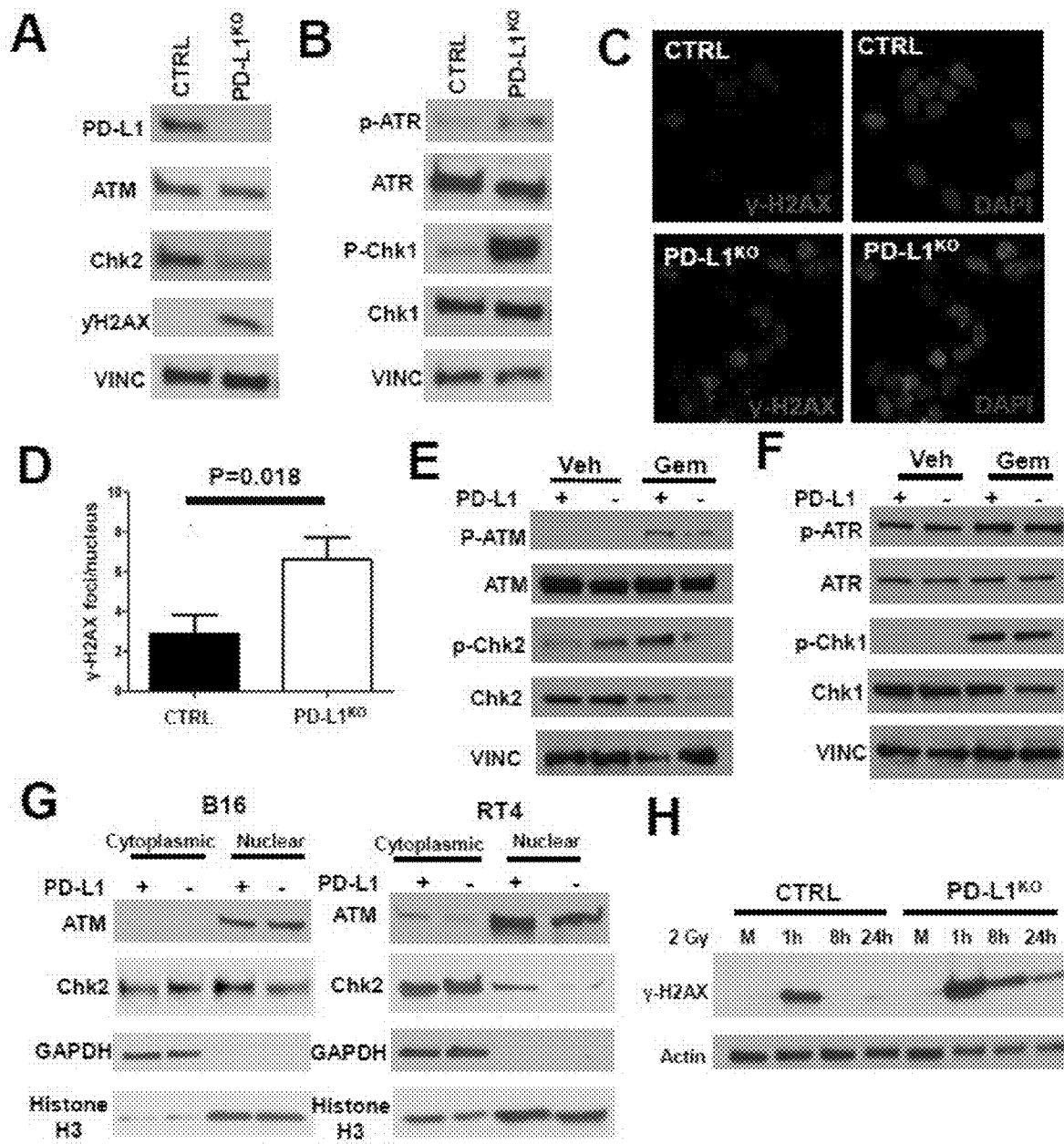
FIGS. 21A-H

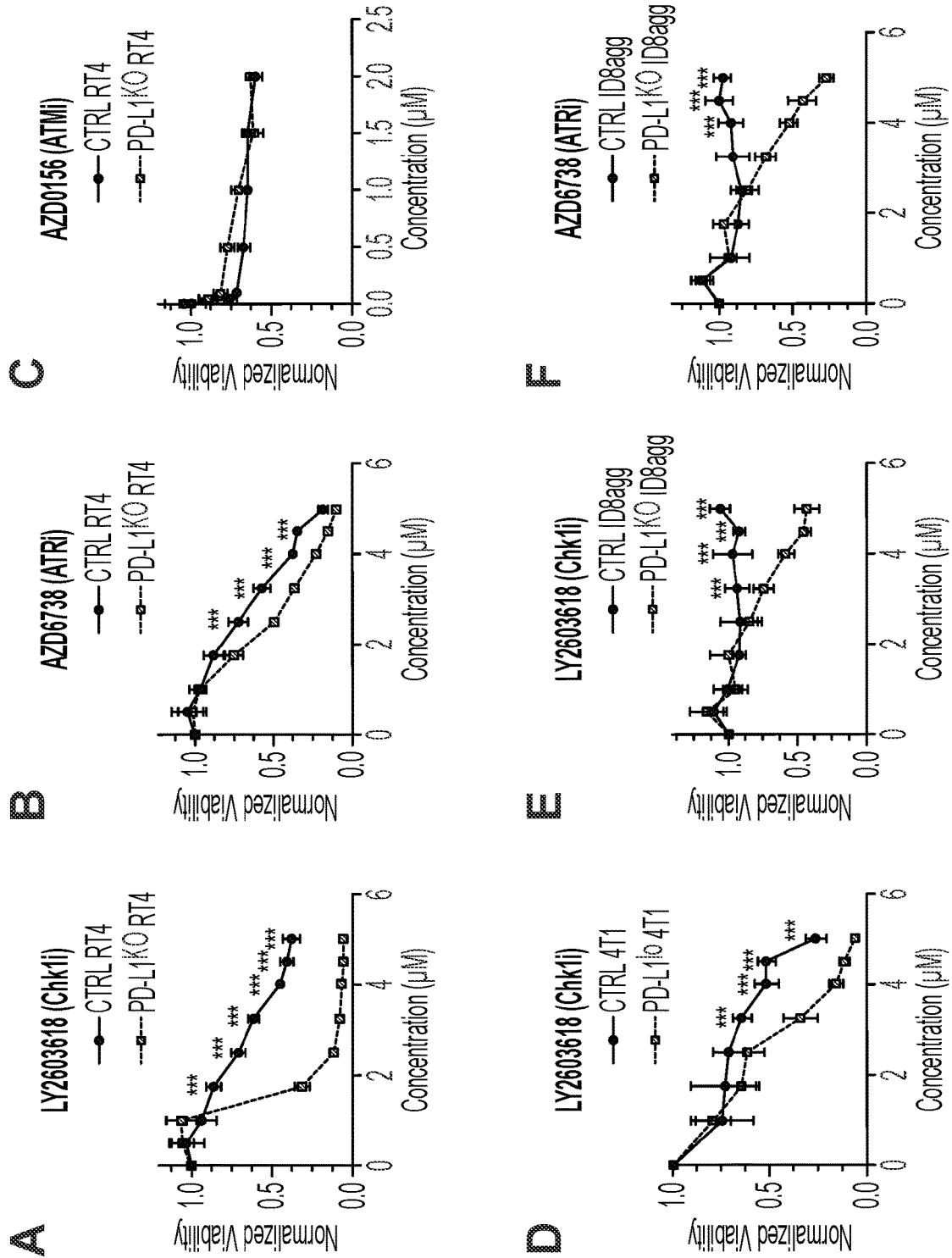
FIG. 22A-F

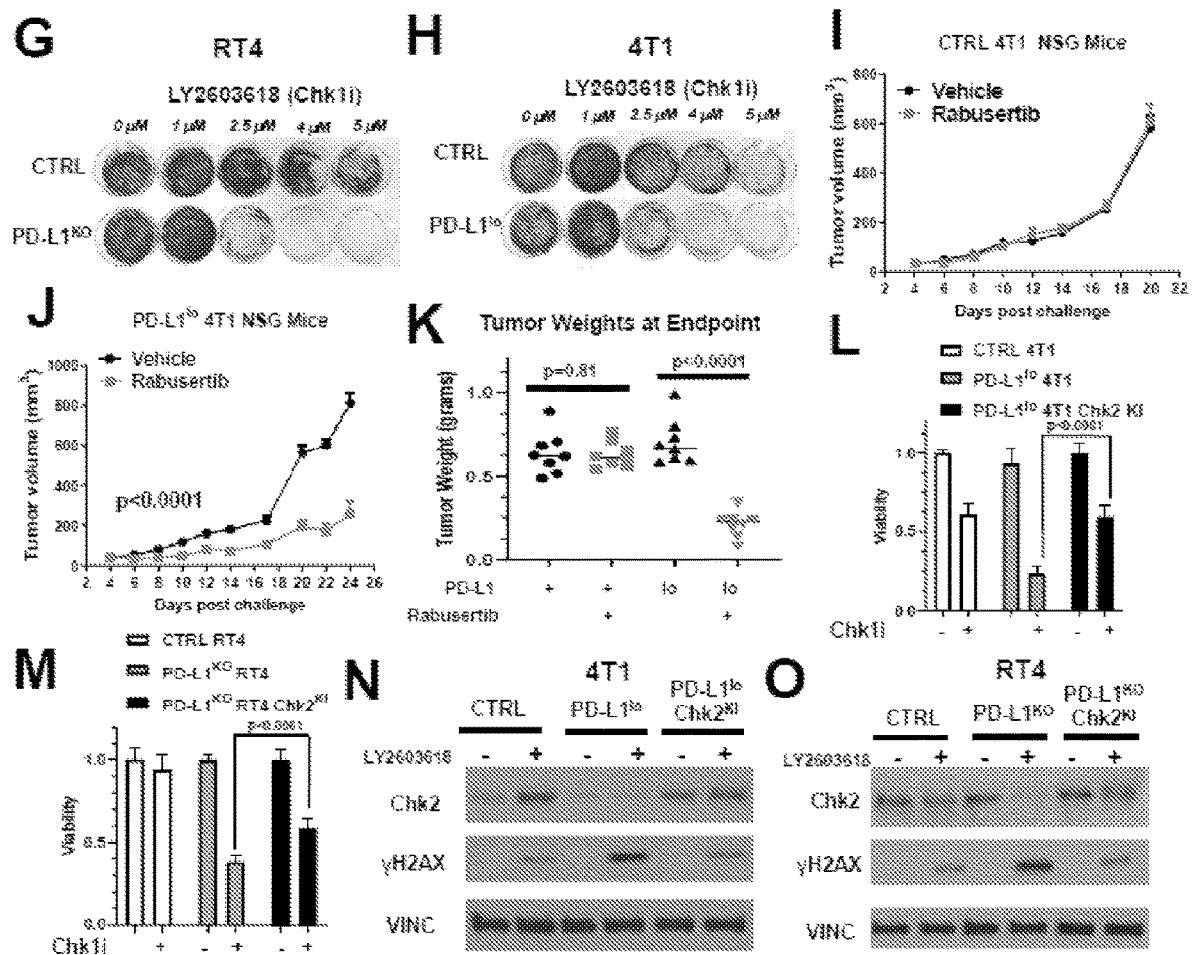
FIG. 22G-O

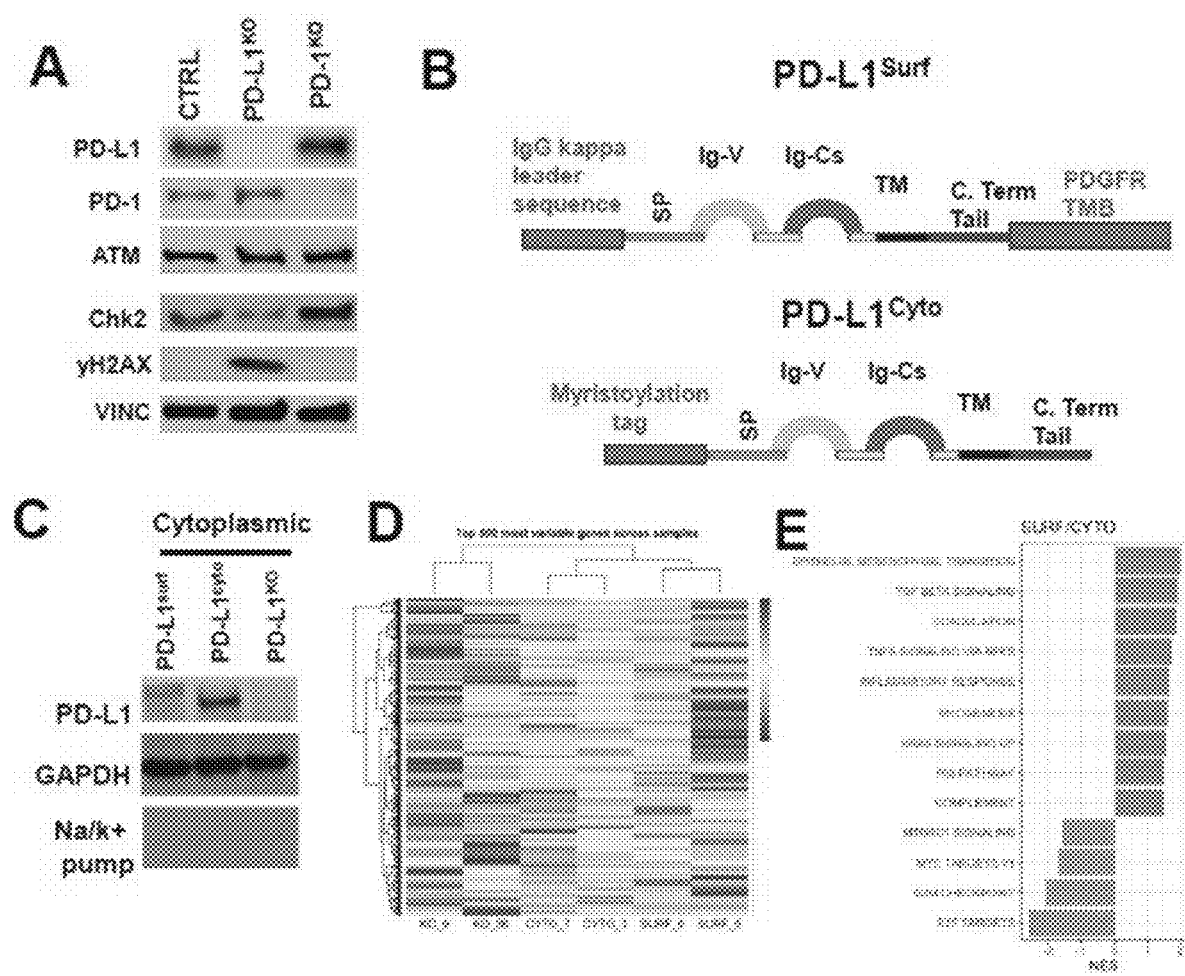
FIGS. 23A-E

F
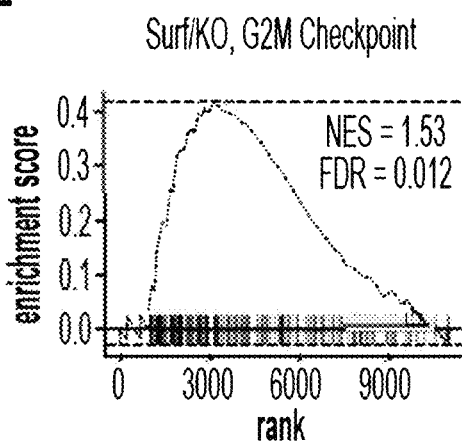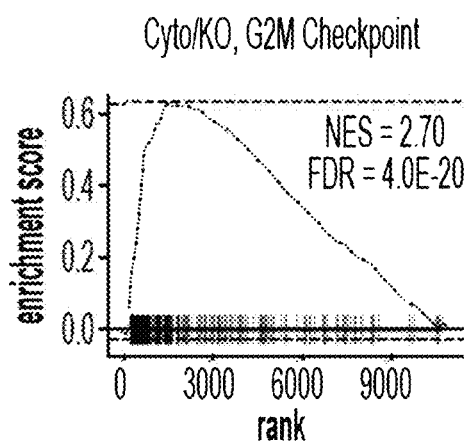
G
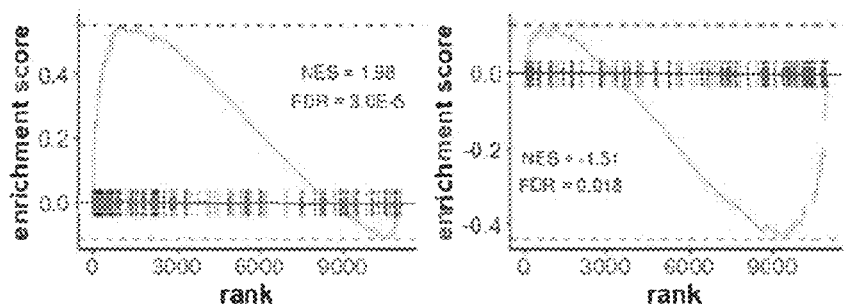
H
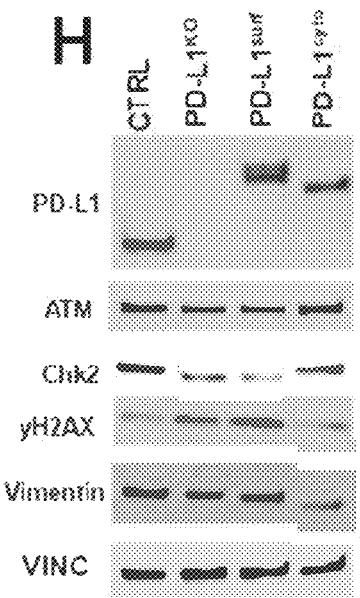
FIGS. 23F-H

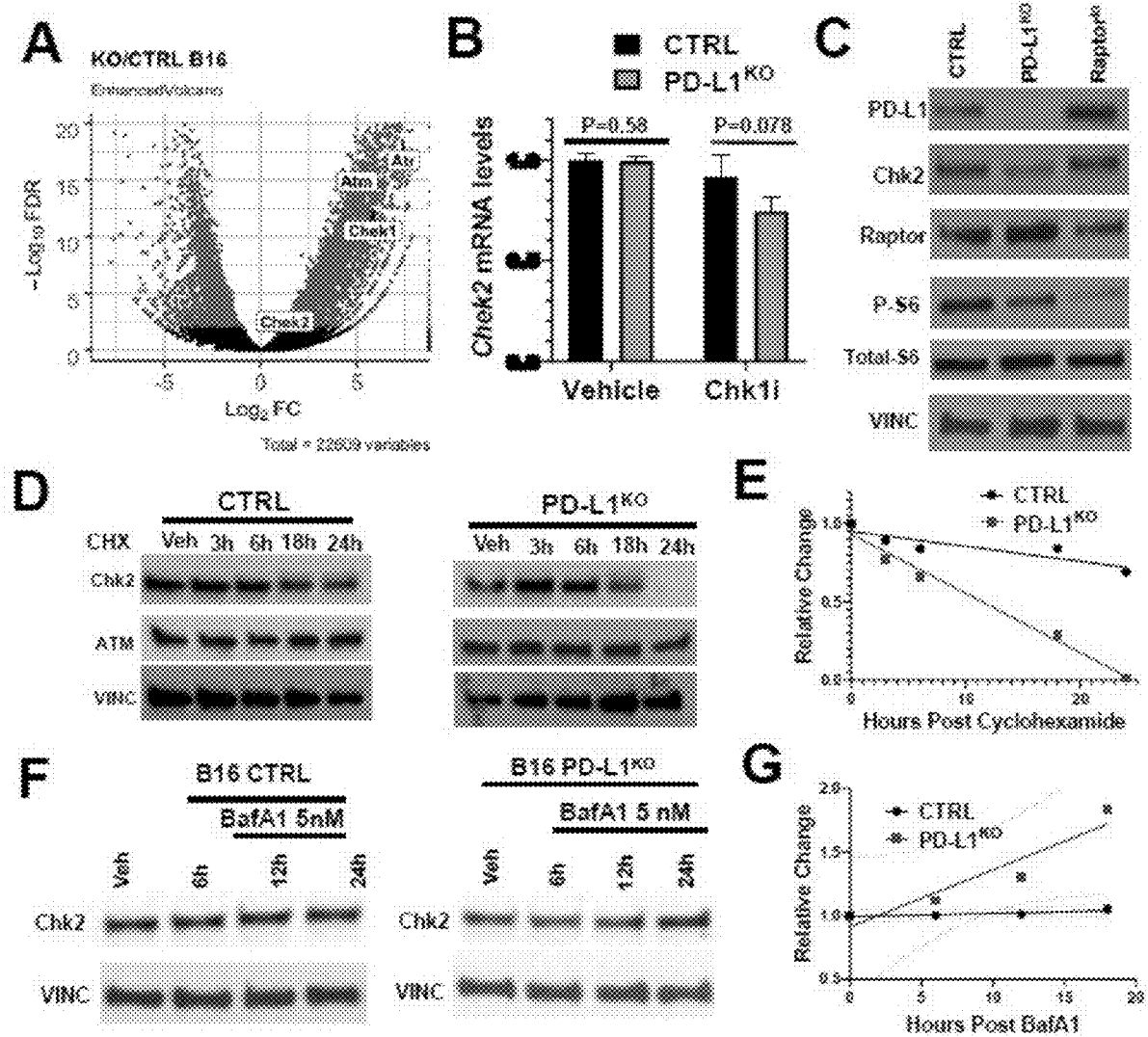
FIGS. 24A-G

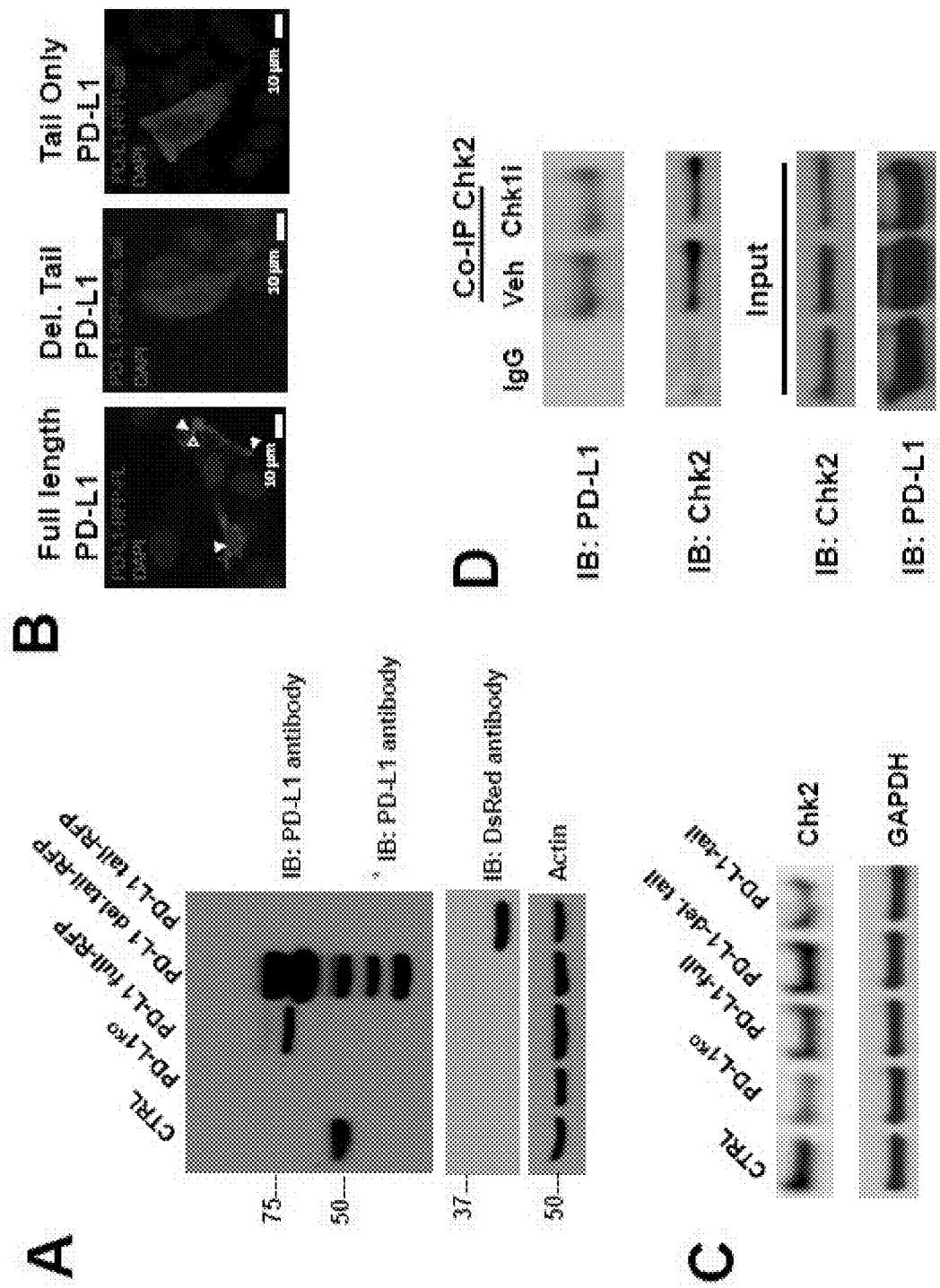
FIGS. 25A-D

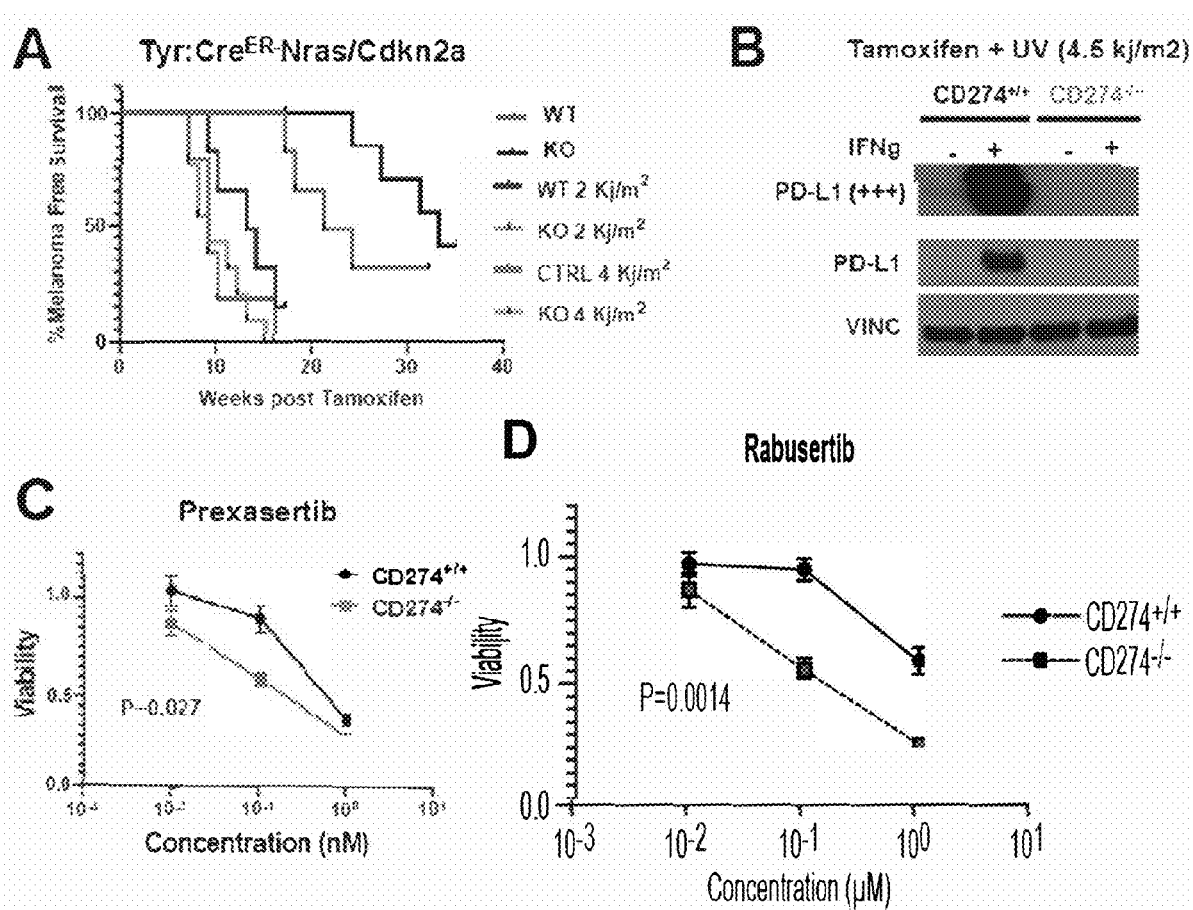
FIGS. 26A-D

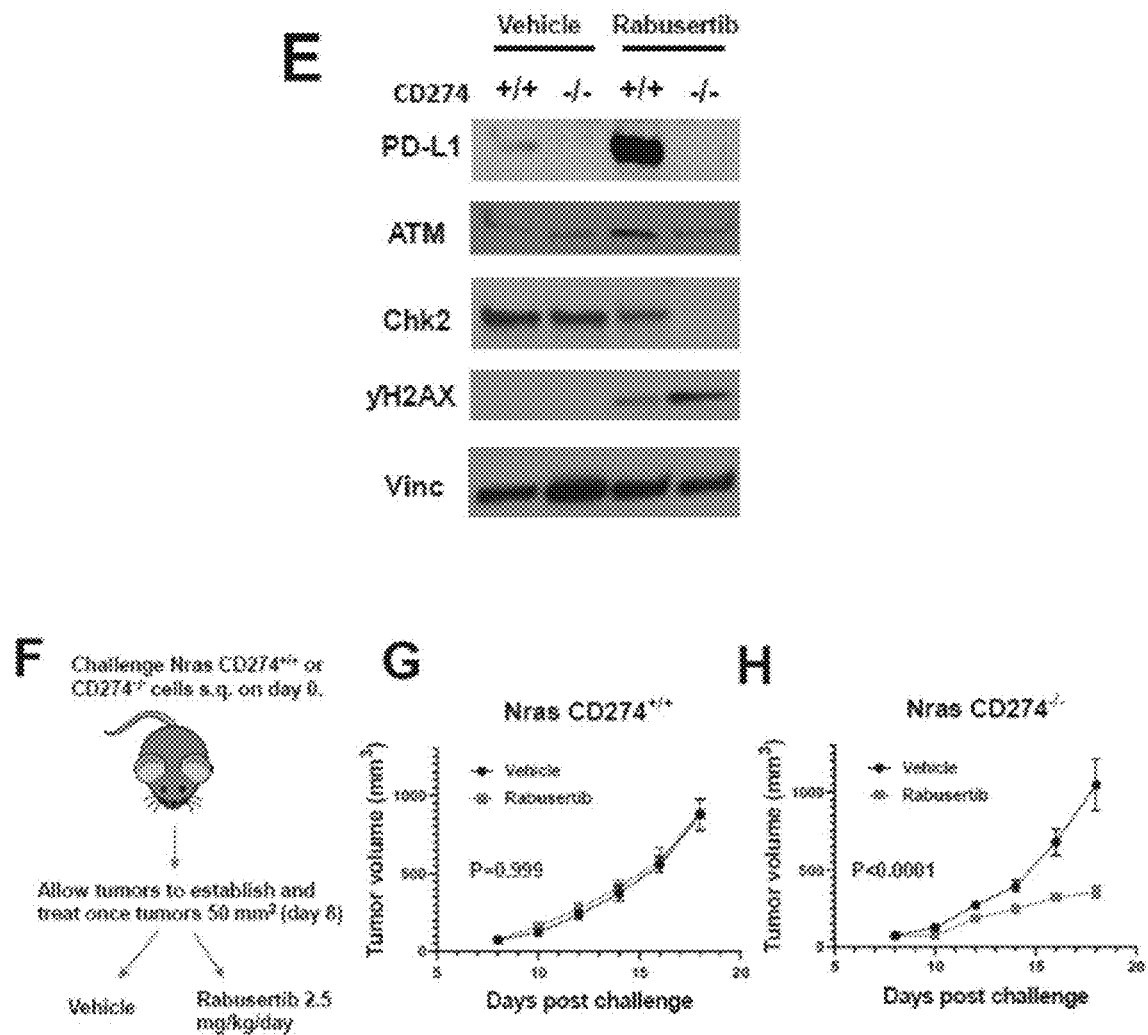
FIGS. 26E-H

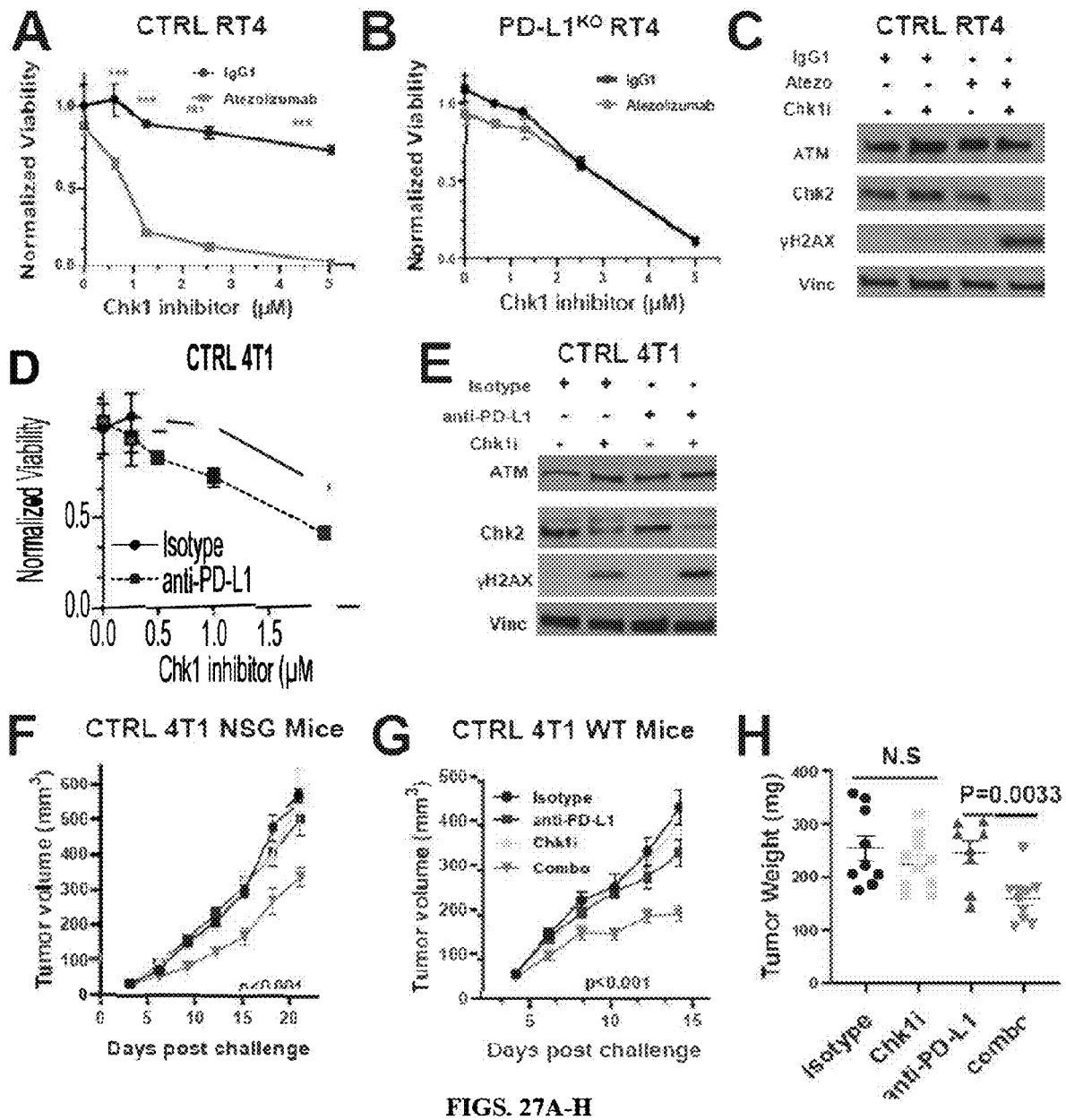
FIGS. 27A-H

AZD6738 (ATRI)

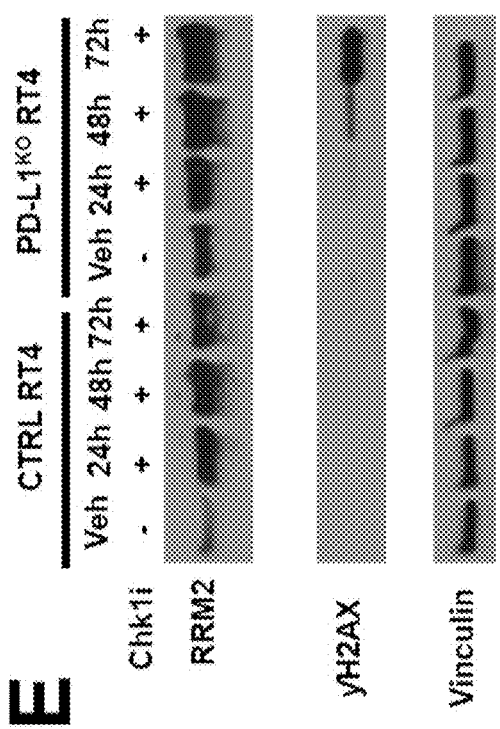
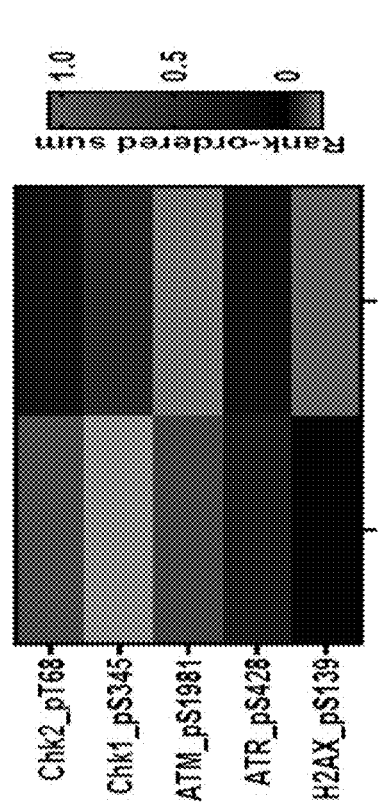
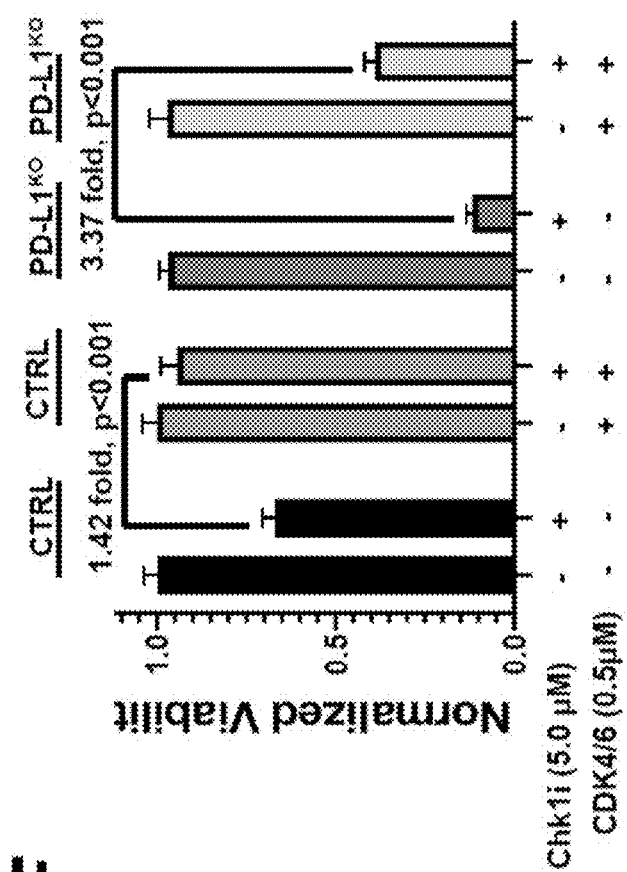
FIGS. 31D-F

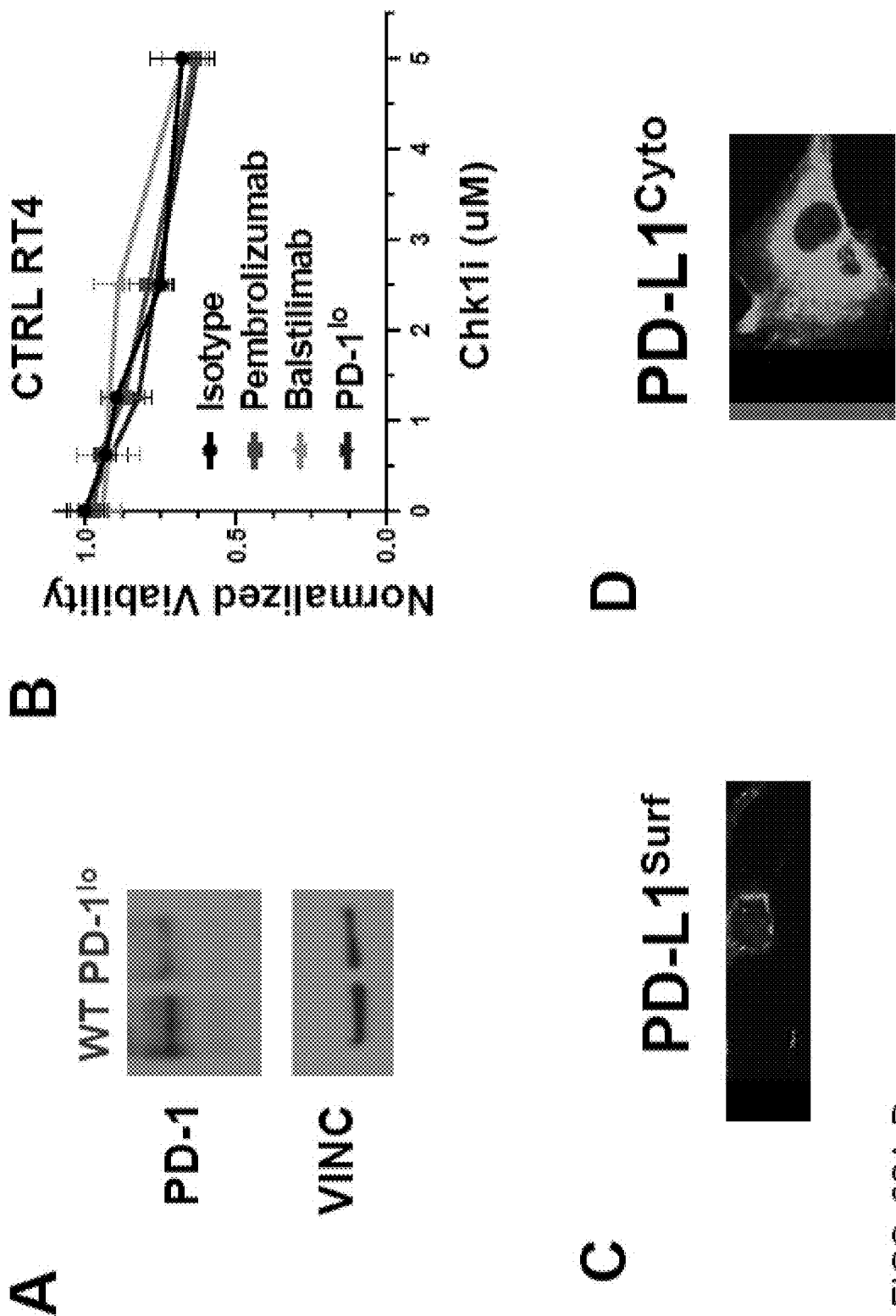
FIGS. 32A-D

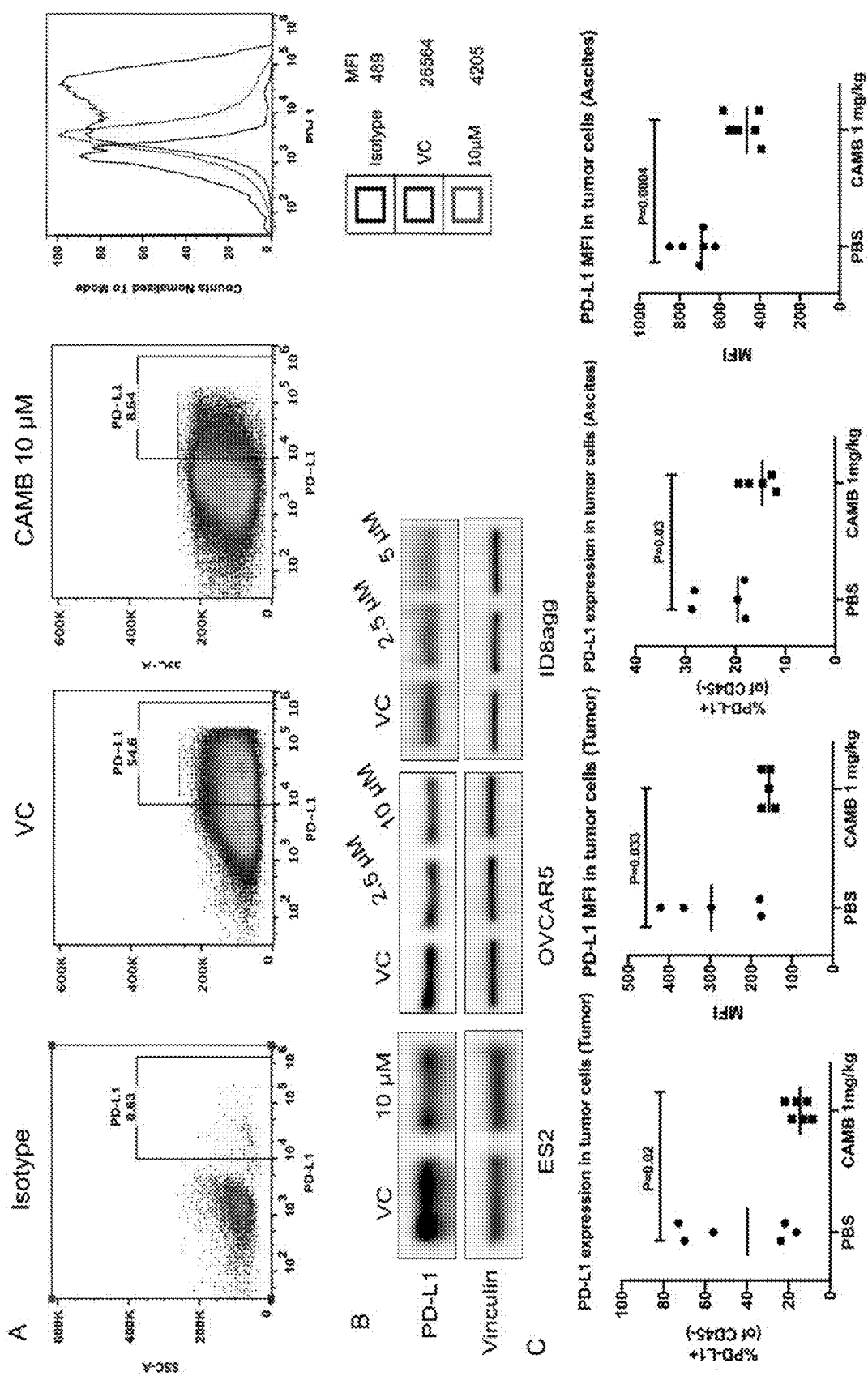
FIGS 33A-C

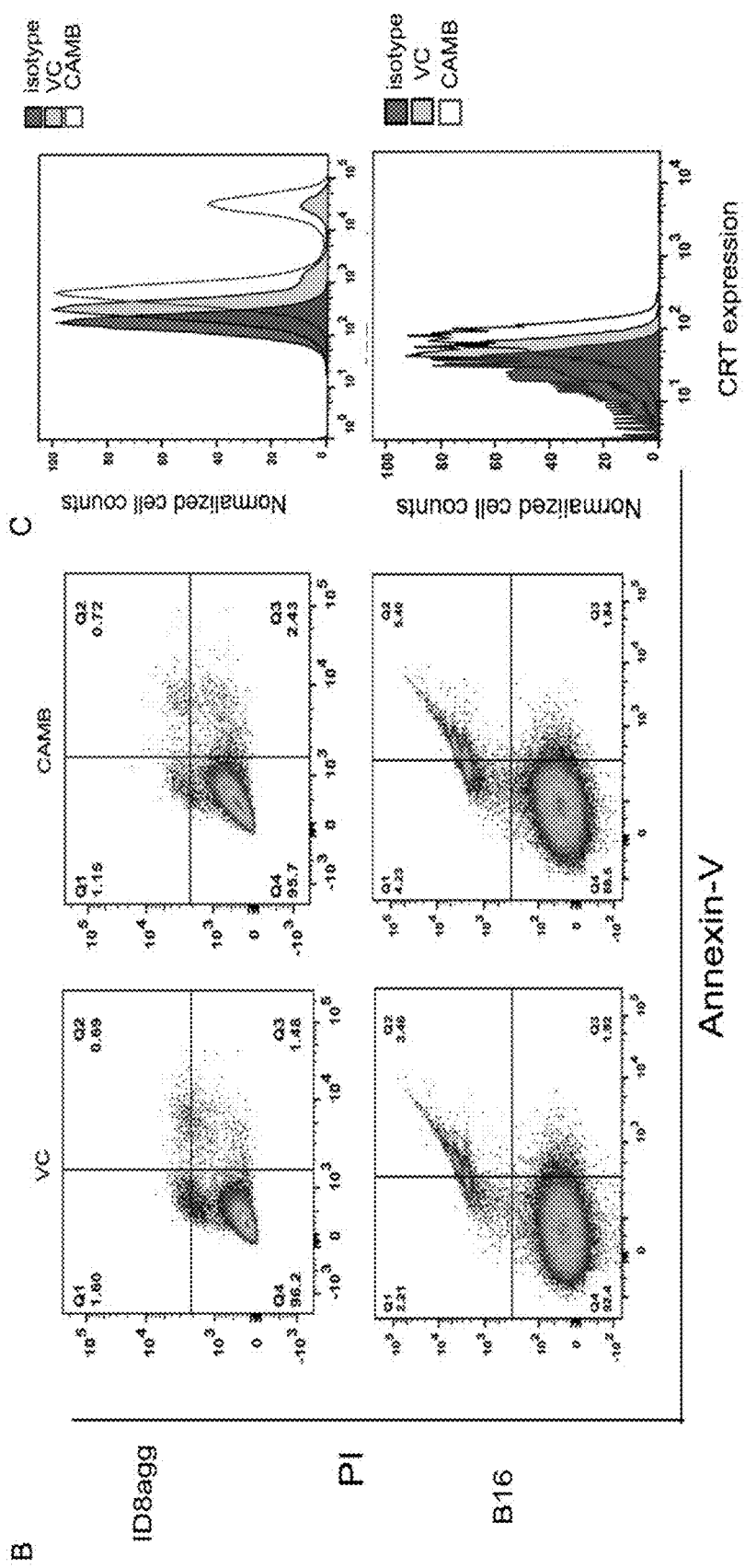
FIGS. 34B-C

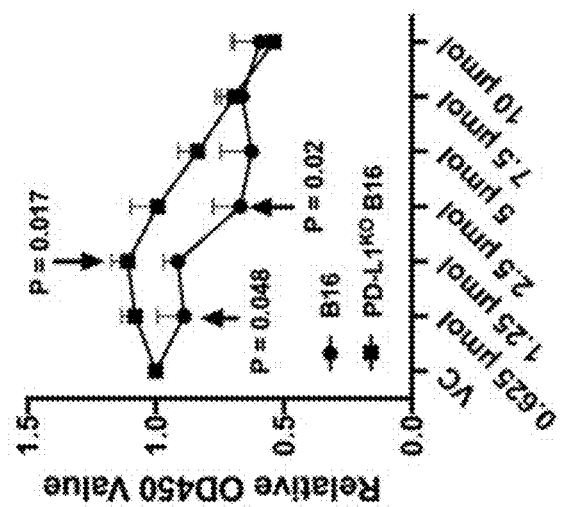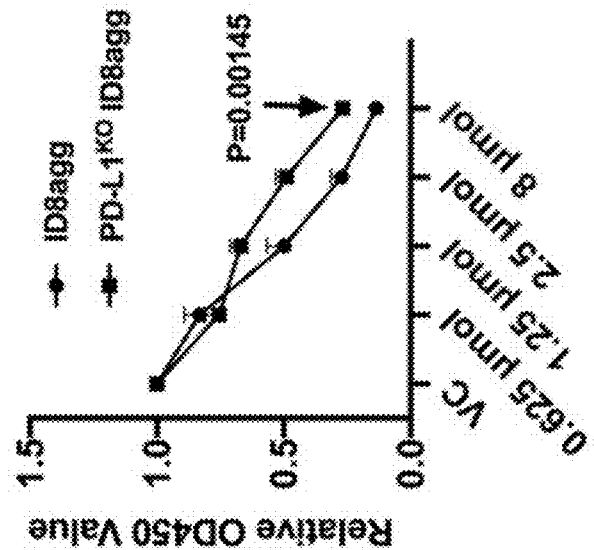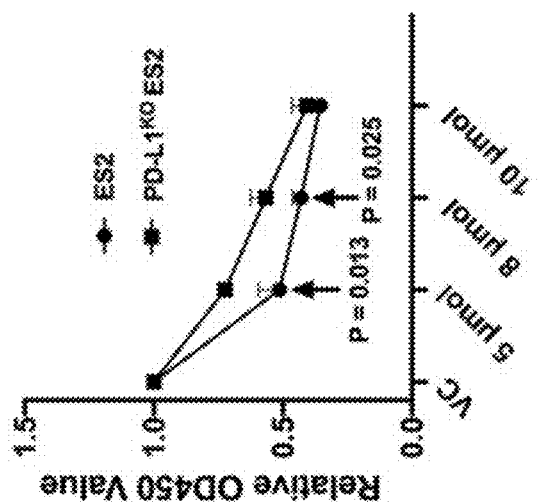
FIG. 34D

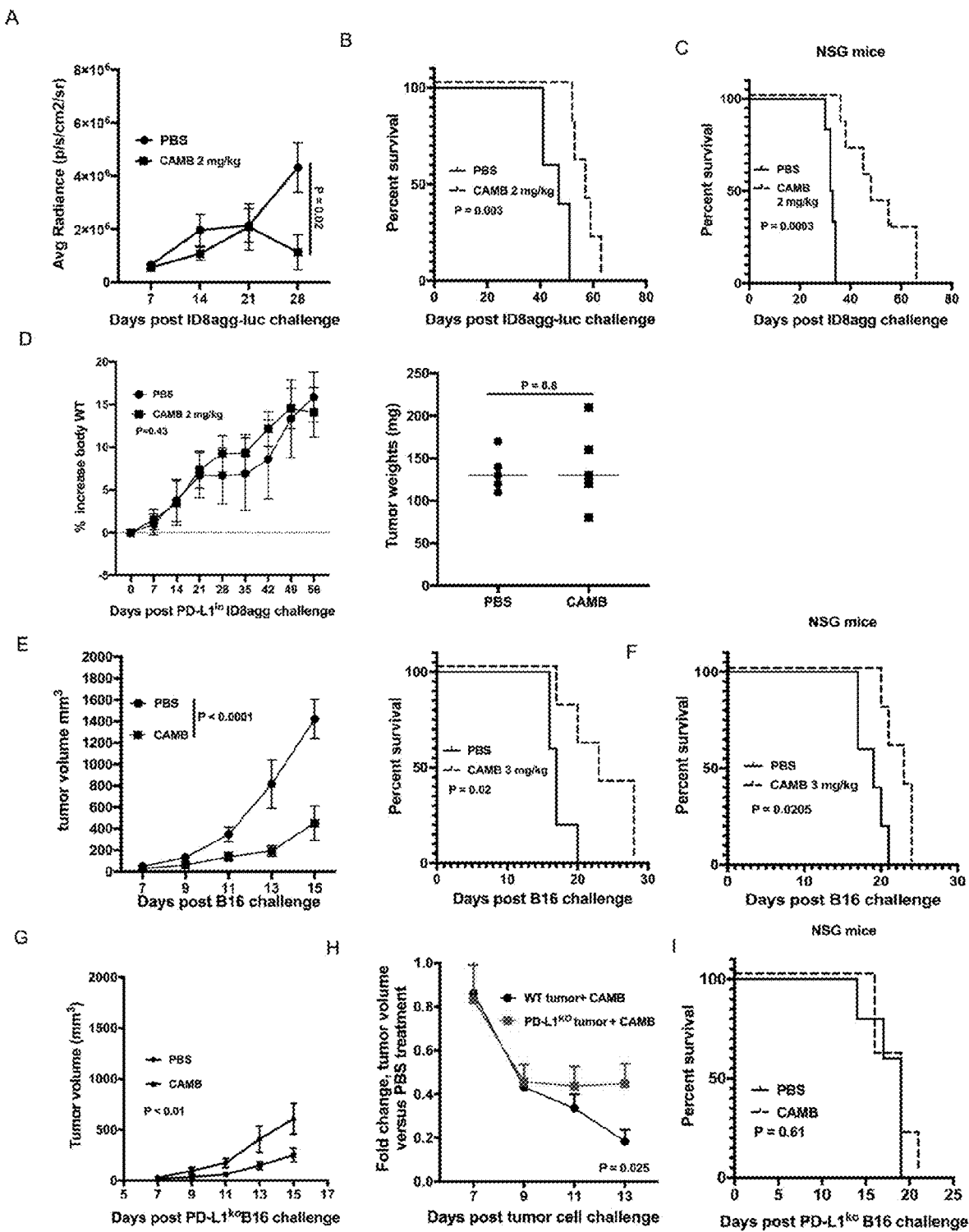
FIGS. 35A-I

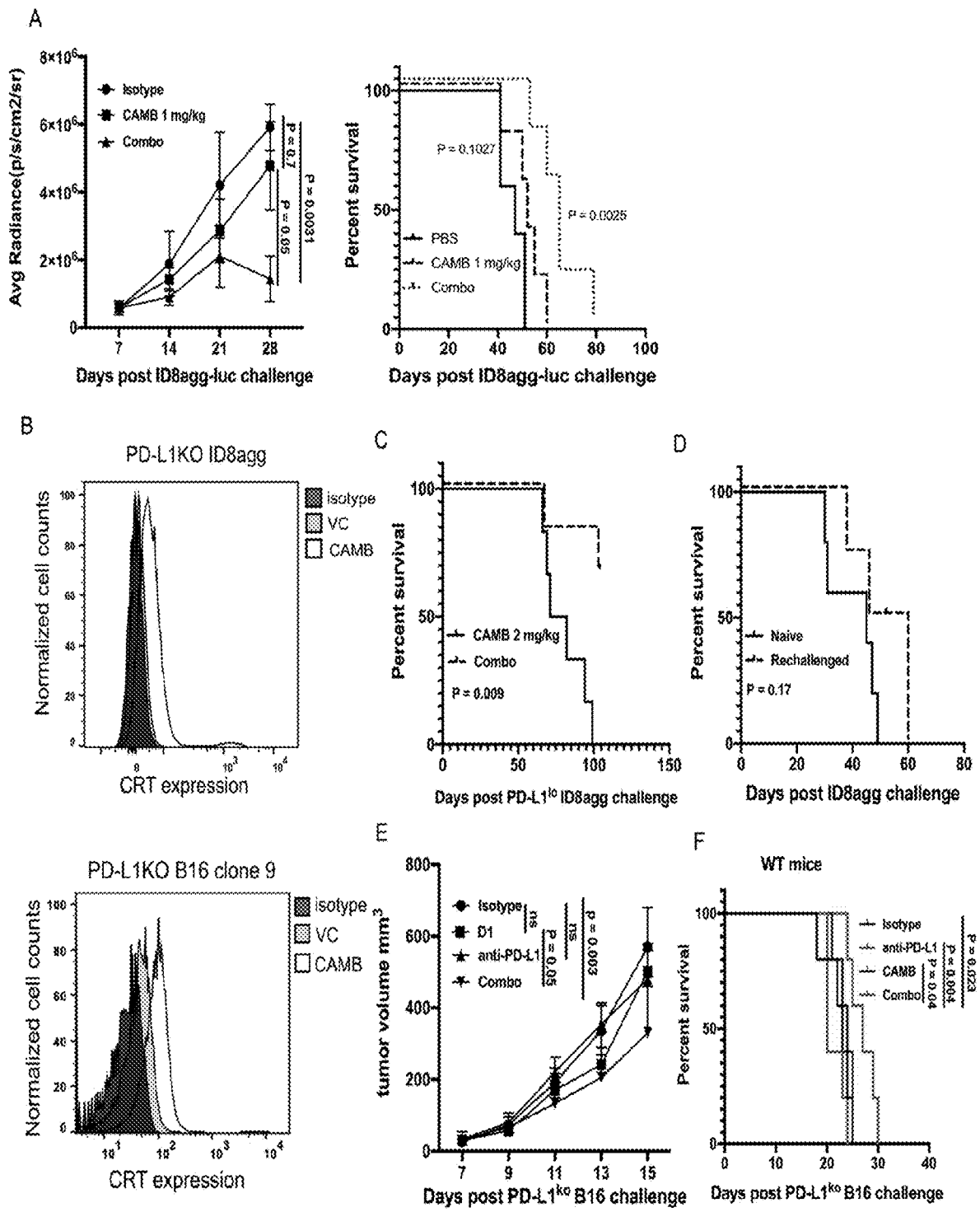
FIGS. 36A-F

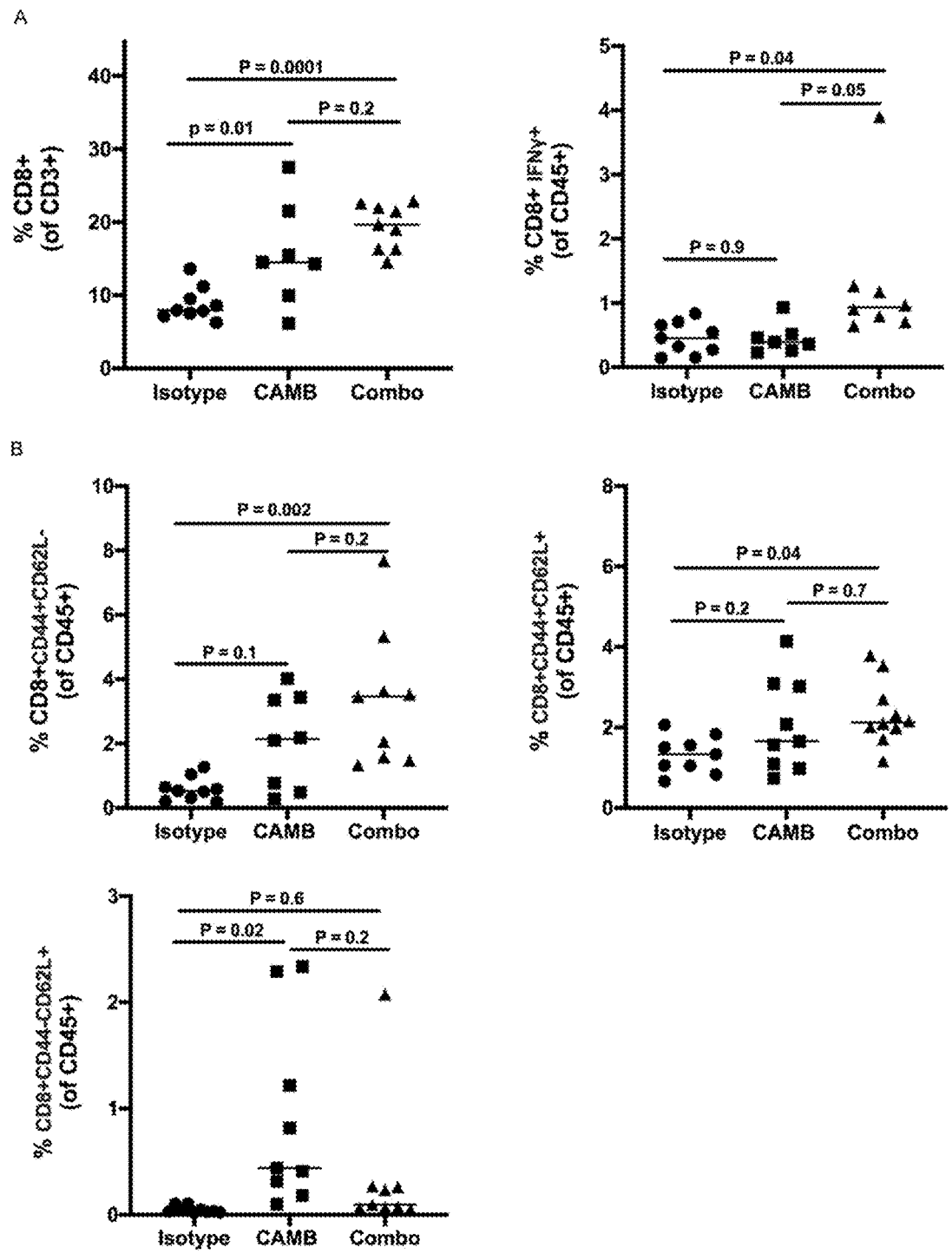
FIGS. 37A-B

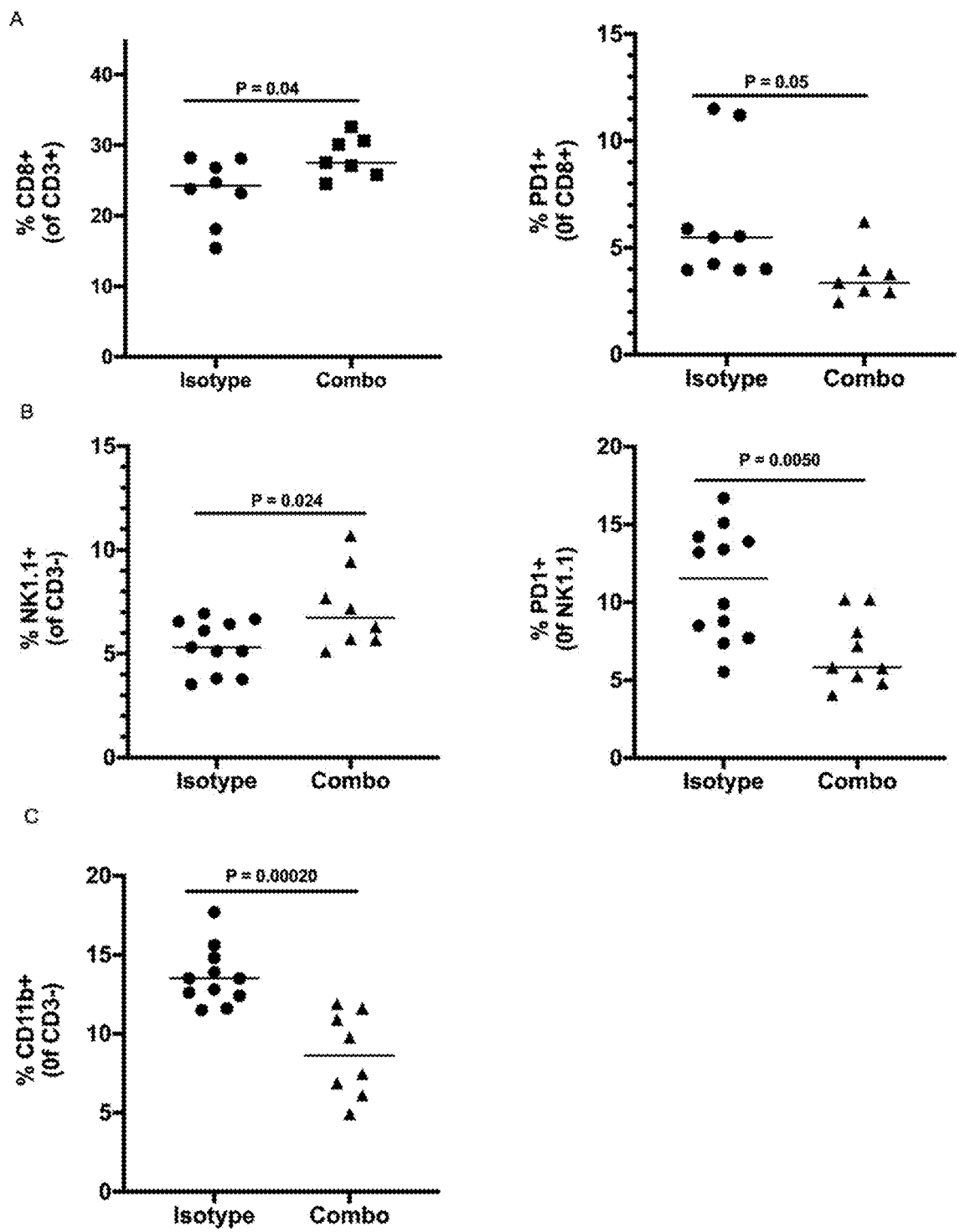
FIGS. 38A-C

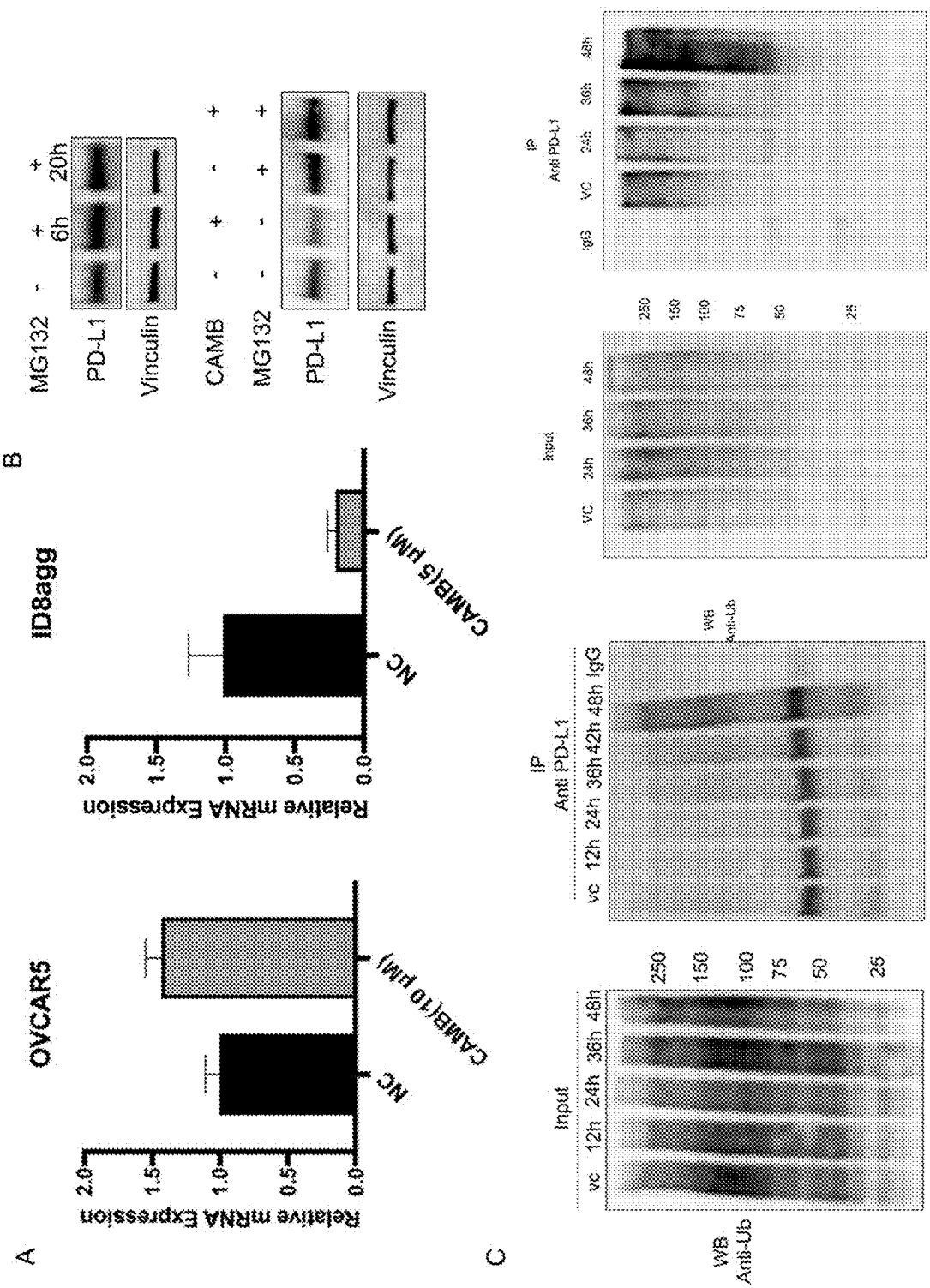
FIGS. 39A-C

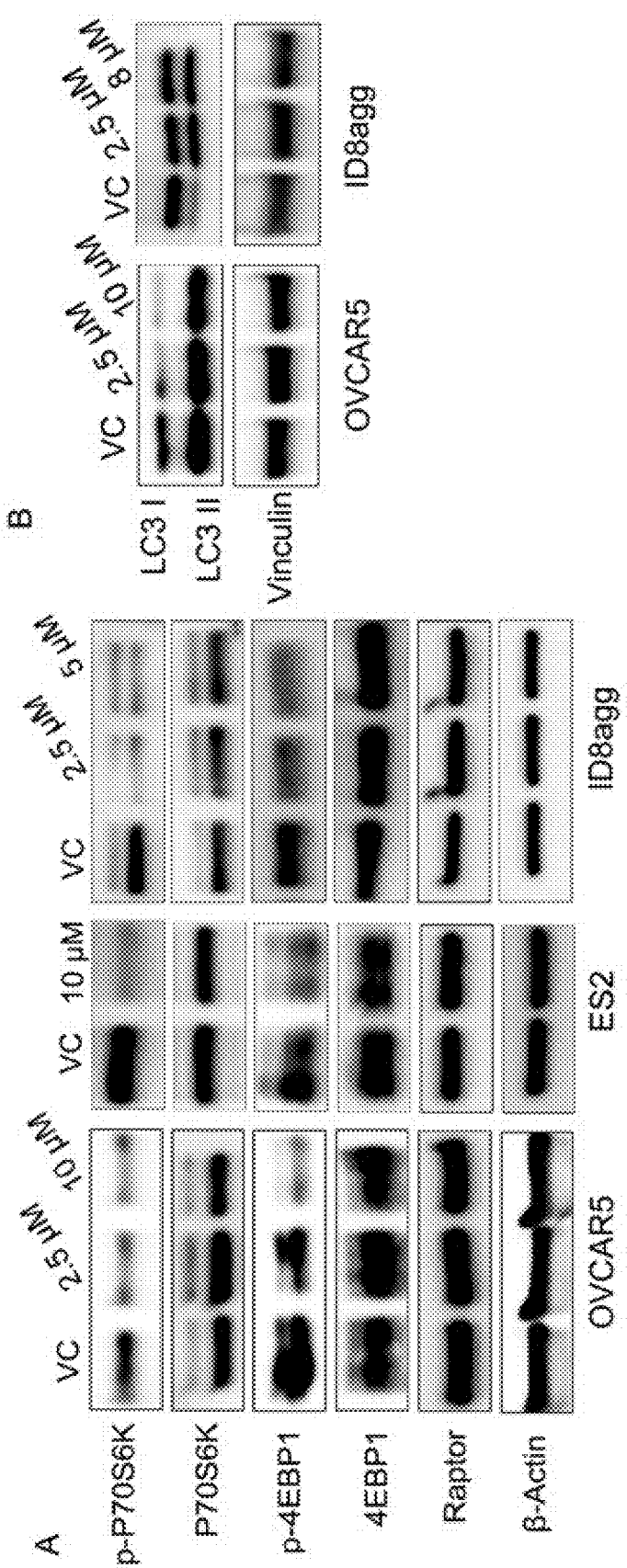
FIGS. 40A-B

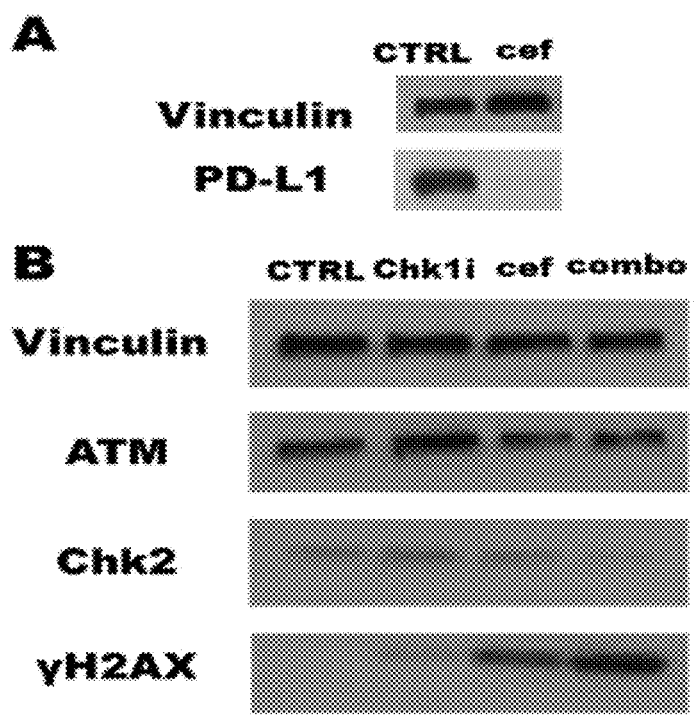
FIGS. 44A-B
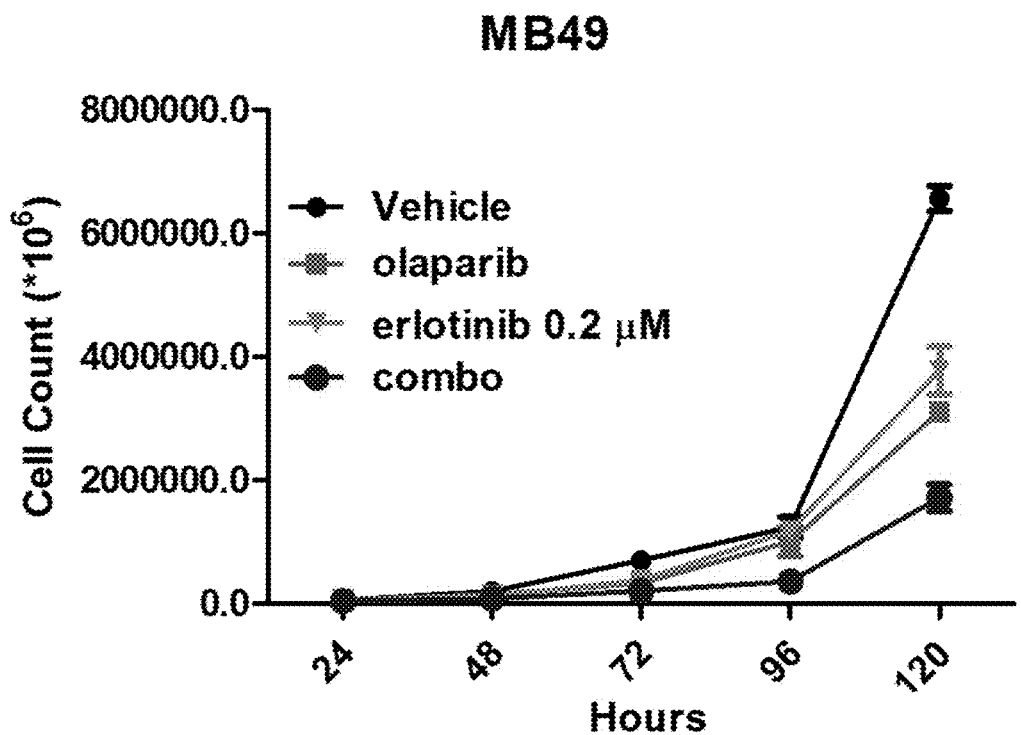
FIG. 45A

METHODS FOR DIAGNOSING AND TREATING CANCERS This application claims the benefit of U.S. Provisional Patent Application No. 62/989,164, filed Mar. 13, 2020, and U.S. Provisional Patent Application No. 63/000,187, filed Mar. 26, 2020, the entirety of which are incorporated herein by reference.

The invention was made with government support under Grant No. CA205965 awarded by the National Institutes of Health. The government has certain rights in the invention.

BACKGROUND OF THE INVENTION

This application contains a Sequence Listing, which has been submitted electronically and is hereby incorporated by reference in its entirety. The Sequence Listing was created on Mar. 11, 2021, is named CLFR.P0482US_ST.25 and is 4 KB.

1. Field of the Invention

The present invention relates generally to the field of molecular biology and medicine. More particularly, it concerns molecular biology and medicine.

2. Description of Related Art

Programmed death ligand-1 (PD-L1, CD274, B7-H1), a target of several FDA-approved cancer immunotherapies, is highly expressed on some cancers and enables immune evasion by inhibiting tumor-specific CD8+ T cells (Topalian et al., 2012). The ability of expression of cell surface PD-L1 to predict responses to PD-1/PD-L1 antibodies in many cancers is not conclusive and has been controversial (Wang et al., 2016), suggesting that additional factor(s) other than tumor surface PD-L1 can affect such immunotherapy outcomes. Predictors of patient response to anti-PD-L1 or anti-PD-1 immunotherapy are not currently reliable. Patients with epithelial ovarian cancer typically have an extremely poor response to anti-PD-1 or anti-PD-L1 immunotherapy alone.

Cancers typically have genomic instability, and mutations in cancers are common. For example, genomic instability in cancer can arise from defects in the DNA damage response (DDR) that can increase mutation rate and/or chromosomal instability to drive cancer clonal evolution, tumor heterogeneity, and treatment resistance. DDR defects can nonetheless also create vulnerabilities in cancer cells, but not normal cells, that in some instances can be exploited in cancer therapies. For example, poly (ADP-ribose) polymerase (PARP) inhibitor (PARPi) monotherapy has been approved by the FDA to treat BRCA1-deficient cancers (Fong et al., 2009).

DDRi are antitumor agents that target DDR pathways or mediators of DNA replication and repair. DDRi include Chk1, Chk2, ATM, ATR, Wee1, and DNA-PK (Pilie et al., 2018). Although several DDR inhibitors (DDRi) have been developed, predicting whether a cancer will respond to DDRi therapy is a significant clinical problem. There exists a significant clinical need to identify biomarkers that predict DDRi responses, apart from BRCA1 status, and to define DDRi resistance mechanisms.

Cancers continue to present a serious, often complex clinical problem that results in significant mortality. Clearly, there is a need for new and improved methods for treating cancers, personalizing cancer therapies, and identifying patients more likely to respond to specific anti-cancer therapies.

SUMMARY OF THE INVENTION

The present disclosure, in some aspects, overcomes limitations in the prior art by providing improved methods for treating cancers, including methods for personalizing cancer therapies and identifying cancers that may be sensitive or resistant to cancer therapies. In some aspects, it has been observed that tumor cytoplasmic PD-L1, and not surface-expressed PD-L1 (also referred to as "surface PD-L1"), predicts tumor responsiveness to therapies and patient survival. In some aspects, increased expression of any of the 5 LAMTOR proteins (referred to herein as "LAMTOR") was observed to be associated with poor prognosis and reduced survival in cancers. In some aspects, it has been observed that downstream signaling from tumor cytoplasmic PD-L1 (such as activation of mammalian target of rapamycin complex 1 [mTORC1]), can predict cancer treatment response. Additionally, in a variety of cancers, reductions in cytoplasmic PD-L1 expression have been observed to correlate with improved responsiveness to DDRi, such as inhibitors of Chk1 (Chk1i), ATM (ATMi) and/or inhibitors of PARP (PARPi). In some aspects, methods of predicting cancer treatment responses and patient prognosis based on expression of tumor cytoplasmic PD-L1, or the ratio of cytoplasmic PD-L1 to surface-expressed PD-L1, are also provided.

In some aspects, cytoplasmic PD-L1 or its downstream signaling effects have been observed to affect cancer prognosis and/or responsiveness to therapy. As shown in the below examples, using tumor cells engineered for subcellular-specific PD-L1 expression cytoplasmic, not surface-expressed, tumor PD-L1 activated mTORC1, inhibited anti-PD-L1 immune checkpoint blockade immunotherapy response, and altered tumor-infiltrating immune cells independent of tumor surface PD-L1 expression. These results were distinct from reported cytoplasmic PD-L1 tail signals and reported resistance mechanisms to immune checkpoint blockade (Wu et al., 2018). In tissues from 99 melanoma and 440 ovarian cancer patients, ~20% of melanomas and ovarian carcinomas expressed predominantly cytoplasmic PD-L1 that predicted tumor mTORC1 activation and reduced survival, and ~20% expressed predominantly surface PD-L1 that had no relationship to mTORC1 activation or survival. Using genetic manipulations of ovarian cancer and melanoma cell lines plus imaging, mass spectrometry, immunoprecipitation and bioinformatics tumor PD-L1 was observed to activate mTORC1 by affecting LAMTOR subunit messenger RNA content. Tumor Lamtor expression was observed to predicted survival in melanoma and ovarian cancer patients. An analysis of tumors obtained from a clinical trial of pembrolizumab, bevacizumab plus cyclophosphamide to treat patients with epithelial ovarian cancer revealed that tumor cytoplasmic PD-L1 predicted the clinical response of patients to the therapy, whereas surface-expressed PD-L1 and total tumor PD-L1 were uninformative for predicting clinical response. Considering that epithelial ovarian cancers typically do not respond to anti-PD-1 or anti-PD-L1 immunotherapy alone, such methods may be used, e.g., to identify patients with epithelial ovarian cancers can benefit from an anti-PD-1 or anti-PD-L1 immunotherapy.

As further shown in the below examples, reduced expression of PD-L1 in cancer cells was associated with increased sensitivity to DDRi in a variety of cancers. Cancer lines were genetically depleted of PD-L1 using either CRISPR/Cas9 (to produce "PD-L1$^{KO}$" cells) or shRNA ("PD-L1$^{lo}$" cells), and results were compared to control cancer cells. PD-L1$^{KO}$ RT4 human bladder cancer cells, PD-L1$^{KO}$ mouse ID8agg ovarian cancer cells, and PD-L1$^{KO}$ B16 mouse melanoma cells were more sensitive to cytotoxicity of gemcitabine, accumulated more γH2AX indicating DNA damage, and exhibited delayed DDR kinetics versus respective control cells. During gemcitabine exposure, PD-L1 deletion reduced Chk2 but not Chk1 or the DDR kinases ATM or ATR. Tumor-intrinsic PD-L1 was shown to affect therapy with DDR inhibitors. For example, PD-L1 depletion sensitized tumors to small molecule inhibition of Chk1, ATR, ATM or PARP. Specifically, PD-L1$^{KO}$ RT4 human bladder cancer and murine ID8agg ovarian cancer cells were observed to be highly sensitive in vitro to a Chk1 inhibitor (Chk1i) or ATR inhibitor (ATRi) versus respective control cells, but were minimally sensitive to an ATM inhibitor (ATMi) or a PARP inhibitor (PARPi). PD-L1 depletion in 4T1 murine breast cancer cells sensitized them to Chk1i but not PARPi, and PD-L1$^{KO}$ MB49 murine bladder cancer cells demonstrated high sensitivity to PARPi but not Chk1i in vitro and in vivo in NSG mice. The PARPi olaparib had no effect on PD-L1$^{KO}$ versus control B16 murine melanoma in vitro or in RAGKO mice. In contrast, olaparib significantly slowed PD-L1$^{KO}$ but not control B16 tumor growth in wild type mice, indicating a strong immune component in vivo for olaparib treatment efficacy based on tumor PD-L1 content. These results support the idea that tumor PD-L1 can be a negative biomarker for DDR inhibitor efficacy. In some embodiments, a Chk1i, ATRi, ATMi, or PARPi is administered to a patient with low tumor PD-L1 expression. Additionally, 9-(2-phosphonylmethoxyethyl) guanine (PMEG), chlorambucil, and beta-lactam antibiotics such as cefepime and ceftazidime were observed to display in anti-cancer properties and decreased expression of PD-L1 in cancer cells. Methods of treating cancers with these compounds are provided herein.

An aspect of the present disclosure relates to a method of treating a cancer in a mammalian subject, comprising (i) measuring expression of cytoplasmic or intracellular PD-L1 and/or (ii) one or more Lamtor proteins in the cancer; wherein increased expression of cytoplasmic or intracellular PD-L1 or the one or more Lamtor proteins in the cancer indicates decreased survival and/or decreased responsiveness to an immune checkpoint blockade therapy; and wherein decreased expression of cytoplasmic PD-L1 or one or more LAMTOR proteins in the cancer indicates improved survival and/or increased responsiveness to the immune checkpoint blockade therapy; wherein if the cancer is bladder cancer, then the method comprises measuring expression of cytoplasmic PD-L1 in the cancer; and (ii) administering an anti-cancer therapy to the subject. In some embodiments, the anti-cancer therapy is a DDR inhibitor (DDRi). The DDR inhibitor may be a Chk1 inhibitor (Chk1i), a PARP inhibitor (PARPi), ATM inhibitor (ATMi), or an ATR inhibitor (ATRi). In some embodiments, the PARP inhibitor is rucaprib, olaparib, or niraparib. In some embodiments, the ATM inhibitor is AZD0156 or KU-55933. In some embodiments, the ATR inhibitor is VE-821, AZD6738, or VX970. In some embodiments, the Chk1 inhibitor is MK8776 (SCH900776), LY2603618, CCT245737, or GDC-0575. The immune blockade therapy may be an antibody that selectively binds PD-L1 or PD-1. In some embodiments, the antibody selectively binds PD-1. In some embodiments, the antibody is cemiplimab, nivolumab, pembrolizumab, spartalizumab (PDR001), camrelizumab (SHR1210), sintilimab (IBI308), tislelizumab (BGB-A317), toripalimab (JS 001), AMP-224, or AMP-514. In some embodiments, the antibody selectively binds PD-L1. In some embodiments, the antibody is atezolizumab, avelumab, durvalumab, KN035, CK-301, AUNP12, CA-170, or BMS-986189. The anti-cancer therapy can be 9-(2-phosphonylmethoxyethyl) guanine (PMEG), chlorambucil, or a beta-lactam antibiotic (e.g., cefepime or ceftazidime). In some embodiments, the beta-lactam antibiotic is not a penem. The cancer may be a gastric cancer, hepatocellular carcinoma, renal cell carcinoma, esophageal cancer, pancreatic cancer, ovarian cancer, bladder cancer, lung cancer, colorectal cancer, melanoma, breast cancer, Merkel cell carcinoma, cervical cancer, hepatocellular cancer, head and neck cancer, sarcoma, lymphoma, leukemia, urothelial cancer, myelodysplasia, or sarcoma. In some embodiments, the cancer is an ovarian cancer, a bladder cancer, a breast cancer, or a melanoma. In some embodiments, the measuring comprises immunohistochemistry, mass spectroscopy, immunoprecipitation, flow cytometry, or digital imaging. The subject may be a human. The method may further comprise detecting a mTORC1 signal or the one or more Lamtor proteins in the cancer. The one or more LAMTOR protein is may be, LAMTOR2, LAMTOR3, LAMTOR4, or LAMTOR5. In some embodiments, the anti-cancer therapy is an immune checkpoint blockade therapy. The immune checkpoint blockade therapy may comprise or consist of an antibody that selectively binds PD-1 or PD-L1. In some embodiments, the anti-cancer therapy is a chemotherapeutic, an immunotherapy, a gene therapy, a radiotherapy, a small molecule, a DNA therapy, an RNA therapy, a cryotherapy, a cellular therapy, a toll-like receptor agonist, a dual-targeting agent, a triple-targeting agent, or a surgery. In some embodiments, the anti-cancer therapy is cyclophosphamide or bevacizumab. In some embodiments, the cancer is a bladder cancer, a breast cancer, or a melanoma; and wherein the DDR inhibitor is a Chk1 inhibitor (Chk1i) or a PARP inhibitor (PARPi). In some embodiments, the cancer is a melanoma or an ovarian cancer; and wherein the anti-cancer therapy is pembrolizumab, bevacizumab, or cyclophosphamide. In some embodiments, the method does not comprise measuring surface PD-L1 expression by the cancer. In some embodiments, the method comprises measuring surface PD-L1 expression by the cancer. In some embodiments, the increased expression of cytoplasmic PD-L1 indicates that greater than 50% of the total expressed PD-L1 in the cancer is cytoplasmic PD-L1. In some embodiments, the increased expression has a ratio of cytoplasmic PD-L1:surface PD-L1 of at least 1.5, at least 2, at least 2.5, at least 3, at least 3.5, or at least 4; or wherein the cancer expresses at least 1.5, at least 2, at least 3, at least 3.5, or at least 4 times more cytoplasmic PD-L1 than surface PD-L1.

Another aspect of the present disclosure relates to a method for identifying an anti-cancer compound, comprising: (i) contacting a cancerous cell with a test compound; and subsequently (ii) measuring cytoplasmic PD-L1 or one or more LAMTOR proteins in the cancerous cell; wherein the cancerous cell expresses cytoplasmic PD-L1 and/or one or more LAMTOR proteins; and wherein a decrease in cytoplasmic PD-L1 or one or more LAMTOR proteins in the cancerous cell indicates that the test compound has anti-cancer properties; wherein if the cancer is bladder cancer, then the method comprises measuring expression of cytoplasmic PD-L1 in the cancer. The cancer may be a gastric cancer, hepatocellular carcinoma, renal cell carcinoma, esophageal cancer, pancreatic cancer, ovarian cancer, bladder cancer, lung cancer, colorectal cancer, melanoma, breast cancer, Merkel cell carcinoma, cervical cancer, hepatocellular cancer, head and neck cancer, sarcoma, lymphoma, leukemia, urothelial cancer, myelodysplasia, or sarcoma. In some embodiments, the cancer is an ovarian cancer, a bladder cancer, a breast cancer, or a melanoma. In some embodiments, the measuring comprises immunohistochemistry, mass spectroscopy, immunoprecipitation, flow cytometry, or digital imaging.

An in vitro method for diagnosing a cancer, comprising: (i) obtaining a tissue sample comprising a cancer; and (ii) measuring the presence, absence, or level of expression of cytoplasmic PD-L1 or one or more LAMTOR proteins in the cancer; wherein increased expression of cytoplasmic PD-L1 or the one or more LAMTOR proteins in the cancer indicates poor survival and/or decreased responsiveness to immune checkpoint blockade therapies; and wherein decreased expression of cytoplasmic PD-L1 or the one or more LAMTOR proteins in the cancer indicates improved survival and/or increased responsiveness to immune checkpoint blockade therapies; wherein if the cancer is bladder cancer, then the method comprises measuring expression of cytoplasmic PD-L1 in the cancer. The immune blockade therapy may be a DDR inhibitor (DDRi). In some embodiments, the DDR inhibitor is a Chk1 inhibitor (Chk1i), a PARP inhibitor (PARPi), ATM inhibitor (ATMi), or an ATR inhibitor (ATRi). In some embodiments, the PARP inhibitor is rucaprib, olaparib, or niraparib. In some embodiments, the ATM inhibitor is AZD0156, or KU-55933. In some embodiments, the ATR inhibitor is VE-821, AZD6738, or VX970. In some embodiments, the Chk1 inhibitor is MK8776 (SCH900776), LY2603618, CCT245737, or GDC-0575. In some embodiments, the immune blockade therapy is an antibody that selectively binds PD-L1 or PD-1. In some embodiments, the antibody selectively binds PD-1. In some embodiments, the antibody is cemiplimab, nivolumab, pembrolizumab, spartalizumab (PDR001), camrelizumab (SHR1210), sintilimab (IBI308), tislelizumab (BGB-A317), toripalimab (JS 001), Nivolumab (BMS-936558), AMP-224, or AMP-514. In some embodiments, the antibody selectively binds PD-L1. In some embodiments, the antibody is atezolizumab, avelumab, durvalumab, KN035, CK-301, AUNP12, CA-170, or BMS-986189. The anti-cancer therapy is 9-(2-phosphonylmethoxyethyl) guanine (PMEG) or chlorambucil. The cancer may be a gastric cancer, hepatocellular carcinoma, renal cell carcinoma, esophageal cancer, pancreatic cancer, ovarian cancer, bladder cancer, lung cancer, colorectal cancer, melanoma, breast cancer, Merkel cell carcinoma, cervical cancer, hepatocellular cancer, head and neck cancer, sarcoma, lymphoma, leukemia, urothelial cancer, myelodysplasia, or sarcoma. In some embodiments, the cancer is an ovarian cancer, a bladder cancer, a breast cancer, or a melanoma. The measuring may comprise immunohistochemistry, mass spectroscopy, immunoprecipitation, flow cytometry, or digital imaging. The subject may be a human. The method may further comprise detecting mTORC1 or LAMTOR in the cancer. The method may further comprise administering to the subject a chemotherapeutic, an immunotherapy, a gene therapy, a radiotherapy, or a surgery. In some embodiments, the method further comprises administering to the subject an immune checkpoint blockade therapy. The immune checkpoint blockade therapy may comprise or consist of an antibody that selectively binds PD-1 or PD-L1. The method may further comprise administering to the subject a chemotherapeutic, an immunotherapy, a gene therapy, a radiotherapy, or a surgery. In some embodiments, the cancer is a bladder cancer, a breast cancer, or a melanoma; and wherein the DDR inhibitor is a Chk1 inhibitor (Chk1i) or a PARP inhibitor (PARPi). In some embodiments, the cancer is a melanoma or an ovarian cancer; and wherein the anti-cancer therapy is pembrolizumab, bevacizumab, or cyclophosphamide. In some embodiments, the increased expression of cytoplasmic PD-L1 indicates that greater than 50% of the total expressed PD-L1 in the cancer is cytoplasmic PD-L1. In some embodiments, the increased expression has a ratio of cytoplasmic PD-L1:surface PD-L1 of at least 1.5, at least 2, at least 2.5, at least 3, at least 3.5, or at least 4; or wherein the cancer expresses at least 1.5, at least 2, at least 2.5, at least 3, at least 3.5, or at least 4 times more cytoplasmic PD-L1 than surface PD-L1.

An aspect of the present disclosure relates to a method of treating a cancer in a mammalian subject, comprising measuring expression of i) cytoplasmic PD-L1 and/or ii) one or more Lamtor proteins in the cancer; wherein if the expression of cytoplasmic or intracellular PD-L1 or one or more LAMTOR proteins is decreased relative to a normal control, then the method comprises administering an anti-cancer therapy to the subject. The anti-cancer therapy may be a DDR inhibitor (DDRi) or an immune blockade therapy. In some embodiments, the anti-cancer therapy is a DDR inhibitor (DDRi). The DDR inhibitor may be a Chk1 inhibitor (Chk1i), a PARP inhibitor (PARPi), ATM inhibitor (ATMi), or an ATR inhibitor (ATRi). In some embodiments, the PARP inhibitor is rucaprib, olaparib, or niraparib. In some embodiments, the ATM inhibitor is AZD0156 or KU-55933. In some embodiments, the ATR inhibitor is VE-821, AZD6738, or VX970. In some embodiments, the Chk1 inhibitor is MK8776 (SCH900776), LY2603618, CCT245737, or GDC-0575. The immune blockade therapy may be an antibody that selectively binds PD-L1 or PD-1. In some embodiments, the antibody selectively binds PD-1, wherein the antibody is cemiplimab, nivolumab, pembrolizumab, spartalizumab (PDR001), camrelizumab (SHR1210), sintilimab (IBI308), tislelizumab (BGB-A317), toripalimab (JS 001), AMP-224, or AMP-514. In some embodiments, the antibody selectively binds PD-L1, wherein the antibody is atezolizumab, avelumab, durvalumab, KN035, CK-301, AUNP12, CA-170, or BMS-986189. The anti-cancer therapy may be 9-(2-phosphonylmethoxyethyl) guanine (PMEG) or chlorambucil. The anti-cancer therapy may be a beta-lactam antibiotic such as, e.g., a penam, carbapenem, an oxapenam, a carbapenem, a monobactam, a cephem, a carbacephem, or an oxacephem. In some embodiments, the beta-lactam antibiotic is a cephem. The cephem may be, e.g., cefazolin, cephalexin, cephalosporin, cephalothin, cefapirin, cefaclor, cefamandole, cefuroxime, cefotetan, cefoxitin, cefixime, cefotaxime, cefpodoxime, ceftazidime, ceftriaxone, cefdinir, cefepime, cefpirome, or ceftaroline. In some embodiments, the cephalosporin is cefepime or ceftazidime. In some embodiments, the beta-lactam antibiotic is not a penem. In some embodiments, the method comprises administering to the mammalian subject both: (a) an antibody that selectively binds PD-L1 or PD-1, and (b) a PARP inhibitor, a Chk1 inhibitor, or chlorambucil. In some embodiments, the antibody that selectively binds PD-L1 or PD-1 is cemiplimab, nivolumab, pembrolizumab, spartalizumab (PDR001), camrelizumab (SHR1210), sintilimab (IBI308), tislelizumab (BGB-A317), toripalimab (JS 001), AMP-224, AMP-514, atezolizumab, avelumab, durvalumab, KN035, CK-301, AUNP12, CA-170, or BMS-986189. In some embodiments, the PARP inhibitor is rucaprib, olaparib, or niraparib. In select embodiments, the PARP inhibitor is olaparib. In some embodiments, the Chk1 inhibitor is MK8776 (SCH900776), LY2603618, CCT245737, or GDC-0575. In some embodiments, chlorambucil is administered to the mammalian subject. The cancer may be, e.g., a gastric cancer, hepatocellular carcinoma, renal cell carcinoma, esophageal cancer, pancreatic cancer, ovarian cancer, bladder cancer, lung cancer, colorectal cancer, melanoma, breast cancer, Merkel cell carcinoma, cervical cancer, hepatocellular cancer, head and neck cancer, sarcoma, lymphoma, leukemia, urothelial cancer, myelodysplasia, or sarcoma. In some embodiments, the cancer is an ovarian cancer, a bladder cancer, a breast cancer, or a melanoma. The cancer may be a breast cancer. In some embodiments, the breast cancer comprises a mutation in BRCA1. In some embodiments, the breast cancer does not comprise a mutation in BRCA2. In some embodiments, the breast cancer does not comprise a mutation in BRCA1 or BRCA2. In some embodiments, the cytoplasmic PD-L1 is located within the nucleus. The measuring may comprise immunohistochemistry, mass spectroscopy, immunoprecipitation, flow cytometry, or digital imaging. In some embodiments, the mammalian subject is a human. The method may further comprise detecting a mTORC1 signal or the one or more Lamtor proteins (e.g., LAMTOR1, LAMTOR2, LAMTOR3, LAMTOR4, and/or LAMTOR5) in the cancer. The anti-cancer therapy may be an immune checkpoint blockade therapy. The immune checkpoint blockade therapy may comprise or consist of an antibody that selectively binds PD-1 or PD-L1. The anti-cancer therapy may be a chemotherapeutic, an immunotherapy, a gene therapy, a radiotherapy, a small molecule, a DNA therapy, an RNA therapy, a cryotherapy, a cellular therapy, a toll-like receptor agonist, a dual-targeting agent, a triple-targeting agent, or a surgery. In some embodiments, the anti-cancer therapy is cyclophosphamide or bevacizumab. In some embodiments, the cancer is a bladder cancer, a breast cancer, or a melanoma; and wherein the DDR inhibitor is a Chk1 inhibitor (Chk1i) or a PARP inhibitor (PARPi). In some embodiments, the cancer is a melanoma or an ovarian cancer; and wherein the anti-cancer therapy is pembrolizumab, bevacizumab, or cyclophosphamide. In some embodiments, the method does not comprise measuring surface PD-L1 expression by the cancer. In some embodiments, the method comprises measuring surface PD-L1 expression by the cancer. In some embodiments, the increased expression of cytoplasmic or intracellular PD-L1 indicates that greater than 50% of the total expressed PD-L1 in the cancer is cytoplasmic or intracellular PD-L1. In some embodiments, the increased expression has a ratio of cytoplasmic or intracellular PD-L1: surface PD-L1 of at least 1.5, or wherein the cancer expresses at least 1.5 times more cytoplasmic or intracellular PD-L1 than surface PD-L1. In some embodiments, the increased expression has a ratio of cytoplasmic or intracellular PD-L1:surface PD-L1 of at least 2, or wherein the cancer expresses at least 2 times more cytoplasmic or intracellular PD-L1 than surface PD-L1. In some embodiments, the increased expression has a ratio of cytoplasmic or intracellular PD-L1:surface PD-L1 of at least 2.5, or wherein the cancer expresses at least 2.5 times more cytoplasmic or intracellular PD-L1 than surface PD-L1. In some embodiments, the increased expression has a ratio of cytoplasmic or intracellular PD-L1:surface PD-L1 of at least 3, or wherein the cancer expresses at least 3 times more cytoplasmic or intracellular PD-L1 than surface PD-L1. In some embodiments, the increased expression has a ratio of cytoplasmic or intracellular PD-L1:surface PD-L1 of at least 4, or wherein the cancer expresses at least 4 times more cytoplasmic or intracellular PD-L1 than surface PD-L1.

Another aspect of the present invention relates to a method for identifying an anti-cancer compound, comprising: (i) contacting a cancerous cell with a test compound; and subsequently (ii) measuring the level of expression in the cancerous cell of: (a) cytoplasmic PD-L1 and/or (b) one or more LAMTOR proteins; wherein the cancerous cell expresses cytoplasmic or intracellular PD-L1 and/or one or more LAMTOR proteins; and wherein a decrease in cytoplasmic or intracellular PD-L1 or one or more LAMTOR proteins in the cancerous cell indicates that the test compound has anti-cancer properties. The cancer may be a gastric cancer, hepatocellular carcinoma, renal cell carcinoma, esophageal cancer, pancreatic cancer, ovarian cancer, bladder cancer, lung cancer, colorectal cancer, melanoma, breast cancer, Merkel cell carcinoma, cervical cancer, hepatocellular cancer, head and neck cancer, sarcoma, lymphoma, leukemia, urothelial cancer, myelodysplasia, or sarcoma. In some embodiments, the cancer is an ovarian cancer, a bladder cancer, a breast cancer, or a melanoma. The measuring may comprise immunohistochemistry, mass spectroscopy, immunoprecipitation, flow cytometry, or digital imaging.

Yet another aspect of the present disclosure relates to an in vitro method for diagnosing a cancer, comprising: i) obtaining a tissue sample comprising a cancer; and ii) measuring the level of expression in the cancer of (a) cytoplasmic or intracellular PD-L1 and/or (b) one or more LAMTOR proteins; wherein if the expression of cytoplasmic or intracellular PD-L1 or one or more LAMTOR proteins is decreased relative to a normal control, then the method comprises administering an anti-cancer therapy to the subject. The anti-cancer therapy may be a DDR inhibitor (DDRi) or an immune blockade therapy. In some embodiments, the immune blockade therapy is a DDR inhibitor (DDRi). In some embodiments, the DDR inhibitor is a Chk1 inhibitor (Chk1i), a PARP inhibitor (PARPi), ATM inhibitor (ATMi), or an ATR inhibitor (ATRi). The PARP inhibitor may be rucaprib, olaparib, or niraparib. The ATM inhibitor may be AZD0156, or KU-55933. The ATR inhibitor may be VE-821, AZD6738, or VX970. The Chk1 inhibitor may be MK8776 (SCH900776), LY2603618, CCT245737, or GDC-0575. The immune blockade therapy may be an antibody that selectively binds PD-L1 or PD-1. In some embodiments, the antibody selectively binds PD-1, wherein the antibody is cemiplimab, nivolumab, pembrolizumab, spartalizumab (PDR001), camrelizumab (SHR1210), sintilimab (IBI308), tislelizumab (BGB-A317), toripalimab (JS 001), Nivolumab (BMS-936558), AMP-224, or AMP-514. In some embodiments, the antibody selectively binds PD-L1, wherein the antibody is atezolizumab, avelumab, durvalumab, KN035, CK-301, AUNP12, CA-170, or BMS-986189. The anti-cancer therapy may be 9-(2-phosphonylmethoxyethyl) guanine (PMEG) or chlorambucil. The anti-cancer therapy may be 9-(2-phosphonylmethoxyethyl) guanine (PMEG) or chlorambucil. The anti-cancer therapy may be a beta-lactam antibiotic such as, e.g., a penam, carbapenem, an oxapenam, a monobactam, a cephem, a carbacephem, or an oxacephem. In some embodiments, the beta-lactam antibiotic is a cephem. The cephem may be cefazolin, cephalexin, cephalosporin, cephalothin, cefapirin, cefaclor, cefamandole, cefuroxime, cefotetan, cefoxitin, cefixime, cefotaxime, cefpodoxime, ceftazidime, ceftriaxone, cefdinir, cefepime, cefpirome, or ceftaroline. In some embodiments, the beta-lactam antibiotic is cefepime or ceftazidime. The cancer may be a gastric cancer, hepatocellular carcinoma, renal cell carcinoma, esophageal cancer, pancreatic cancer, ovarian cancer, bladder cancer, lung cancer, colorectal cancer, melanoma, breast cancer, Merkel cell carcinoma, cervical cancer, hepatocellular cancer, head and neck cancer, sarcoma, lymphoma, leukemia, urothelial cancer, myelodysplasia, or sarcoma. In some embodiments, the cancer is an ovarian cancer, a bladder cancer, a breast cancer, or a melanoma. The measuring may comprise immunohistochemistry, mass spectroscopy, immunoprecipitation, flow cytometry, or digital imaging. In some embodiments, the subject is a human. The method may further comprise detecting mTORC1 or LAMTOR in the cancer. In some embodiments, the method further comprises administering to the subject an immune checkpoint blockade therapy. The immune checkpoint blockade therapy may comprise or consist of an antibody that selectively binds PD-1 or PD-L1. The method may further comprise administering to the subject a chemotherapeutic, an immunotherapy, a gene therapy, a radiotherapy, or a surgery. In some embodiments, the cancer is a bladder cancer, a breast cancer, or a melanoma; and wherein the DDR inhibitor is a Chk1 inhibitor (Chk1i) or a PARP inhibitor (PARPi). In some embodiments, the cancer is a melanoma or an ovarian cancer; and wherein the anti-cancer therapy is pembrolizumab, bevacizumab, or cyclophosphamide. In some embodiments, the increased expression of cytoplasmic PD-L1 indicates that greater than 50% of the total expressed PD-L1 in the cancer is cytoplasmic or intracellular PD-L1. In some embodiments, the increased expression has a ratio of cytoplasmic PD-L1: surface PD-L1 of at least 1.5, or wherein the cancer expresses at least 1.5 times more cytoplasmic or intracellular PD-L1 than surface PD-L1. In some embodiments, the increased expression has a ratio of cytoplasmic or intracellular PD-L1:surface PD-L1 of at least 2, or wherein the cancer expresses at least 2 times more cytoplasmic PD-L1 than surface PD-L1. In some embodiments, the increased expression has a ratio of cytoplasmic or intracellular PD-L1: surface PD-L1 of at least 2.5, or wherein the cancer expresses at least 2.5 times more cytoplasmic PD-L1 than surface PD-L1. In some embodiments, the increased expression has a ratio of cytoplasmic or intracellular PD-L1: surface PD-L1 of at least 3, or wherein the cancer expresses at least 3 times more cytoplasmic PD-L1 than surface PD-L1. In some embodiments, the increased expression has a ratio of cytoplasmic or intracellular PD-L1:surface PD-L1 of at least 4, or wherein the cancer expresses at least 4 times more cytoplasmic PD-L1 than surface PD-L1.

Another aspect of the present invention relates to a method of treating a cancer in a mammalian subject, comprising administering to the subject a therapeutically relevant dose of: (i) 9-(2-phosphonylmethoxyethyl) guanine (PMEG), chlorambucil, or a beta-lactam antibiotic, and (ii) an antibody that selectively binds PD-L1 or PD-1 to the mammalian subject, and wherein the cancer is melanoma, ovarian cancer, gastric cancer, hepatocellular carcinoma, renal cell carcinoma, esophageal cancer, pancreatic cancer, ovarian cancer, bladder cancer, lung cancer, colorectal cancer, melanoma, breast cancer, cervical cancer, hepatocellular cancer, head and neck cancer, sarcoma, lymphoma, leukemia, urothelial cancer, myelodysplasia, or sarcoma. In some embodiments, the beta-lactam antibiotic is not a penem. In some embodiments, the antibody that selectively binds PD-L1 or PD-1 is cemiplimab, nivolumab, pembrolizumab, spartalizumab (PDR001), camrelizumab (SHR1210), sintilimab (IBI308), tislelizumab (BGB-A317), toripalimab (JS 001), AMP-224, AMP-514, atezolizumab, avelumab, durvalumab, KN035, CK-301, AUNP12, CA-170, or BMS-986189. The method may further comprise administering to the mammalian subject a therapeutically relevant dose of a PARP inhibitor or a Chk1 inhibitor. The PARP inhibitor may be rucaprib, olaparib, or niraparib. In some embodiments, the PARP inhibitor is olaparib. The Chk1 inhibitor may be MK8776 (SCH900776), LY2603618, CCT245737, or GDC-0575. Chlorambucil may be administered to the mammalian subject. The cancer may be resistant to a DDR inhibitor. The method may further comprise reversing or decreasing the resistance to the DDR inhibitor. The beta-lactam antibiotic may be a penam, carbapenem, an oxapenam, a penem, a carbapenem, a monobactam, a cephem, a carbacephem, or an oxacephem. In some embodiments, the beta-lactam antibiotic is a cephem. The cephem may be, e.g., cefazolin, cephalexin, cephalosporin, cephalothin, cefapirin, cefaclor, cefamandole, cefuroxime, cefotetan, cefoxitin, cefixime, cefotaxime, cefpodoxime, ceftazidime, ceftriaxone, cefdinir, cefepime, cefpirome, or ceftaroline. In some embodiments, the beta-lactam antibiotic is cefepime or ceftazidime. In some embodiments, the mammalian subject is a human.

"Cytoplasmic PD-L1" as used herein refers to PD-L1 that is present within a cell and not located on or within the cell surface membrane. The cytoplasmic PD-L1 may or may not be located in the nucleus. As would be immediately appreciated by one of skill, the nucleus is located within the cytoplasm of a cell. In some embodiments, the cytoplasmic PD-L1 is located within the cytoplasm but outside of the nucleus. A variety of methods for detecting, measuring, and/or quantifying cytoplasmic PD-L1 may be used in embodiments of the present disclosure.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIGS. 1A-F: Tumor cell-intrinsic PD-L1 confers chemoresistance, promotes DNA repair kinetics, and alters DDR signaling in bladder cancer cells. FIG. 1A, Viability in vitro of RT4 cells treated with gemcitabine for 48 hours at the indicated doses. FIG. 1B, Western blot analysis of RT4 control (CTRL) and PD-L1$^{KO}$ cells for DNA damage (γH2AX) 24 hours post gemcitabine exposure (10 ng/ml). FIG. 1C, Schematic depiction of experimental design for assessing DNA repair kinetics. To its right, Western blot analysis of RT4 control and PD-L1$^{KO}$ cells for γH2AX at indicated recovery time periods following irradiation (2 Gy). FIG. 1D, Western blots for ATM/Chk2 and ATR/Chk1 DDR signaling pathways in CTRL versus PD-L1$^{KO}$ RT4 cells 24 hours post gemcitabine exposure (10 ng/ml). FIG. 1E, Confocal images of CTRL versus PD-L1$^{KO}$ RT4 cells for p-BRCA1$^{Ser1524}$ and p-RPA32$^{S4/S8}$ DNA damage repair nuclear foci following 2 Gy X-irradiation (1 h recovery) or 1 ng/ml gemcitabine (4 h incubation) as indicated. FIG. 1F, In PD-L1$^{KO}$ ID8agg cells we observed robust Chk1 activation over control cells following gem treatment indicating tumor intrinsic PD-L1 suppresses activation of ATR/Chk1/p-Chk1 signaling and DNA damage from excess replication stress.

FIGS. 2A-D: PD-L1 status predicts synthetic lethality to ATR or Chk1 inhibitors in bladder and ovarian cancer cells in vitro. Viability of CTRL versus PD-L1$^{KO}$ RT4 and ID8agg cells treated with indicated agents. FIG. 2A, LY2603618 (Chk1 inhibitor) FIG. 2B, AZD0156 (ATM inhibitor) FIG. 2C, AZD6738 (ATR inhibitor) FIG. 2D, olaparib (PARP inhibitor) for 5 days at indicated doses (Mean+/−SEM, n=6 replicates, ***, P<0.001, unpaired t-test). Viability normalized to vehicle controls.

FIGS. 3A-D: Tumor intrinsic PD-L1 controls immune-independent sensitivity to Chk1 or PARP inhibition in bladder and breast cancer cells in vitro and in vivo. Viability assays of CTRL versus PD-L1-depleted cells: FIG. 3A, MB49 cells or FIG. 3B, 4T1 cells following LY2603618 (Chk1i) or olaparib (PARPi) treatment (mean+/−SEM, n=6 replicates, ***, P<0.001, unpaired t-test). FIG. 3C, Tumor growth in NSG mice subcutaneously challenged with CTRL or PD-L1$^{KO}$ MB49 cells, and then treated with olaparib as described in Materials and Methods. P values, two-way ANOVA. Tumor weights of CTRL versus PD-L1$^{KO}$ tumors at endpoint. P values, unpaired t-test. FIG. 3D, Treatments scheme and tumor growth in NSG mice challenged with CTRL or PD-L1$^{lo}$ 4T1 cells and treated with rabusertib (LY2603618, Chk1 inhibitor).

FIGS. 4A-D: Tumor PD-L1 promotes resistance to PARP inhibitor treatment in vivo dependent on adaptive immunity. FIG. 4A, Viability assay of CTRL versus PD-L1$^{KO}$ B16 melanoma cells following in vitro olaparib (PARPi) treatment (mean+/−SEM, n=6 replicates, ***, P<0.001, unpaired t-test). Tumor growth in WT mice subcutaneously challenged with CTRL (FIG. 4B) or PD-L1$^{KO}$ (FIG. 4C) B16 cells treated with olaparib at dose and schedule described in Materials and Methods. FIG. 4D, RAG2$^{KO}$ mice challenged with PD-L1$^{KO}$ B16 and treated with olaparib as in FIG. 4B and FIG. 4C. P values, two-way ANOVA.

FIGS. 5A-H: PD-L1 expression in control and PD-L1-depleted tumor cells. PD-L1 replete (CTRL) or cell lines were depleted of PD-L1 by shRNA or deleted for PD-L1 (PD-L1$^{KO}$) using CRISPR/Cas9 assayed for PD-L1 expression by Western blot or flow cytometry in: FIG. 5A, 4T1; FIG. 5B, B16; FIG. 5C, ID8agg; FIG. 5D, Rt4 FIG. 5E, ID8agg. FIG. 5F, B16, FIG. 5G, MB49, FIG. 5H, ES2.

FIGS. 6A-C: FIG. 6A, Viability in vitro of CTRL and PD-L1$^{KO}$ ID8agg cells treated with gemcitabine for 48 hours at indicated doses. FIG. 6B, Western blot of CTRL and PD-L1$^{KO}$ ID8agg cells for DNA damage (y-H2AX) 24 hours post gemcitabine exposure (10 or 100 ng/ml). FIG. 6C, Western blots of CTRL and PD-L1$^{KO}$ ID8agg cells for γH2AX, total Chk1 and p-Chk1 at indicated times following 1 ng/ml or 10 ng/ml gemcitabine. +++ indicates longer exposure time.

FIGS. 7A-B: FIG. 7A, Western blots of CTRL and PD-L1$^{KO}$ RT4 cells following 24 h gemcitabine (10 ng/ml) treatment for total BRCA1, NBS1, RAD51 and RAD50. FIG. 7B, Confocal images of CTRL versus PD-L1$^{KO}$ RT4 cells for p-BRCA1$^{Ser1524}$ and p-RPA32$^{S4/S8}$ DNA damage repair nuclear foci following 2 Gy X-irradiation (1 h recovery) or 1 ng/ml gemcitabine (4 h incubation) as indicated.

FIGS. 8A-F: FIG. 8A, PD-L1 does not promote Raptor or Rheb. FIG. 8B, PD-L1 is required for mTORC1 association with lysosomes. FIG. 8C, PD-L1 is required for LAMTOR1 and LAMTOR2 associations with mTORC1 (RAGULATOR). FIG. 8D, PD-L1 promotes LAMTOR expression by immunoblotting and anti-mTOR immunoprecipitated Lamtors in control ES2 cells as expected (showing Ragulator association with mTORC1) but immunoprecipitated Lamtors significantly less efficiently in PD-L1$^{KO}$ cells. FIG. 8E, (a, top left): Representative images of mTOR/LAMP1 colocalisation in control and PD-L1$^{KO}$ B16 cells by confocal microscopy (40×). (b, top right), Quantification of (a) from ≥10 regions of interest selected at random. Colocalisation analysis performed using 40× magnification z-stack images in Imaris Bitplane software, version 9.3.0. P value by unpaired t-test. (c, bottom left): Quantification of LAMTOR 1-3 expression by confocal imaging in control versus PD-L1$^{KO}$ B16 cells. (d, bottom right): Quantification of mTOR-LAMTOR1 and mTOR-LAMP1 in control and PD-L1$^{KO}$ cells. P value, unpaired t-test. FIG. 8F, LAMTOR1 knock-in (KI) restores mTORC1 association with lysosomes and expression of other Lamtors in PD-L1$^{KO}$ (Lamtor-deficient) tumor cells (ES2 human ovarian cancer cells). Colocalisation analysis performed using 40× magnification z-stack images in Imaris Bitplane software, version 9.3.0. P values by unpaired t-test. Immunoblots were performed as described with anti-Lamtor antibodies from reliable commercial sources.

FIG. 11A, Vectors used for subcellular or control total PD-L1 expression in cancer cells. FIG. 11B, Validation of correct subcellular location of PD-L1 in ES2 and B16 control and compartment-specific knock-in. Quantification of z-stack confocal images for PD-L1 fluorescence on cell surface and cytoplasm using Imaris Bitplane software. FIG. 11C, PD-L1$^{surf}$ co-localises with transmembrane (cell surface control) protein Na$^+$/K$^+$-ATPase confirming surface expression of PD-L1. FIG. 11D, PD-L1cyto (Alexa Fluor 488) does not co-localise with surface-bound Na$^+$/K$^+$-ATPase (Alexa Fluor 647), and neither does mTOR (Alexa Fluor 555) confirming non-surface PD-L1 expression with appropriate controls. FIG. 11E, PD-L1$^{total}$ showing PD-L1 localisation to both surface (Na$^+$/K$^+$-ATPase, red) and cytoplasm confirming the total PD-L1 re-knock-in control. Blue nuclear DAPI stain. FIG. 11F, B16 mouse melanoma cells and human ES2 ovarian cancer cells tested for PD-L1 expression by confocal imaging quantified in Imaris software as mean fluorescence intensity (MFI) demonstrating that PD-L1$^{surf}$, PD-L1$^{cyto}$ and PD-L1$^{total}$ re-express PD-L1 at the same levels in the same subcellular compartments as the parental cells.

FIG. 12A-B: PD-L1$^{cyto}$ and PD-L1$^{surf}$ mediate distinct cell signaling and functional outcomes. FIG. 12A, Two distinct clones each of PD-L1$^{cyto}$ and PD-L1$^{surf}$ ES2 cells were subjected to RNA-sequencing plus DAVID bioinformatics to detect mRNA expression differences shown as increases (red) or decreases (green) versus the control. Horizontal lines represent individual mRNAs for distinct gene products. Individual clone numbers are indicated at the bottom of the heat map. FIG. 12B, Control (ctrl), and indicated cells all derived from ES2 were subjected to atomic force microscopy. Each dot represents a single cell. Differences by unpaired t-test.

FIG. 13A, Imaging of colocalized mTORC1 associating with Ragulator shown by mTOR colocalization with LAMTOR1 and mTORC12 associating with lysosomes by showing association of mTOR with Lamp1 in PD-L1$^{cyto}$ but not PD-L1$^{surf}$ B16 cells. Quantification of colocalized mTOR association with lysosomes (LAMP1, LAMP2) shown below images. P values, unpaired t-test. FIG. 13B, Immunoblot of mTORC1 signals in ES2 cells based on subcellular PD-L1 localization.

FIG. 14A, PD-L1 isoform 2 does not improve mTORC1 association with lysosomes in ES2 cells by representative confocal imaging. FIG. 14B, Summary statistics for mTORC1 association with lysosomes in ES2 cells by Imaris imaging analyses of confocal images. P values, unpaired t-test.

FIG. 16A, Confocal images of mTOR/LAMTOR1, mTOR/LAMTOR2 or mTOR/LAMTOR3 (mTORC1/Ragulator) associations in human PD-1$^{KO}$ ES2 ovarian cancer cells with summary statistics of images by Imaris software to the right. FIG. 16B, Confocal images of mTOR/LAMP2 (mTORC1/lysosome) associations in human PD-1$^{KO}$ ES2 ovarian cancer cells with summary statistics of images and of mTOR/LAMP2 images by Imaris software to the right. FIG. 16C, immunoblot of mTORC1 signals in PD-1$^{KO}$ ES2 ovarian cancer cells.

FIG. 17A, Confocal images of LAMTOR1 and LAMTOR2 content in mouse PD-1$^{KO}$ B16 melanoma cells. FIG. 17B, Confocal images of mTOR/LAMP2 (mTORC1/lysosome) associations in mouse PD-1$^{KO}$ B16 melanoma cells. Summary statistics of images by Imaris software are below each image.

FIG. 18A, PD-1/PD-L1 colocalization by confocal imaging of human ES2 ovarian cancer cells or mouse B16 melanoma cells, with a representative image shown above and an enlargement of that B16 cell image shown below it. FIG. 18B, summary statistics of confocal images of B16 and ES2 cells for PD-1/PD-L1 co-localizations by Imaris software.

FIGS. 19A-C: Tumor cytoplasmic PD-L1 predicts reduced tumor infiltrating lymphocyte content and poor anti-PD-1 immune therapy response in ovarian cancer patients. Tumor biopsies from 3 responder (R) and 3 non-responder (NR) patients in a Phase II trial (ClinicalTrials.gov Identifier: NCT02853318). R, responder (>24 months to progress) NR, non-responder (<4 months to progress) FIG. 19A, Fold-change in cell prevalence at baseline versus on-treatment. FIG. 19B, Percent surface and cytoplasmic PD-L1 done using FIJI software at 0.325 µm/pixel resolution to map x-y coordinates through the focal plane. Total tumor PD-L1 by Nanostring GeoMx Spatial Imaging Platform using barcoded UV-photocleavable oligos mapped to x-y coordinates and signal assessed by barcoded oligo to obtain surface and cytoplasmic data. Mean of 3 regions of interest/patient assessed by 2-way ANOVA with Tukey's multiple comparisons test. FIG. 19C, Cytoplasmic/surface PD-L1 ratio negatively predicts αPD-1 response. T-test for panels A and C.

FIG. 20B, Intracellular PD-L1 has the same sequence as in FIG. 20A, but the N-terminal domain is unfolded and interacts with proteins distinctly and cannot engage PD-1 like extracellular PD-L1. Raptor only affects mTORC1 and is unaffected by PD-L1. Lamtors activate mTORC1 and affect nutrient sensing and ERK signals, among other possibilities unaffected by mTORC1 alone. Lamtors are controlled by cytoplasmic, not surface PD-L1.

FIGS. 21A-H: Tumor PD-L1 modulates ATM/ATR DNA damage pathways. FIG. 21A, Immunoblot of B16-F10 control (CTRL) versus CRISPR/Cas9 deleted (PD-L1$^{KO}$) B16 cells analyzed for total ATM, Chk2, γH2AX, and Vinculin loading control (VINC). FIG. 21B, Immunoblot interrogation of the ATR/Chk1 pathway in CTRL versus PD-L1$^{KO}$ B16-F10 analyzed for total ATR, p-ATR, total Chk1 and p-Chk1. FIG. 21C, Representative confocal images of nuclear DNA damage foci (γH2AX) in CTRL and PD-L1$^{KO}$ B16-F10 cells. FIG. 21D, Summary statistics of panel C imaging by quantifying average number of foci per nucleus.

Data presented as mean±SD and p-value calculated by unpaired t-test. FIG. 21E and FIG. 21F, Immunoblot interrogation for ATM/Chk2 and ATR/Chk1 DDR signaling pathways in CTRL versus PD-L1$^{KO}$ RT4 cells 24 hours post gemcitabine (Gem) exposure (10 ng/ml) or vehicle (Veh). FIG. 21G, Immunoblot showing ATM and Chk2 content in cytoplasmic (GAPDH) and nuclear (Histone H3) fractions of indicated cell lines. FIG. 21H, DNA repair kinetics assessed by Western blot analysis of CTRL and PD-L1$^{KO}$ RT4 cells for γH2AX at indicated recovery time periods following X-irradiation (2 Gy). M, medium control. (H) ours, times after irradiation.

FIGS. 22A-O: Tumor PD-L1 suppresses selective ATR/Chk1 inhibitor synthetic lethality, independent of immunity. Cell viability (MTT assay) of CTRL and PD-L1$^{KO}$ RT4 cells treated in vitro with increasing concentrations of FIG. 22A, LY2603618 (Chk1 inhibitor) FIG. 22B, AZD6738 (ATR inhibitor) FIG. 22C, AZD0156 (ATM inhibitor) for 5 days at indicated doses. Viability normalized to vehicle controls. (mean+SEM, n=6 replicates, ***, P<0.001, unpaired t-test). FIGS. 22D-E, Cell viability as in FIGS. 22A-C of CTRL versus PD-L1$^{lo}$ 4T1 (shRNA) and CTRL versus PD-L1$^{KO}$ ID8agg cells treated with increasing concentrations of LY2603618 (FIGS. 22D-E) or AZD6738 (FIG. 22F). FIGS. 22H-I, Representative colony survival assays of indicated cell lines using crystal violet. RT4 in FIG. 22H and 4T1 in FIG. 22I after genetic PD-L1 targeting and treated with indicated concentrations of LY2603618. FIGS. 22I-K, Tumor growth curves in NSG mice (n=10 tumors/group) challenged with CTRL or PD-L1$^{lo}$ 4T1 cells and treated with rabusertib (Chk1i, LY2603618) at 1 mg/kg on days 3, 10 and 17. P values, two-way ANOVA. Tumor weights of CTRL versus PD-L1$^{lo}$ tumors at endpoint. P values, unpaired t-test. Chk2 expression plasmid or the corresponding empty vector control plasmid was transfected into PD-L1$^{lo}$ 4T1 (Chk2KI) or I. PD-L1$^{KO}$ RT4 cells and viability assessed 5 days post (+) Chk1i (LY2603618, 2.5 μM) or vehicle (-) control. Data, mean+SD normalized to vehicle controls of 3 independent biological replicates. P values, unpaired t-test. FIGS. 22N-O, Corresponding immunoblots confirming Chk2 re-expression and reversal of Chk1i induced DNA damage (γH2AX) from transfection experiments in FIGS. 22L-M.

FIGS. 23A-H. Intracellular PD-L1 is sufficient to restore Chk2 expression. FIG. 23A, Immunoblots of PD-L1$^{KO}$ or PD-1$^{KO}$ B16-F10 versus control (CTRL) cells for PD-1, PD-L1, ATM, Chk2, γH2AX. FIGS. 23B-C. Schematic representation of surface expressed PD-L1 (PD-L1$^{surf}$) or intracellular PD-L1 (PD-L1$^{cyto}$) and validation of constructs by immunoblotting of subcellular fractions and confocal imaging (see FIGS. 32C-D, and materials and methods). FIG. 23D, Heat map profile of transcripts by hierarchical gene clustering from RNA-seq data and FIG. 23E, summary GSEA signature of pathways in PD-L1$^{surf}$ or PD-L1$^{cyto}$ re-expressed in PD-L1$^{KO}$ B16-F10 cells. FIGS. 23F-G, GSEA signature of indicated pathways comparing PD-L1$^{surf}$ versus PD-L1$^{cyto}$ B16-F10 cells (2 biologically independent sequenced samples (n=3) per group). FIG. 23H, Immunoblots of CTRL, PD-L1$^{KO}$, PD-L1$^{surf}$, and PD-L1$^{cyto}$ B16-F10 cells probed for PD-L1, ATM, Chk2, Vimentin, γH2AX, and loading control vinculin (VINC).

FIGS. 24A-G: PD-L1 promotes Chk2 protein stability and prevents Chk2 mediated lysosomal degradation. FIG. 24A. Effect of PD-L1 knockout (PD-L1$^{KO}$) by CRISPR/Cas9 on relative mRNA levels of indicated genes compared to CTRL replete (CTRL) B16-F10 cells represented by volcano plot of RNA-seq data. FIG. 24B, qRT-PCR analysis of relative Chek2 mRNA levels, normalized to GAPDH in CTRL versus PD-L1$^{KO}$ B16-F10 cells treated with vehicle (veh) or Chk1 inhibitor. Data presented as mean+SD and p-value calculated by unpaired t-test (n=3 biological replicates). FIG. 24C, Immunoblot (IB) comparing CTRL, PD-L1$^{KO}$, and Raptor knockdown (Raptor$^{lo}$) B16-F10 cells analyzed for PD-L1, Raptor, Chk2, p-S6, total-S6, and loading vinculin control (VINC). FIG. 24D, CTRL or PD-L1$^{KO}$ B16-F10 cells were cultured in the presence of cycloheximide (CHX) for the indicated time periods. IB analysis was performed for ATM, Chk2, and VINC. FIG. 24E, Summary graph of representative IB depicted in panel FIG. 24D of total Chk2 protein levels in CTRL or PD-L1$^{KO}$ B16-F10 cells quantified using ImageJ. Chk2 bands were first normalized to their respective VINC bands then normalized to vehicle treated control.

FIGS. 25A-D. Intracellular PD-L1 promotion of Chk2 is independent of its C-terminal tail. FIG. 25A, Immunoblot (IB) and FIG. 25B, Confocal microscopy analysis of PD-L1-RFP fusion mutants re-expressed in PD-L1$^{KO}$ B16-F10 cells utilizing indicated IB antibodies (* denotes expected sizes of PD-L1 mutants). FIG. 25C, IB analysis of Chk2 in indicated PD-L1-RFP mutants re-expressed in PD-L1$^{KO}$ cells. FIG. 25D, Interaction of PD-L1 and Chk2 under basal (veh) and DNA damage cell stress conditions with Chk1i (24 hours) demonstrated by co-immunoprecipitation (Co-IP).

FIGS. 26A-H: De novo PD-L1$^{KO}$ tumors phenocopy important aspects of genetic PD-L1 depletion in established tumors. FIG. 26A, Melanoma-free survival of melanocyte specific CD274$^{fl,fl}$ TpN$^{61R}$ (KO) versus littermate (WT) autochthonous mice under conditions shown. FIG. 26B, Validation of PD-L1 expression by immunoblot (IB) of melanoma cells derived from UV induced (4.5 Kj/m$^2$) WT (CD274$^{+/+}$) or melanocyte specific CD274$^{KO}$ (CD274$^{-/-}$) mice±in vitro interferon (IFN)-γ treatment. Viability curves of CD274$^{+/+}$ versus CD274$^{-/-}$ cells treated with the selective Chk1 inhibitors FIG. 26C, prexasertib (LY2603628) or FIG. 26D, rabusertib (LY2603618) in vitro at indicated concentrations. FIG. 26E, IB analysis of PD-L1, ATM, Chk2, and γH2AX of vehicle or rabusertib-treated CD274$^{+/+}$ and CD274$^{-/-}$ cell lines. FIGS. 26F-H, Tumor growth curves in WT C57BL/6J mice (n=10 tumors/group) challenged with UV induced TpN$^{61R}$ derived CD274$^{+/+}$ or CD274$^{-/-}$ melanoma cells and treated with rabusertib (Chk1i, LY2603618) on the indicated treatment schedule. P values, two-way ANOVA.

FIGS. 27A-H: Anti-PD-L1 antibodies mimic genetic PD-L1 depletion to impair tumor cell-intrinsic DDR signals and promote sensitivity to Chk1 inhibition in vitro and in vivo. Cell viability of FIG. 27A, CTRL and FIG. 27B, PD-L1$^{KO}$RT4 cells treated with LY2603618 (Chk1 inhibitor) as shown plus IgG1 isotype or atezolizumab (atezo, 3 μg/ml) for 72 hours in vitro. Mean+SEM, n=6 replicates, ***, P<0.001, unpaired t-test. FIG. 27C, Immunoblot (IB) analysis of ATM, Chk2, γH2AX and vinculin (VINC) of RT4 cells treated in vitro with isotype, atezolizumab, Chk1i, or their combination. FIG. 27D, Viability of 4T1 cells as in panel A substituting anti-murine PD-L1 and isotype controls. FIG. 27E, IB of 4T1 as in panel FIG. 27C. FIG. 27F, Tumor curves of NSG mice (n=10 tumors/group) challenged with 4T1 tumor cells and treated with Chk1i±αPD-L1. FIG. 27G, Tumor curves and FIG. 27H, tumor weights in WT C57BL/6J mice challenged and treated as in panel FIG. 27F. P values, two-way ANOVA.

FIGS. 31A-F: PD-L1 depletion results in cell-cycle checkpoint defects.

FIGS. 32A-D: PD-L1 dependent DDR effects are PD-1 independent.

FIGS. 33A-D: FIG. 33A, Flow cytometry analysis of PD-L1 VC, vehicle control.

MFI, mean fluorescence intensity. FIG. 33B, Western blots for PD-L1 expression in human and mice ovarian cancer cells which were treated with (+) or without (−) chlorambucil for 48 hours. Vinculin, loading control. FIG. 33C, WT mice were challenged with ID8agg, treated with chlorambucil (1 mg/kg as described in methods) and sacrificed 4 weeks after tumor challenge.

Tumor and ascites were collected for flow cytometry analyses. Summary graph of CD45-PD-L1 cell percentage and MFI. FIG. 33D, PD-1 and B2M expression on OVCAR5 (human ovarian) cells treated with (+) or without (−) chlorambucil for 48 hours.

FIGS. 34A-D: FIG. 34A, Cells cultured in vitro with chlorambucil at indicated concentrations and counts determined on Vi-Cell. p-value, unpaired t-test. VC, vehicle control. FIG. 34B, Annexin V-FITC/PI (AV/PI) dual staining assay. Upper left, necrotic cells). Lower left, live cells. Lower right, early apoptotic cells and upper right, late apoptotic cells. ID8agg (CAMB 5 μM) and B16 (CAMB 10 μM) cells were treated for 48 hours. FIG. 34C, CAMB-treated ID8agg and B16 cells stained with an isotype control or an anti-calreticulin (CRT) antibody followed by immunofluorescence cytometry. FIG. 34D, Tumor cells were treated with the indicated concentrations with CAMB 48 h. Cell viability was detected by CCK-8 assay and relative cell viability ratio were compared between WT cells and PD-L1KO or PD-L1lo cells at different concentration point.

FIGS. 35A-G: FIG. 35A, ID8agg tumor bioluminescence after challenge in WT mice treated with chlorambucil (2 mg/kg) as described through day 25. P-value, two-way ANOVA. FIGS. 35B-C, Kaplan-Maier plot of survival in WT or NSG mice (P value from log-rank test). FIG. 35D, WT mice challenged with PD-L1$^{lo}$ ID8agg cells and treated as in FIG. 35A. Mice body weight measured weekly. P-value, two-way ANOVA. At the end of experiment, mice were sacrificed and tumor weights measured (right). Each symbol is an individual tumor. P-value, unpaired t-test. FIG. 35E, WT mice challenged with B16 cells and treated with chlorambucil 3 mg/kg as described, with the last treatment on day 18. p-value, two-way ANOVA. Kaplan-Maier plot of survival (right panel). FIG. 35F, NSG mice challenged with B16 cells and treated with chlorambucil as for WT mice. Kaplan-Maier plot of survival. FIG. 35G, WT mice challenged with PD-L1$^{KO}$ B16 cells and treated with chlorambucil as for control B16. FIG. 35H, Tumor growth fold-change compared in CTRL versus PD-L1$^{KO}$ B16 tumors. P-value, unpaired t-test. I. NSG mice challenged with PD-L1$^{KO}$ B16 cells and treated with chlorambucil as in FIG. 35I, Kaplan-Maier plot of survival.

FIGS. 36A-F: Chlorambucil improves αPD-L1 treatment efficacy in vivo: FIG. 36A, ID8agg tumor bioluminescence after challenge in wild type mice and treatment with chlorambucil (1 mg/kg) as described±αPD-L1. αPD-L1 100 μg/mouse on days 7, 10, 13 and 16. P-value, two-way ANOVA and survival (right panel). FIG. 36B, Untreated control or chlorambucil-treated PD-L1$^{KO}$ ID8agg and PD-L1KO B16 cells for CRT expression after chlorambucil exposure. FIG. 36C, WT mice challenged with PD-L1$^{lo}$ ID8agg and treated with chlorambucil (2 mg/kg)±αPD-L1 as in A. FIG. 36D, Survivors were rechallenged with control ID8agg cells. Naïve mice were challenged with challenged ID8agg. Kaplan-Maier plot of survival. FIG. 36E. WT mice were challenged with PD-L1$^{KO}$ B16 and treated with chlorambucil (1.5 mg/kg)±αPD-L1 both as for CTRL B16. Tumor growth were measured and survival (FIG. 36F) tested as before.

FIGS. 37A-B: Chlorambucil plus αPD-L1 promotes IFN-γ production in ID8agg tumors. FIG. 37A, Flow cytometric analysis of CD8$^+$ T cells and IFNγ production in ID8agg tumors treated with CAMB±anti-PD-L1. P-value, unpaired t-test. FIG. 37B, Representative flow plots showing the abundance of memory and naïve CD8$^+$ T cells. P-value, unpaired t-test.

FIGS. 38A-C: CAMB plus αPD-L1 enhances anti-tumor immune cells population in PD-L1$^{KO}$ B16 tumor. FIG. 38A, Summary graph of CD8+ T cells population and exhausted PD1+CD8+ T cell population in PD-L1KO B16 tumor treated with isotype or combo. P-value, unpaired t-test. FIG. 38B, Summary graph of NK cells population, exhausted NK cell population and (FIG. 38C) myeloid cell population in PD-L1KO B16 tumor treated with isotype or combo. P-value, unpaired t-test.

FIGS. 39A-C: CAMB reduces PD-L1 through ubiquitination. FIG. 39A, RT-qPCR for PD-L1 mRNA in OVCAR5 and ID8agg cells treated with (+) or without (−) chlorambucil for 48 hours. (n=4). FIG. 39B, Western blot for PD-L1 protein in OVCAR5 cells with (+) or without (−) MG132 for 6 or 20 hours. (upper panel). PD-L1 expression in OVCAR5 cells treated with chlorambucil 48 hours and/or MG132 for 6 hours (lower panel). FIG. 39C, Ubiquitinated PD-L1 was immunoprecipitated (IP) and subjected to Western blot analysis with anti-ubiquitin (Ub) antibody. Cells were treated with chlorambucil for indicated times prior to ubiquitination analysis.

FIGS. 40A-C: CAMB suppresses mTORC1 signals and reduces TIC numbers. FIG. 40A, Western blots for proteins in the mTORC1 pathway. Cells were treated with chlorambucil as indicated concentration for 48 hours. FIG. 40B, Western blot for LC3I/II to assess autophagy in cell lysates treated±chlorambucil at indicated concentrations. FIG. 40C, Percent of ALDH$^{hi}$ TIC by flow cytometry of ES2 cells cultured±chlorambucil. Percent CD44$^+$CD24$^+$ ID8agg TIC and CD44$^+$CD133$^+$CD24$^+$ B16 TIC detected by flow cytometry.

FIGS. 44A-B: Cefepime depletes PD-L1 and Chk2 and increases DNA damage (gH2AX).

FIGS. 45A-B: Effect of erlotinib, olaparib, combination, or vehicle on MB49 cells.

FIG. 46A, Olaparib activity is seen with erlotinib. FIG. 46B, cefepime improves rabusertib efficacy.

FIG. 47A, Ceftazidime induces synthetic lethality in RT4 and ID8agg cells. FIG. 47B, Ceftazidime synthetic lethality is PD-L1 dependent. FIG. 47C, Ceftriaxone and cefazolin are not as effective at inducing Chk1i synthetic lethality in RT4 cells. FIG. 47D, Penicillin G and meropenem do not induce synthetic lethality with Chk1i in RT4.

DESCRIPTION OF ILLUSTRATIVE EMBODIMENTS

Figure 8A:
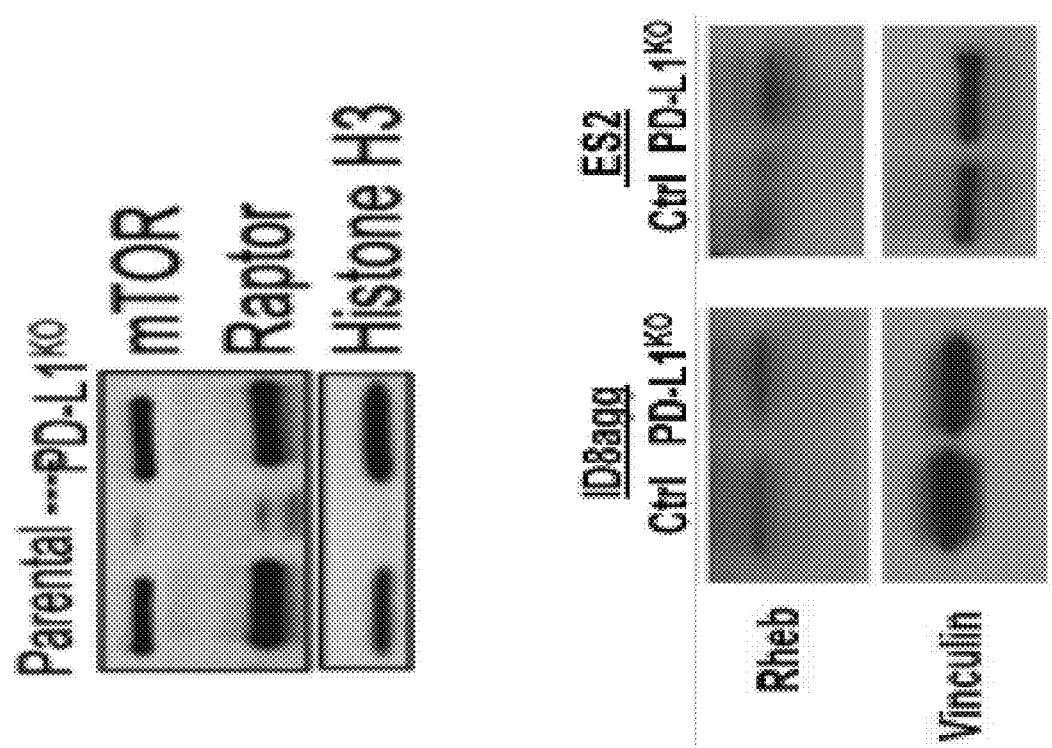
Figure 8B:
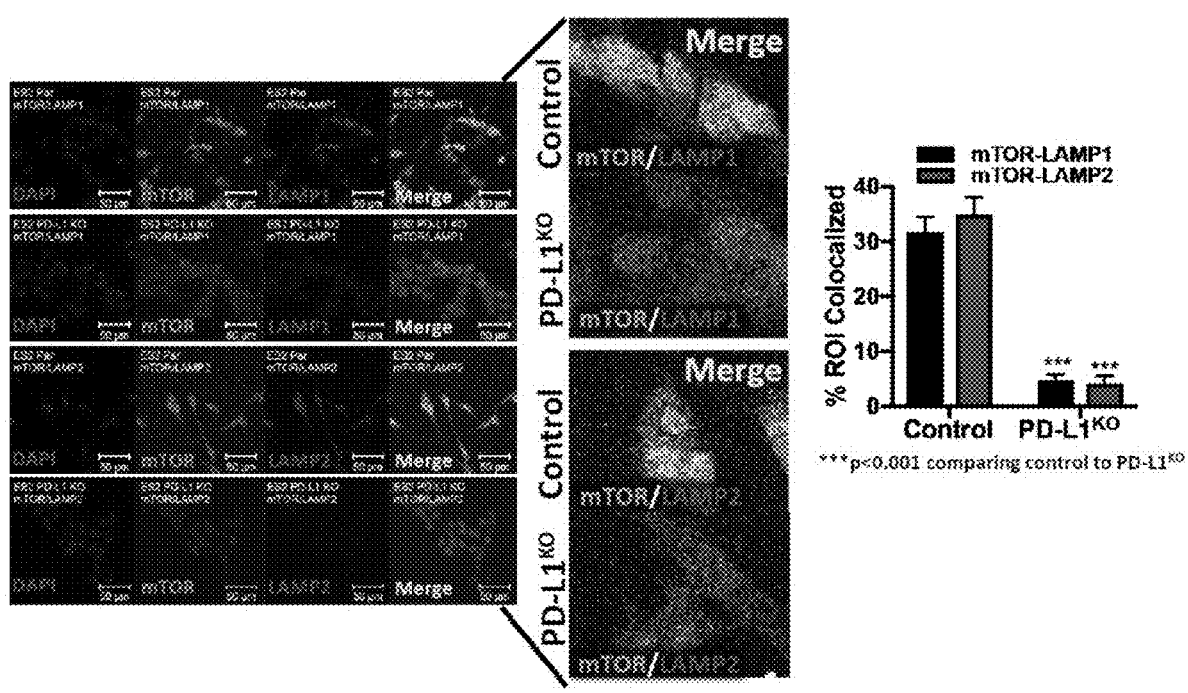

I. Methods of Detecting or Measuring Cytoplasmic PD-L1 or Surface PD-L1

A variety of methods can be used to detect or measure cytoplasmic PD-L1 and/or surface-expressed PD-L1 ("surface PD-L1") in a cell (e.g., a cancerous cell) or a tissue sample (e.g., a tumor biopsy). In some embodiments, cytoplasmic PD-L1 and surface PD-L1 are simultaneously measured in the cell or tissue sample. In some embodiments, only cytoplasmic PD-L1 is measured in a cancer.

Programmed death-ligand 1 (PD-L1) is expressed by many human cancers. Binding of PD-L1 to its receptor PD-1 on activated T cells can inhibit anti-tumor immunity by counteracting T cell-activating signals. Tumor-cell intrinsic PD-L1 signaling effects can include promoting tumor initiating cells and mTORC1, and suppressing autophagy (Clark et al., 2016; Gupta et al., 2016). Tumor-intrinsic PD-L1 can inhibit autophagy, alter interferon-β signaling, and mediate resistance to cytotoxicity of interferon-gamma, radiation, or chemotherapy (Wu et al., 2016; Tu et al., 2019; Escors; 2018). While the mechanisms of PD-L1 actions in cancers are not fully understood, cell-surface expression of PD-L1 can be targeted by some cancer immunotherapies, such as an antibody that binds the cell-surface PD-L1.

In some embodiments, an immunohistochemistry or antibody-based method is coupled with an imaging technique to detect or measure cytoplasmic PD-L1 and/or surface PD-L1 in cells or a tissue sample. The imaging techniques that can be used include, e.g., light microscopy, fluorescence microscopy, and confocal microscopy. In some preferred embodiments, digital imaging analytic software is used in combination with the imaging technique. The imaging technique may utilize an anti-PD-L1 antibody labelled with a fluorescent tag plus a barcoded oligonucleotide, or a labeled anti-PD-L1 antibody (e.g., labeled with a fluorescent or heavy metal tag). It is anticipated that mass spectroscopy, cell fractionation and immunological detection can be used to identify cytoplasmic PD-L1 and/or surface PD-L1 in a cell. The ratio of tumor cytoplasmic PD-L1 to surface PD-L1 can be calculated using data collected via any of the above-mentioned approaches. In some embodiments, the ratio of cytoplasmic PD-L1 to surface PD-L1 in a cancerous cells to tissues can be repeatedly measured over a period of time (e.g., before, during, and/or after administration of an anti-cancer treatment to a mammalian subject or human patient), and the measurements can be statistically analyzed (e.g., using a paired t test, an ANOVA, or a $X^2$ test), if desired.

Programmed death (PD)-1 and PD ligand-1 (PD-L1) are expressed by some cancers, and cancer immunotherapies with antibodies blocking programmed death (PD)-1 or PD ligand-1 (PD-L1) are proposed to work principally by inhibiting tumor surface-expressed PD-L1 from engaging negative T cell PD-1 receptors, but additional mechanisms exist (Topalian et al., 2012; Clark et al., 2016; Gupta et al., 2016; Wu et al., 2018). We previously reported that tumor PD-L1 activates tumor mammalian target of rapamycin complex 1 (mTORC1) (Tu et al., 2019). PD-L1 may mediate diverse tumor-intrinsic functions that increase cancer virulence, including promoting DNA damage repair (DDR).

In some embodiments, cytoplasmic PD-L1 can be measured in a tissue sample using an anti-PD-L1 antibody labelled with a barcoded oligonucleotide, fluorescent tag, or heavy metal. For example, in some embodiments, the following methods can be used to measure cytoplasmic PD-L1 and surface PD-L1. Tumor biopsies can be formalin-fixed and embedded in paraffin. The paraffin-embedded tumors can then be cut into ~4-5 micron slices and stained with specific antibodies coupled to barcoded UV-photocleavable oligonucleotides (e.g., available from NanoString, Seattle, WA) and fluorescent tags. Percent surface and cytoplasmic PD-L1 can be determined by assessing oligonucleotide location, e.g., using FIJI software at about 0.325 µm/pixel resolution to map x-y coordinates through the focal plane in selected regions of interest. Total tumor PD-L1 can be determined, e.g., using Nanostring GeoMx™ Spatial Imaging Platform using mapped to x-y coordinates and signal from barcoded oligonucleotides to obtain surface PD-L1 and cytoplasmic PD-L1 data.

In some embodiments, cytoplasmic PD-L1 and/or surface PD-L1 can be detected or measured in a tissue sample or cell using an immunological or antibody-based detection method. For example, in some embodiments, immunohistochemistry or confocal microscopy can be used to detect or measure intracellular PD-L1. Cell-fractionation may be combined with an immunological detection method such as a Western blot. Other techniques that may be used include cell fractionation followed by mass spectrometry or immunoprecipitation with an anti-PD-L1 antibody from cell fractions followed by detection with mass spectrometry or an imaging or immunological technique, e.g., as described above.

In some embodiments, RT-qPCR or oligonucleotides capable of binding cd274 messenger RNA can estimate the PD-L1 protein content in subcellular compartments in which cd274 messenger RNA is known to correlate with PD-L1 protein content. The oligonucleotides can be coupled to heavy metals or fluorescent dyes or other tags for visualization using approaches as described for similarly tagged antibodies described above.

Detection or measurement of surface PD-L1 and/or cytoplasmic PD-L1 may involve comparison with a selected reference. In some preferred embodiments, the ratio of surface PD-L1 to cytoplasmic PD-L1 is generated by comparing the PD-L1 content in the cytoplasm with the PD-L1 on the surface of a cell. In this way, the cytoplasmic PD-L1 to surface PD-L1 ratios (surface:cytoplasmic PD-L1 ratios) can be generated for many cells across a tissue sample, e.g., to generate an average or median ratio. Surface:cytoplasmic PD-L1 ratios can be calculated in tumor biopsies or cancerous cells at multiple timepoints, e.g., before and after an anti-cancer treatment.

In some embodiments, the surface:cytoplasmic PD-L1 ratio in a cancer is monitored over a period of time and may be helpful for determining if the cancer is responding to the anti-cancer treatment.

II. Methods of Detecting or Measuring Lamtor Proteins

A variety of methods may be used to detect or measure a Lamtor protein (also refered to as a Late Endosomal/Lysosomal Adaptor, MAPK And MTOR Activator) in a cancer. As shown in the below examples, the inventors have observed that that tumor Lamtor expression can predict survival in cancers, including melanoma and ovarian cancers.

Lamtor proteins include LAMTOR1, LAMTOR2, LAMTOR3, LAMTOR4, and LAMTOR5. Lamtors assemble into a Ragulator complex that activates mTORC1, including in cancer cells, under some conditions. Lamtors in urine exosomes have been associated with some bladder cancers (Overbye et al., 2015), but the function of Lamtors in cancer is poorly understood, and to the knowledge of the inventors this protein has not previously been associated with patient outcomes or survival.

In some embodiments, a Lamtor protein (e.g., LAMTOR1, LAMTOR2, LAMTOR3, LAMTOR4, or LAMTOR5) can be detected or measured in a tissue sample or cells, such as a tumor biopsy or cancerous cells, using an immunological or antibody-based detection method. For example, in some embodiments, immunohistochemistry or confocal microscopy can be used to detect or measure the Lamtor protein. In some embodiments, an immunological detection method such as a Western blot can be used. Other techniques that may be used include cell fractionation followed by mass spectrometry or immunoprecipitation with an anti-PD-L1 antibody from cell fractions followed by detection with mass spectrometry or an imaging or immunological technique. In some embodiments, real-time PCR (qPCR) can be used to detect the Lamtor protein in the tissue sample or cells.

III. DDR Inhibitors

In some aspects, methods are provided herein for predicting cancer responses to, and/or patient outcomes associated with, treatment with one or more inhibitors of the DNA damage response (DDR) process, including DDR kinases. Patient therapies can thus be personalized by identifying cancers in patients that are sensitive to or resistant to treatment with a DDR inhibitor (DDRi).

DDR networks are involved with detecting and repairing DNA lesions. DDR networks can interact in complex ways with a variety of other cellular processes, including DNA replication and transcriptional machinery (Rundle et al. 2017), cell cycle control molecular networks (Otto et al., 2017), molecular pathways that control energy metabolism (Otto et al., 2017), programmed cell death (Shiloh, et al. 2013), and systems that control innate immunity (Bhattacharya et al., 2017). These interactions with ostensibly distinct molecular processes ensure, for example, that the cell cycle is stalled to allow DNA repair (Otto et al., 2017) or that cells with excessive levels of DNA damage are removed from the population.

DDR can influence the real-world outcome for people with cancer. While defects in the DDR can drive the development of cancer, DDR can also result in cancer-specific vulnerabilities that can influence therapy strategies. For example, many of the chemotherapy or radiotherapy treatment regimens commonly used in the treatment of cancer generate DNA lesions, including abnormal covalent bonds ("cross links") within the double helix. In tumor cells with particular DDR defects, these DNA lesions are ineffectively recognized and/or repaired, which often leads to cytotoxicity; conversely most normal cells, which in principle have a better capacity to process DNA damage, are relatively unharmed. DNA damaging chemotherapies and/or radiotherapies can exploit DDR defects in some tumor cells and can be therapeutic.

DDR inhibitors (DDRi) include several classes of compounds. The first class of targeted DDR inhibitors to be approved by the FDA for use in the treatment of cancer are the PARP inhibitors, including rucaprib, olaparib, and niraparib. Although it is anticipated that a wide variety of PARP inhibitors may be used (e.g., Lord and Ashworth, 2017.), in some preferred embodiments that DDRi is an inhibitor of kinases involved in the DDR. The DDRi may be an inhibitor of the DDR kinase: Ataxia telangiectasia mutated (ATM), Ataxia telangiectasia and Rad3-related protein (ATR), DNA Dependent Protein Kinase (DNA-PK) (such as any of the phosphatidyl-inositol kinase-like kinase (PIKK) enzymes), CHK1, CHK2, or WEE1. Inhibitors of PARP (PARPi) or inhibitors of CHK1 (Chk1i) are used in some embodiments. Exemplary DDR kinase inhibitors and therapeutic combinations are provided in Table 1.

TABLE 1

DDR kinase inhibitors and combinations

| Drug target | Inhibitor | Combination |
|---|---|---|
| ATM | AZD0156 | +olaparib |
|  | KKU-55933 | +IR or radiomimetic |
|  |  | +topoisomerase I poisons |
| ATR | VE-821 | +cisplatin |
|  | AZD6738 | +carboplatin |
|  |  | +olaparib |
|  |  | +anti- PD-L1 antibody (MEDI4736) |
|  | AZD6738 and VX970 | +Standard chemotherapy |
|  | VX970 | +cisplatin |
|  |  | +olaparib |
| DNA-PK | VX-984 | +doxorubicin |
| CHK1 | MK8776 (SCH900776), LY2603618, CCT245737, GDC-0575 | +Standard chemotherapy +WEE1 inhibitor |
| CHK2 | PV1019 | +topotecan |
|  |  | +camptothecin |
|  |  | +IR |
|  | CCT241533 | +PARP inhibitors |
| CHK1/2 | AZD7762 | +irinotecan |
|  |  | +gemcitabine |
| WEE1 | AZD1775 | +CHK1 inhibition |
|  |  | +cisplatin |
|  |  | +cytarabine |
|  |  | +panobinostat |
| PARPi | rucaprib, olaparib, niraparib rucaprib |  |

IV. Additional Modulators of PD1/PD-L1 Intracellular Signaling

Additional compounds have been identified herein as modulators of PD-L1. These compounds may thus be administered to a subject to treat a cancer (e.g., a melanoma, ovarian cancer, etc.). For example, in some embodiments, the modulator of PD-L1 may be administered to a mammalian subject such as a human patient in order to reduce intracellular signaling of PD1 and/or PD-L1. In some embodiments, the cancer expresses increased PD1 and/or PD-L1 relative to healthy tissue. In some embodiments, the cancer has increased intracellular signaling of PD1 and/or increased intracellular signaling of PD-L1 relative to healthy tissue. In some embodiments, the modulator of PD1/PD-L1 is PMEG or chlorambucil. As shown in the below examples, both PMEG and chlorambucil reduced surface tumor PD-L1 about 30-70% over 2-3 days, depending on the cell type, in a variety of human and mouse tumor lines with little effect on cell viability. Both agents were observed to suppress mTORC1 signals and promote autophagy, similar to what the inventors observed in genetic PD-L 1 depletion. Without wishing to be bound by any theory, these results support the idea that that drug-mediated PD-L 1 depletion may phenocopy or produce results similar to or consistent with genetic PD-L 1 depletion.

In some embodiments, the modulator of PD1/PD-L1 is bicalutamide. Bicalutamide is an anti-androgen compound. Methods of synthesis of bicalutamide are known, e.g., as described in U.S. Pat. No. 4,636,505. In some embodiments, bicalutamide is administered to treat a cancer in a mammalian patient, wherein the cancer is not a prostate cancer. It is anticipated that in some embodiments a derivative of bicalutamide, such as enzalutamide, apalutamide, or an arylpropionamide, can be used to achieve a similar effect as bicalutamide as described herein (e.g., to reduce PD1/PD-L1 expression or intracellular signaling in a cancer). Bicalutamide has the structure:

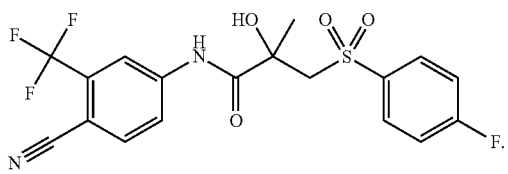 [SMILES: CC(O)(CS(=O)(=O)c1ccc(F)cc1)C(=O)Nc1ccc(C#N)c(C(F)(F)F)c1]

A variety of dosages of bicalutamide may be administered to the subject, e.g., about 50-150, 50, 75, 100, 125, or 150 mg by mouth once daily, or any range derivable therein.

In some embodiments, the modulator of PD1/PD-L1 is PMEG. PMEG (9-(2-phosphonylmethoxyethyl) guanine). PMEG is described, e.g., in U.S. Pat. No. 5,869,467. Although it is anticipated that PMEG may be used to treat cancers including melanomas, in some embodiments the cancer is not a melanoma. PMEG has been observed to exhibit antiviral properties (Ho et al., 1992). PMEG has the structure:

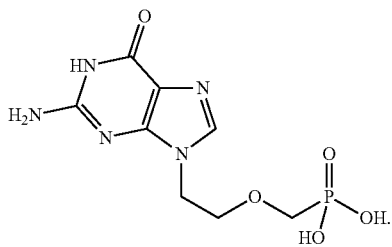 [SMILES: Nc1nc2c(ncn2CCOCP(=O)(O)O)c(=O)[nH]1]

A variety of dosages of PMEG may be administered to the subject, e.g., about 0.5-10, 1-10, 0.5, 1, 2, 3, 4, 5, 6, 7, 8, 9, 10, mg/kg/day, or any range derivable therein. The administration may be, e.g., oral, intravenous, intratumoral, via injection, or via intraperitoneala dministration.

In some embodiments, the modulator of PD1/PDL1 is chlorambucil. A variety of dosages of chlorambucil may be administered to a patient, such as about 1-15, 2-10, 1, 2, 3, 4, 5, 6, 7, 8, 9, 10, 11, 12, 13, 14, or 15 mg/m²/d, or any range derivable therein. In some embodiments, about 10 mg/m²/d is administered to the patient. Chlorambucil has the structure:

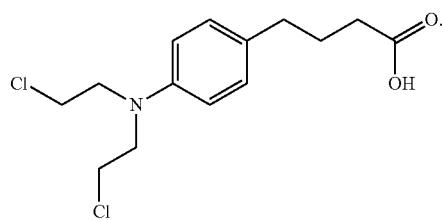 [SMILES: O=C(O)CCCc1ccc(N(CCCl)CCCl)cc1]

In some aspects, the modulator of PD1/PDL1 is a beta-lactam antibiotic. As shown in the below examples, beta-lactam antibiotics such as cefepime or ceftazidime can be used to treat a cancer, and depletion of PD-L1 in cells was observed. It is anticipated that a variety of beta-lactam antibiotics may be used. In some embodiments, the beta-lactam antibiotic is a penam, carbapenem, an oxapenam, a penem, a carbapenem, a monobactam, a cephem, a carbacephem, or an oxacephem. A variety of cephems may be used such as e.g., cefazolin, cephalexin, cephalosporin, cephalothin, cefapirin, cefaclor, cefamandole, cefuroxime, cefotetan, cefoxitin, cefixime, cefotaxime, cefpodoxime, ceftazidime, ceftriaxone, cefdinir, cefepime, cefpirome, and/or ceftaroline. In some embodiments, the In some embodiments, about 10-90, 20-80, 10, 20, 30, 40, 50, 60, 70, 80, 90, 100 mg per kg per day, or any range derivable therein, can be administered to a mammalian subject such as a human patient to treat the cancer. As shown in the below examples, data is provided showing that ceftazidime and/or cefepime can deplete PD-L1 and induce Chk1i synthetic lethality.

V. Cancers

Detection of cytoplasmic PD-L1 in a cancer (e.g., alone or in comparison to surface PD-L1) can be performed to diagnose or treat a cancer, e.g., to personalize a therapy, to predict survival, and/or to predict treatment response to a drug such as a DDRi. The cancer may express cytoplasmic PD-L1 and/or cell surface PD-L1. In some embodiments, the cancer is a gastric cancer, hepatocellular carcinoma, renal cell carcinoma, esophageal cancer, pancreatic cancer, ovarian cancer, bladder cancer, lung cancer, colorectal cancer, melanoma, breast cancer, or Merkel cell carcinoma, and these cancers may express PD-L1 (Wang et al., 2016). As described herein, increased cytoplasmic PD-L1 (e.g., either total increase or an increase relative to surface PD-L1 content in a tumor) can indicate decreased survival and increased resistance to a DDR inhibitor, such as a CHK1i or a PARPi. Increased cytoplasmic PD-L1 (e.g., either total increase or an increase relative to surface PD-L1 content in a tumor) can indicate resistance to an immunotherapy such as anti-PD-1, a cytotoxic agent such as cyclophosphamide or an anti-angiogenesis agent such as bevacizumab.

It is anticipated that the methods provided herein can be used to test a variety of cancers for expression of cytoplasmic PD-L1 (e.g., measuring both surface and cytoplasmic PD-L1 in the cancer, or determining the ratio of surface:cytoplasmic PD-L1). In some embodiments, the cancers include but are not limited to cells from the bladder, blood, bone, bone marrow, brain, breast, colon, esophagus, stomach, intestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; non-encapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease of breast, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; Sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Tumor Cell-Intrinsic PD-L1 Signals Promote Resistance to Chk1 or PARP Inhibitors by Modulating DNA Damage Responses As described below, PD-L1-expressing tumor cells were depleted of PD-L1 by genetic means or using shRNA.
Tumor-Intrinsic PD-L1 Promotes DDR Signaling in RT4 Human Bladder Cancer Cells after Gemcitabine-Induced DNA Damage Tumor-intrinsic PD-L1 alters sensitivity to DNA damaging agents through several distinct mechanisms (Clark et al., 2016; Gato-Canas et al., 2017; He et al., 2005). Experiments were performed to assess whether tumor-intrinsic PD-L1 specifically altered the DDR in response to gemcitabine, a DNA damaging chemotherapy agent that induces replication fork stalling and collapse (Clark et al., 2017). PD-L1 knockout (PD-L1$^{KO}$) RT4 and ID8agg cells were 2-fold and 29-fold more sensitive to gemcitabine versus control cells, respectively, in vitro (FIG. 1A, FIG. 6A). To assess the impact of gemcitabine on DNA damage, phosphorylated gamma-H2AX ($\gamma$H2AX), a marker of DNA double stranded breaks, was measured by immunoblot. PD-L1$^{KO}$ RT4 and ID8agg cells exhibited markedly elevated $\gamma$H2AX following gemcitabine treatment versus respective control cells (FIG. 1B, FIG. 6B). Untreated PD-L1$^{KO}$ ID8agg cells displayed increased $\gamma$H2AX levels versus control cells (FIG. 6B). These results support the idea that tumor-intrinsic PD-L1 reduces DNA damage from basal replication stress or metabolism.

To determine if tumor-intrinsic PD-L1 promotes repair of damaged DNA following acute DNA damage, $\gamma$H2AX levels were measured in control and PD-L1$^{KO}$ cells following exposure to ionizing radiation, a potent and specific inducer of double stranded DNA breaks. PD-L1$^{KO}$ RT4 cells exhibited significantly delayed DNA repair kinetics while control cells fully resolved the DNA damage within 8 hours after irradiation (FIG. 1C). These results demonstrate tumor-intrinsic PD-L1 dependent control of the DDR and kinetics.

Gemcitabine-induced DNA damage strongly activates the apical kinases ATM and ATR (FIG. 1D). ATM subsequently activates Chk2 at Thr68 while ATR activates Chk1 at Ser345 in response to DNA damage including double strand breaks or stalled replication forks (O'Connor et al., 2015). Chk1 and Chk2 are relay kinases that initiate DNA repair pathways (O'Connor et al., 2015). We examined the ATM/Chk2 and ATR/Chk1 DDR signaling pathways post gem treatment. Deletion of PD-L1 in RT4 cells reduced Chk2, thus attenuating ATM/Chk2/p-Chk2 DDR signaling following gem treatment, with negligible effect on ATR/Chk1/p-Chk1 (FIG. 1D). Downstream DNA repair effector molecules (e.g., p-BRCA1$1524 and p-RPA32S4/S8) involved in reversing gemcitabine-induced damaged DNA failed to form significant nuclear foci in PD-L1$^{KO}$ compared to control cells (FIG. 7B). X-rays produced similar results in PD-L1KORT4 (FIG. 1E). In PD-L1$^{KO}$ ID8agg cells we observed robust Chk1 activation over control cells following gem treatment indicating tumor intrinsic PD-L1 suppresses activation of ATR/Chk1/p-Chk1 signaling and DNA damage from excess replication stress (FIG. 1F). Thus, tumor-intrinsic, cell type-dependent PD-L1 preferentially modulates aspects of DDR signaling with consequent impact on initiation of DNA repair.

PD-L1 maintains expression of DDR proteins by preventing degradation of the cognate mRNAs, particularly BRCA1 and NBS1 (MRN complex) (Gupta et al., 2016). Expression of essential DDR proteins including BRCA1, NBS1, ATM, ATR, Chk1, or RAD50 was measured at baseline and post gemcitabine induced DNA damage in PD-L1$^{KO}$ versus control cells. Chk2 was most significantly altered, but only after gemcitabine treatment and not at baseline in PD-L1$^{KO}$ cells (FIG. 1D). These data suggest tumor-specific PD-L1-driven DDR mechanisms.

Example 2

Tumor-Intrinsic PD-L1 Promotes Resistance to Chk1i or PARPi In Vitro and In Vivo After observing clear alterations in DDR signaling mediated by tumor-intrinsic PD-L1, whether PD-L1$^{KO}$ promoted synthetic lethality with selected DDRi agents was tested. Consistent with observed DDR alterations during gem induced replication stress (FIGS. 1A-D, FIGS. 7A-C, FIGS. 8A-B), we saw significant (over 15-fold) cytotoxicity in PD-L1$^{KO}$ versus control RT4 cells treated with the selective Chk1 inhibitor rabusertib in vitro (FIG. 2A). PD-L1$^{KO}$ cells were also more sensitive to the ATR inhibitor AZD6738 (FIG. 2B). Similar results were obtained for Chk1i or ATRi treated PD-L1$^{KO}$ versus control ID8agg cells (FIG. 2A-B). Minimal effects of the ATM inhibitor, AZD0156, or the PARP inhibitor olaparib. as monotherapy in PD-L1$^{KO}$RT4 or ID8agg cells (FIG. 2C-D) was observed, consistent with the observed DDR alterations (FIGS. 1A-D, FIG. 1F, FIGS. 6A-C, FIGS. 7A-B).

To test tumor-intrinsic PD-L1 effects on DDRi treatment in vivo, the highly tumorigenic MB49 murine bladder cancer and 4T1 murine breast cancer models were utilized. Like PD-L1-depleted RT4 and ID8agg, PD-L1$^{lo}$ 4T1 cells were significantly growth inhibited with Chk1i but not PARPi in vitro (FIG. 3A). PD-L1$^{KO}$ MB49 cells were more sensitive to PARPi but not Chk1i (FIG. 3A) in vitro, providing additional evidence that DDRi resistance mediated by tumor-intrinsic PD-L1 effects is cell type-dependent. To dissect tumor-intrinsic PD-L1 effects versus immune dependent effects of PD-L1, severely immunodeficient NSG mice were administered control or PD-L1$^{KO}$ cancer cells, and treatment outcomes were measured. Consistent with the in vitro findings, PD-L1$^{KO}$ but not control MB49 tumors were robustly growth inhibited and weighed less after PARPi treatment (FIG. 3C). Similarly, PD-L1$^{lo}$ but not control 4T1 tumors in NSG females were particularly sensitive to single agent Chk1i (FIG. 3D). Thus, tumor-intrinsic, immune-independent effects of PD-L1 include promoting resistance to Chk1i or PARPi in vivo, in distinct tumors, anatomic compartments, and genetic backgrounds. These results support the idea that, DDRi can be particularly useful in tumors with low PD-L1 expression or could be used at lower concentrations for similar efficacy with reduced adverse effects.

Example 3

Olaparib Efficacy in B16 Melanoma Depends on Tumor PD-L1 Expression and Adaptive Immunity Moderate differences were observed in olaparib cytotoxicity against PD-LIKO versus control B16 cells in vitro (FIG. 4A). Several prior studies demonstrated immune consequences of PARPi therapy in distinct tumor models in vivo (Pantelidou et al., 2019; Ding et al., 2018; Lee and Konstantinopoulos, 2019). Because tumor-intrinsic PD-L1 alters DDR signaling and olaparib activates anti-tumor immunity, we hypothesized that olaparib would synergize in vivo in immune competent mice (FIGS. 6A-E). In contrast to in vitro data, olaparib was significantly more effective in controlling PD-L1$^{KO}$ versus control B16 growth in vivo in wild type mice (FIGS. 4B-C). Strikingly, olaparib was ineffective in limiting PD-L1$^{KO}$ B16 tumors in RAG2$^{KO}$ mice lacking adaptive immunity (FIG. 4D). Together, these results are consistent with the concept that tumor PD-L1 inhibits PARPi efficacy and that the effect is immune dependent. These data further establish cell type specific PD-L1 signaling effects requiring additional investigation.

As shown in the above Examples, tumor-intrinsic PD-L1 signals mediated chemoresistance in distinct mouse and human tumor lines, prevented DNA damage accumulation following gemcitabine exposure, and facilitated DNA repair following ionizing irradiation. Tumor-intrinsic PD-L1 promoted Chk2 expression in human RT4 bladder cancer cells or suppressed ATR/Chk1/p-Chk1 signaling in ID8agg mouse ovarian cancer cells after gemcitabine-induced replication stress, indicating cell type-dependent tumor-intrinsic PD-L1 control of the DDR. The inventors postulated that loss of tumor-intrinsic PD-L1 signals would create treatment-exploitable DDR defects. Using distinct DDRi agents, robust in vitro sensitivity to Chk1 inhibition and more moderately ATR inhibition, in PD-L1$^{KO}$ RT4 and ID8agg tumor cells, was observed. PD-L1 also promoted resistance to DDRi agents in vivo. Deletion of PD-L1 in MB49 bladder tumors and 4T1 breast cancers resulted in significant sensitivity to PARPi and Chk1i agents, respectively, in vivo. These results support targeting tumor-intrinsic PD-L1 to sensitize immunotherapy resistant tumors to DDRi agents. In some aspects, tumor PD-L1 may be used as a biomarker for response to DDRi agents alone or combined with chemotherapy or immunotherapy.

Tumor-intrinsic PD-L1 exerts diverse effects on pivotal cellular survival, metabolic, and signaling pathways including promoting mTOR, tumor initiating (stem) cells, Ras/Mek/Erk, PI3K/AKT, JAK/STAT signaling, and inhibiting autophagy and mRNA degradation (Clark et al., 2016; Gupta et al., 2016; Tu et al., 2019; Escors et al., 2018; Feng et al., 2019; Dong et al., 2002; Qiu et al., 2018; Chang et al., 2015). Tumor-intrinsic PD-L1 effects on DDR could be dependent or independent of these known mechanisms. Doxorubicin treatment of breast cancer cells induced PD-L1 nuclear translocation suggesting PD-L1 direct involvement in nuclear DNA repair mechanisms (Ghebeh et al., 2010).

PD-L1 depletion resulted in robust growth inhibition in B16 tumors in wild-type mice following treatment with the PARPi, olaparib. Growth inhibition depended on adaptive immunity suggesting the immunomodulatory potential of PARPi is altered by tumor PD-L1. PD-L1-depleted B16 tumors failed to respond to anti-PD-L1 (Cottrell et al., 2018). PARPi and the other DDRi agents studied can be combine with immune checkpoint blockade to treat patients with PD-L1 low/null tumors. PARPi has been previously shown to enhance CD8+ T cell killing through cGAS/STING activation and improves anti-PD-L1 therapy in BRCA1 proficient or deficient tumors (Pantelidou et al., 2019; Ding et al., 2018; Lee and Konstantinopoulos, 2019; Sen et al., 2019). Without wishing to be bound by any theory, it is unclear to what extent tumor-intrinsic PD-L1 might alters innate immune signaling or the tumor microenvironment in tumors after DDRi treatment. Without wishing to be bound by any theory, it is also unknown whether PARPi increases tumor mutational burden and if such effects can be potentiated by blocking tumor-intrinsic PD-L1 signals.

The data in the above examples shows that tumor-intrinsic PD-L1 alters various aspects of DDR signaling that can be used for synthetic lethality with Chk1i or PARPi (e.g., olaparib) in distinct immunotherapy resistant tumors in vitro and in vivo. For example, the DDRi could be administered alone to patients with tumors that express little or no PD-L1, and the DDRi can optionally be combined with an additional immunotherapy or chemotherapy.

Tumor cells were depleted of PD-L1 by shRNA or PD-L1 was deleted by CRISPR/Cas9 (FIG. 5A-H).

Example 4

Materials and Methods

The materials and methods used in Examples 1-3 are provided below.

Cell Lines and Constructs

Murine melanoma B16-F10 (hereafter "B16") and murine ovarian cancer ID8agg cells were previously described (Fujita et al., 2015). Murine 4T1 breast cancer cells were purchased from the America Type Culture Collection. These were cultured in RPMI-1640 (Corning) containing 5% fetal bovine serum, 1% penicillin/streptomycin, 1% L-glutamate, and 1% HEPES. Human RT4 and murine MB49 bladder cancer cell lines were gifts from R. S. Svatek (UTHSA) and were cultured in McCoy's 5A or DMEM modified medium (GIBCO), respectively, plus 1% penicillin/streptomycin. All lines were tested periodically and confirmed *Mycoplasma* free by Mycoalert PLUS (Lonza Bioscience).

PD-L1 knockout (PD-L1$^{KO}$) cell lines were generated using commercially available CRISRP/cas9 plasmids. sgRNA sequences used to generate PD-L1$^{KO}$ murine cells include CTCCAAAGGACTTGTACG (SEQ ID NO: 13), GCAAGTGATTCAGTTTG (SEQ ID NO: 14) and TGCTGCATAATCAGCTA (SEQ ID NO: 15). PD-L1$^{KO}$ RT4 cells were generated using human PD-L1 targeting sgRNA sequences TCCCAAGGACCTATATG (SEQ ID NO: 16), ATAGTAGCTACAGACAG (SEQ ID NO: 17) and CGCTGCATGATCAGCTA (SEQ ID NO: 18). Clones were validated using flow cytometry, sequencing and immunoblots (FIGS. 6A-D). PD-L1 knockdown (PD-L1$^{lo}$) in 4T1 cells was by lentiviral vector transduction with PD-L1 shRNA (Sigma) or a scrambled shRNA control as we described (Clark et al., 2016).

Chemicals and X-Rays

Gemcitabine was a gift from Dr. Robert Svatek, University of Texas Health San Antonio. LY2602618 (Chk1i), olaparib (PARPi), AZD0156 (ATMi), and AZD6738 (ATRi) were purchased from Selleckchem. AZDO156 was diluted in 100% ethanol for in vitro treatments. All other DDR inhibitors were diluted in DMSO for in vitro studies. Irradiation was with CellRad hardware (Precision).

Immunoblots

Immunoblotting was performed as described (Clark et al., 2016; Gupta et al., 2016). Protein was measured by BCA (ThermoFisher). Cell Signaling antibodies were phospho-histone H2A.X (#9718), phospho-Chk1$^{Ser345}$ (#2348), phosph-Chk2$^{Thr68}$ (#2197), phospho-ATM$^{Ser1981}$ (#5883), phospho-ATR$^{Ser428}$ (#2853), total-Chk1 (#2360), total-chk2 (#2662), total-ATM (#2873), total-ATR (#13934), total-NBS1 (#14956), total-Rad50 (#3427), RAD51, vinculin (#13901), beta-actin (#12620), human-PD-L1 (#13684), mouse-PD-L1. Abcam antibodies were (ab3801) and (ab80276) and total-BRCA1 was R&D MAB22101. All were used as per manufacturer's recommendation.

Mice

Wild type C57BL/6J (BL6), RAG2$^{KO}$ (BL6), and NOD.Cg-Prkdc$^{scid}$Il2rg$^{tm1wjl}$/Szj (Non-obese diabetic/severe combined immunodeficiency, NSG) mice were either bred in our in-house facility or purchased from Jackson Labs and maintained under pathogen free conditions. All animal studies were approved by the UT Health San Antonio IACUC.

In Vivo Tumor Challenges and Treatments

NSG mice were challenged with MB49 (0.3×10$^6$ cells) subcutaneously on opposite flanks. Olaparib (daily 25 mg/kg, 4% DMSO) was injected intraperitoneally on days 3-11. 4T1 (0.5×10$^6$ cells) were injected into mammary fat pads of NSG mice with Matrigel (1:1, Corning). Rabusertib (LY2602618, 4% DMSO) was administered intraperitoneally on day 3 (10 mg/kg) and days 10 and 17 (1 mg/kg).

B16 cells were injected subcutaneously on opposite flanks into BL6 (0.5×10$^6$ cells) or RAG2$^{KO}$ mice (0.4×10$^6$). Olaparib was administered daily intraperitoneally (50 mg/kg, 4% DMSO) on days 3-13. Tumors were measured with Vernier calipers and volume calculated as (length×width$^2$)/2. Mice were sacrificed when tumors reached ~1500 mm$^3$ or if distressed.

In Vitro Proliferation and Viability

Cells (1×10$^3$) were plated in 96 well plastic culture plates in respective medium and treated for 5 days with DDRi or 3 days with gemcitabine at indicated concentrations. Drug concentrations were carefully optimized in preliminary work not shown. Cell viability was by MTT (3-(4,5-dimethylthiazol-2-yl)-2,5-diphenyl tetrazolium bromide) at 5 mg/ml. Absorbance was measured at 540 nm. Results are presented as a mean+/−SEM of ≥6 replicates. Total cells and viability were confirmed using a Vi-Cell-XR (Beckman Coulter).

Microscopy

Cells were seeded into 8 well IBIDI silicone-chambered slides and treated as indicated. Cells were fixed with 100% methanol (5 mins) followed by 1×PBS wash. Staining was performed using MAXpack Immunostaining Media Kit (Active Motif). Cells were incubated with MAXblock Blocking Medium for 1 hr at room temperature, followed by incubation with primary antibodies diluted in MAXbind Staining Medium at 4° C. overnight. Primary antibodies were p-BRCA1$^{Ser1524}$ (1:200, Cell Signaling, #9009), p-RPA32-S4/8 (1:200, Cell Signaling, #ab87277), RAD51 (1:200, Abcam, ab3801), PD-L1 (1:1000, Cell Signaling, #29122). Cells were then washed with MAXwash and incubated with secondary antibodies (1:400 conjugated to Alexa Fluor 488 or Alexa Fluor 647-. After washing 3×10 min with MAXwash, DAPI stain (0.02 g/ml, Sigma, D9542) was applied for 10 min at ambient temperature, followed by MAXwash. Slides were mounted with ProLong Diamond (ThermoFisher Scientific) and Slip-Rite cover glass (ThermoFisher Scientific). Fluorescence was detected using a TE 2000U microscope (Nikon) and overlaid using ImageJ.

Statistics

Statistical analyses were performed using Prism software (GraphPad). Most data are represented as mean+/−SEM. In vivo tumor growth was analyzed by 2-way ANOVA plus Bonferroni post-tests. All other single measurement assays were assessed with unpaired student's t test. P values <0.05 were considered significant.

Example 5

Tumour Cytoplasmic PD-L1 Promotes Treatment Resistance and Predicts Immunotherapy Outcomes in Human Patients Tumour PD-L1 Regulates Lamtors to Activate mTORC1

Figure 8C:
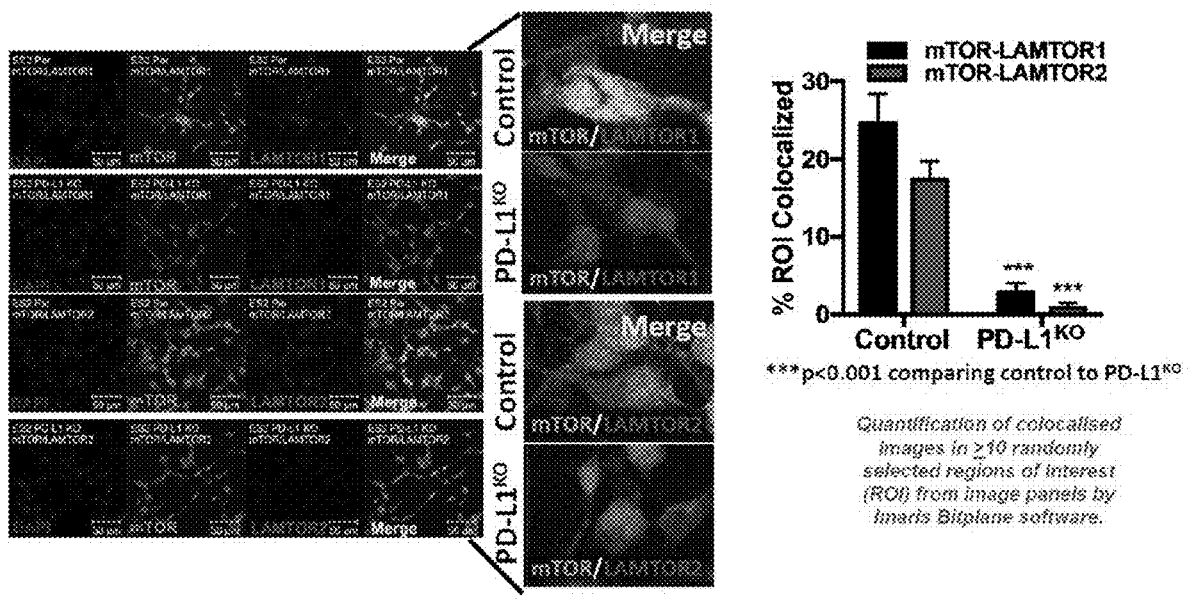
Figure 8D:
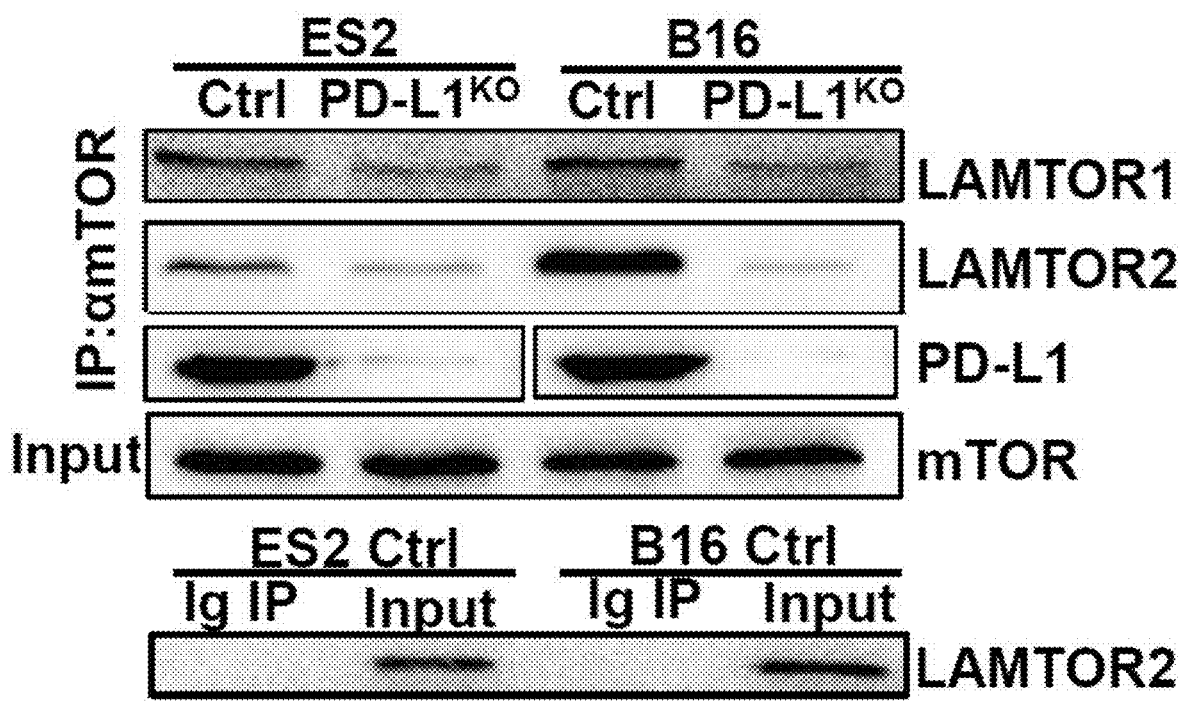
Figure 8E:
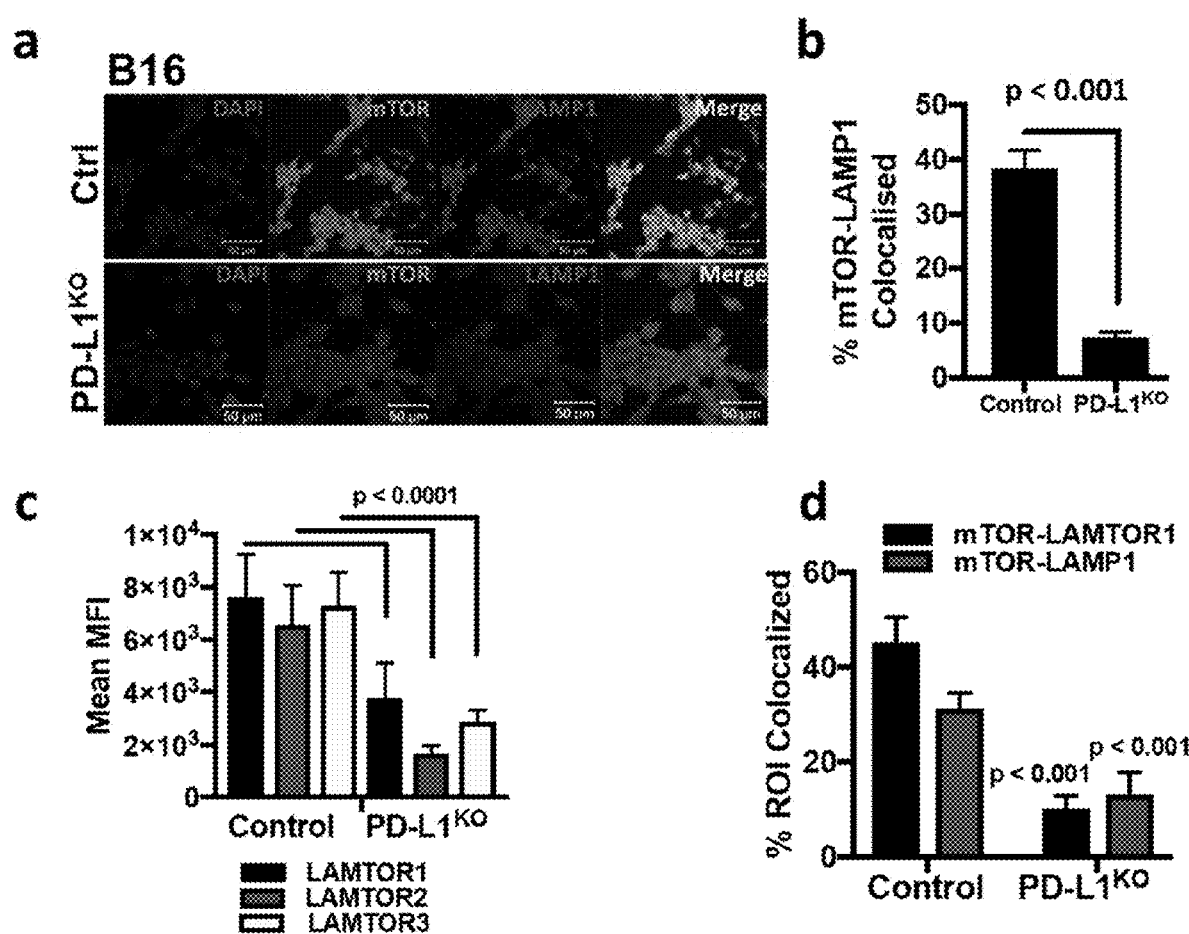
Figure 9:
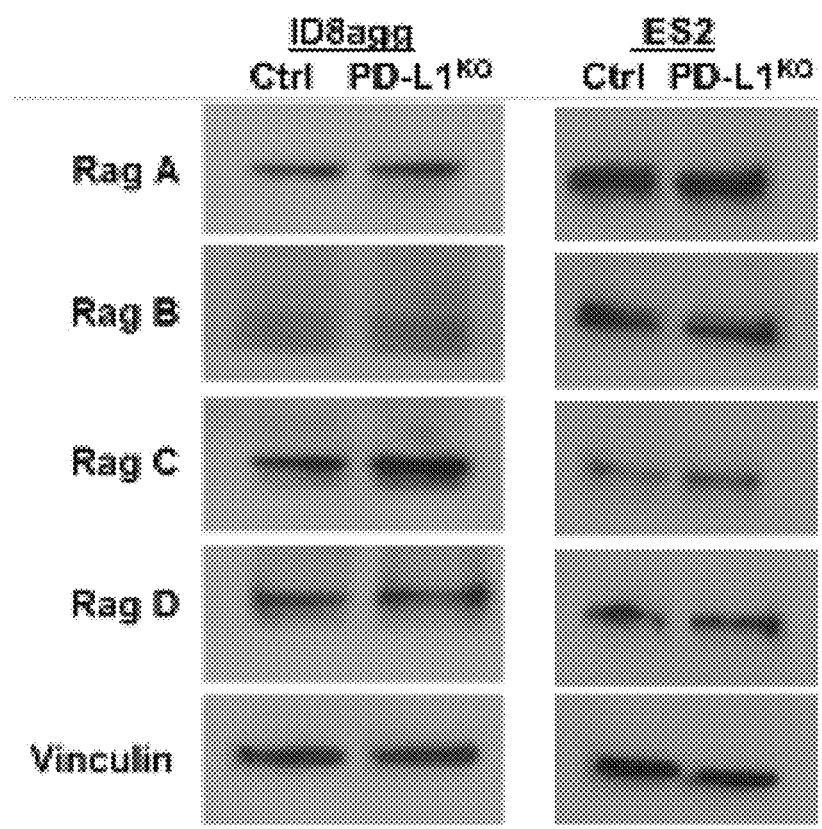
FIG. 9: PD-L1 depletion does not reduce RAG ATPases. 4 Rag GTPases (A-D) are also involved in mTORC1 activation by Ragulator.

Tumour-intrinsic PD-L1 signals can promote tumour pathogenesis through non-canonical mechanisms and activate tumour mTORC1 signals, but links between mTORC1 activation and specific pathogenesis programs and related mechanisms remain unknown. Cell-intrinsic PD-L1 in ID8agg mouse ovarian cancer cells and ES2 human ovarian cancer cells did not alter significantly Raptor, a foundational mTORC1 protein, or Rheb, (FIG. 8A), the ultimate mediator of mTORC1 activation (Sancak et al., 2010). mTORC1 activation can be promoted by its lysosomal association LAMP1, LAMP2) through Ragulator, a complex of 5 Lamtor proteins (Lamtor1-5) (Sancak et al., 2010). Confocal imaging of ES2 cells showed PD-L1$^{KO}$ significantly reduced mTORC1 lysosomal association (FIG. 8B) required for mTORC1 activation through Ragulator and reduced Lamtor1-3 content (FIG. 8C), confirmed by Lamtor immunoblots (FIG. 8D). Lamtors and mTORC1 association with Ragulator and lysosomes were similarly controlled by PD-L1 in B16 cells (FIG. 8E), whereas the four Rag GTPases that cooperate with Ragulator for mTORC1 activation (Sancak et al., 2010) were minimally affected in PD-L1$^{KO}$ B16 and ES2 cells (FIG. 9). Anti-mTOR immunoprecipitated Lamtors in control ES2 cells as expected (showing Ragulator association with mTORC1) but immunoprecipitated Lamtors significantly less efficiently in PD-L1$^{KO}$ cells (FIG. 8D). Confocal imaging with Imaris analyses showed reduced mTOR association with Lamtor1-2 in PD-L1$^{KO}$ versus control ES2 cells (FIG. 8C) defining deficient mTORC1 association with Ragulator upon PD-L1 depletion. Depletion of Lamtor1 alone reduces other Lamtors and is sufficient to compromise Ragulator function; increasing Lamtor1 expression in Lamtor-depleted cells increases content of other Lamtors (Filipek et al., 2017). We forced Lamtor1 expression in PD-L1$^{KO}$ cells with a constitutive expression vector, which restored expression of Lamtor2 and Lamtor3 as reported for benign cells (Tu et al., 2019). Similarly, Lamtor1 depletion (using shRNA) in PD-L1 replete control cells reduced other Lamtors as reported in benign cells (Filipek et al., 2017), and mTORC1 signals and associations between Ragulator and mTORC1, and mTORC1 and lysosomes (FIG. 8F). Therefore, tumour PD-L1 promotes Lamtor expression to enhance mTORC1 association with Ragulator, and Ragulator capacity to associate mTORC1 with lysosomes for mTORC1 activation.

Cytoplasmic PD-L1 activates mTORC1 independent of its cytoplasmic tailCytophasmic PD-L1 was measured in tumor biopsies, as follows. Tumor biopsies from 3 responder (R) and 3 non-responder (NR) ovarian cancer patients in a trial of pembrolizumab plus cyclophosphamide plus bevacizumab were studied. Responders were defined as surviving >24 months after treatment initiation before disease progression. Non-responders were defined as surviving <4 months after treatment initiation before disease progression. Tumor biopsies were formalin-fixed, paraffin-embedded tumors, cut into 5 micron slices and stained with specific antibodies coupled to barcoded UV-photocleavable oligonucleotides from NanoString. Percent surface and cytoplasmic PD-L1 was determined by assessing oligonucleotide location using FIJI software at 0.325 µm/pixel resolution to map x-y coordinates through the focal plane. Total tumor PD-L1 was determined by Nanostring GeoMx™ Spatial Imaging Platform using mapped to x-y coordinates and signal from barcoded oligonucleotides to obtain surface and cytoplasmic data. The mean of 3 regions of interest/patient was assessed by 2-way ANOVA with Tukey's multiple comparisons test.

Figure 10:
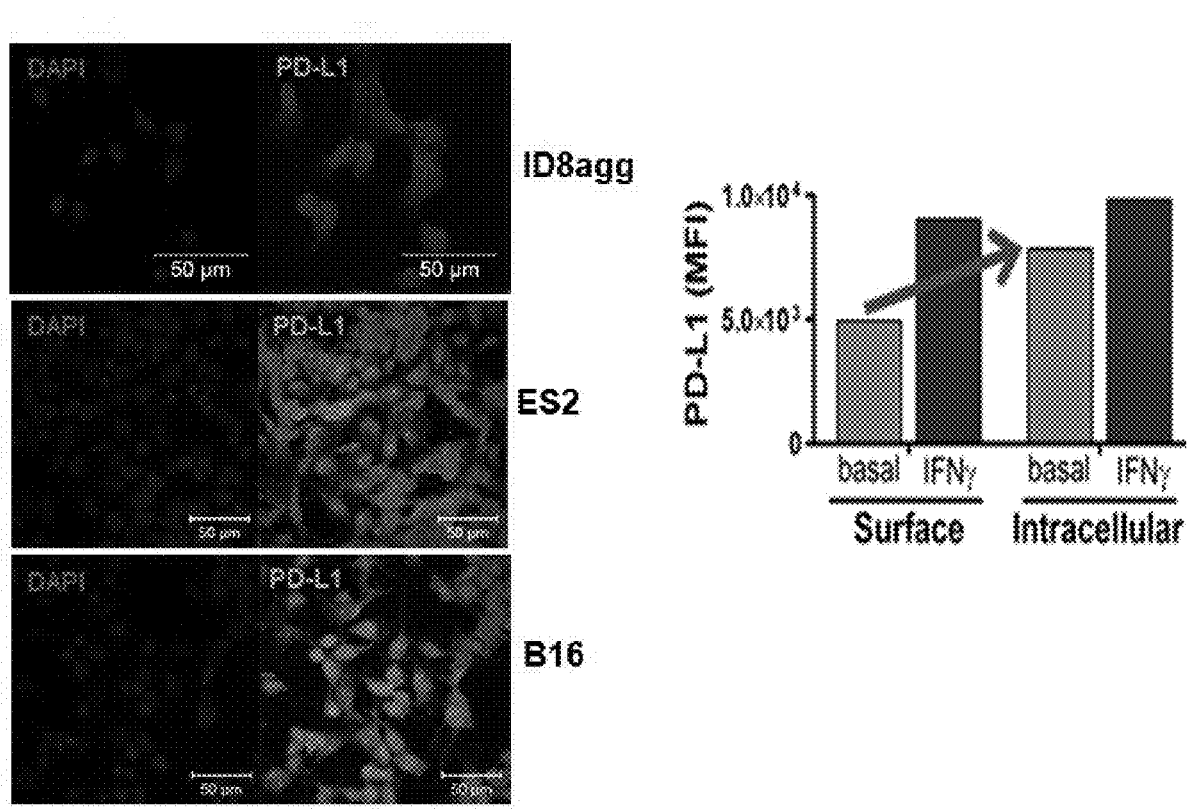
FIG. 10: Substantial intracellular PD-L1 is detected in long-term and primary cancer cells in mice and humans. On the left are confocal images of intracellular PD-L1 in human ES2 ovarian cancer cells and B16 mouse melanoma cells. On the right is a flow cytometry analysis of non-permeabilized versus permeabilized ovarian cancer cells taken directly from a human patient. The red arrow shows the increased PD-L1 signal on permeabilization indicative of the intracellular PD-L1 content. See also confocal imaging and summary human melanoma and ovarian cancer TMA or human clinical trial data representing cells taken directly from humans in FIG. 10, FIG. 15, FIG. 18A, FIGS. 19B,C.
Figure 11A:
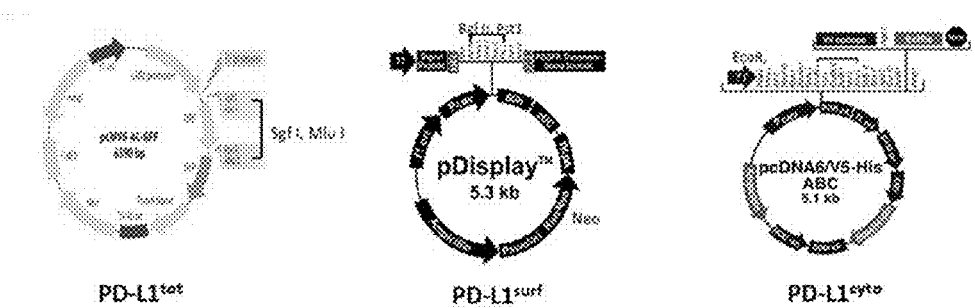
FIGS. 11A-F: Intracellular PD-L1, not surface PD-L1 mediates mTORC1 lysosomal docking and activation.
Figure 11B:
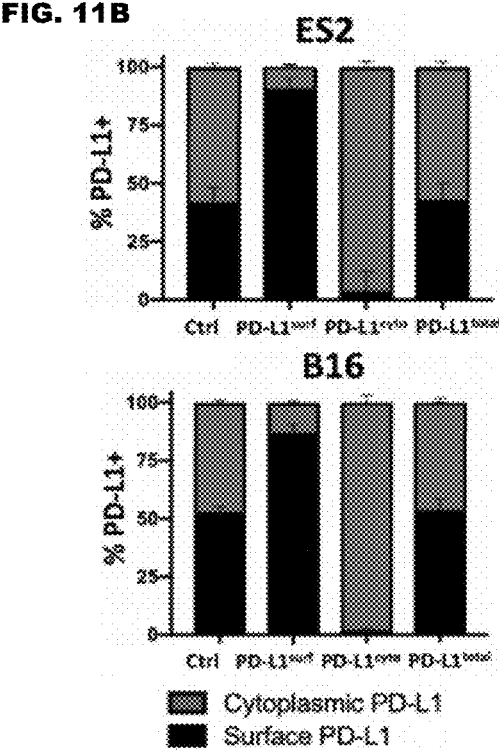
Figure 11C:
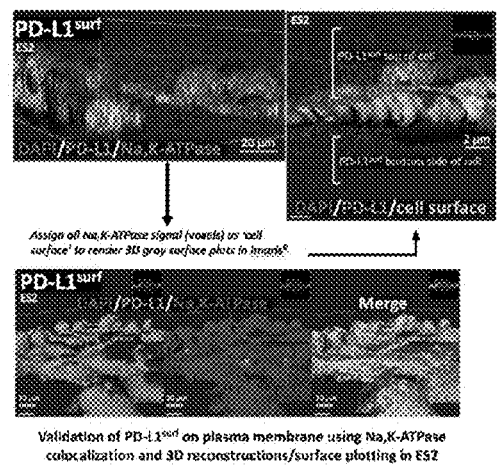
Figure 11D:
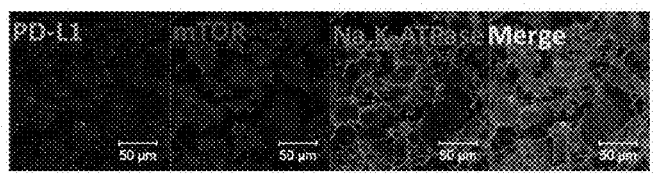
Figure 11E:
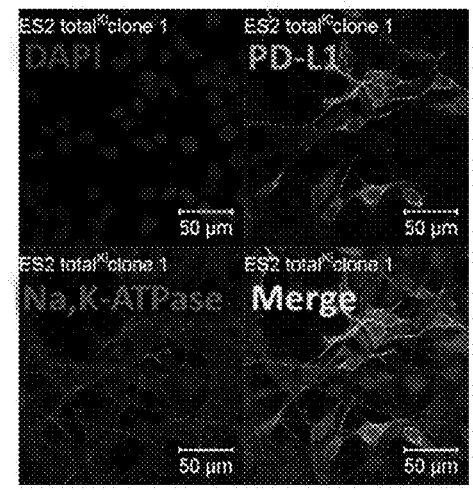
Figure 11F:
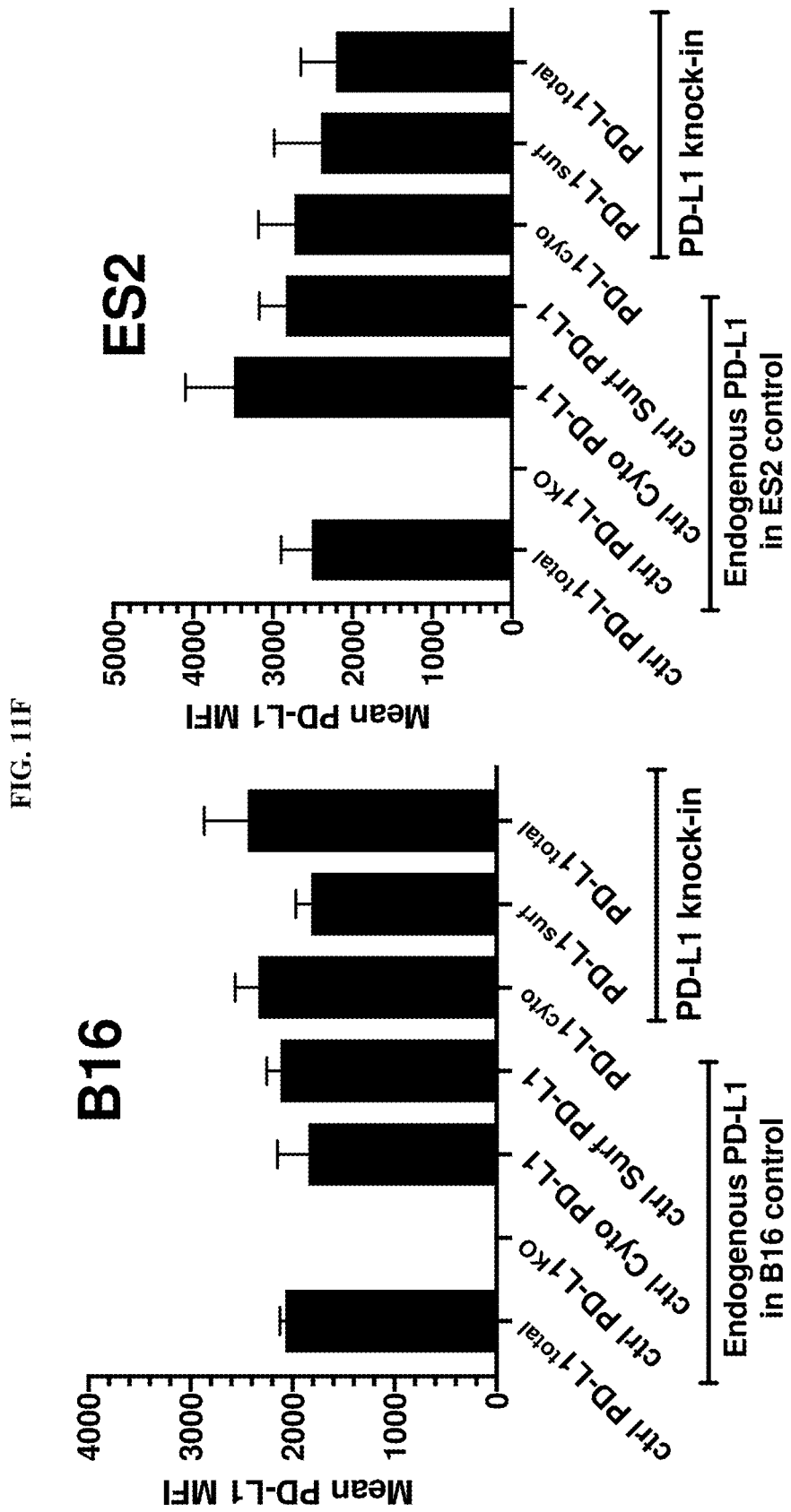

Substantial intracellular PD-L1 was detected in B16, ID8agg, ES2 and primary human ovarian cancer cells by flow cytometry and confocal microscopy (FIG. 10; ref. Gupta et al., 2016). To assess subcellular PD-L1 effects, the inventors expressed subcellular-specific PD-L1 with CRISPR-resistant PD-L1 cDNA in a vector expressing PD-L1 fused to platelet-derived growth factor receptor transmembrane domain, anchoring it to extracellular membrane (PD-L1$^{surf}$), and another vector expressing PD-L1 fused to myristic acid to maintain PD-L1 in cytoplasm (PD-L1$^{cyto}$), and a total re-expression control (PD-L1$^{total}$) (FIG. 11A), and re-expressed each in PD-L1$^{KO}$ cells. Digital confocal imaging and immunoblots confirmed specific PD-L1 expression matching control cell expression in respective subcellular locations in B16 and ES2 cells (FIG. 11B). Additional imaging confirmed that PD-L1$^{surf}$ was only on the cell surface, PD-L1$^{cyto}$ was essentially only in cytoplasm and PD-L1$^{total}$ control re-expressed PD-L1 in both compartments (FIGS. 11C-E) and expression levels in each compartment mirrored the expression in parental cells in B16 and ES2 cells (FIG. 11F).

Cytoplasmic PD-L1 generated many signaling and cell effects distinct from surface PD-L1 seen by RNA-seq (FIG. 12A) and functional differences by atomic force microscopy (FIG. 12B). Most notably, cytoplasmic but not surface PD-L1 restored Lamtor expression, mTORC1 association with Ragulator and Ragulator association with lysosomes and mTORC1 signals in ES2 and B16 cells (FIGS. 12C,D). To test effects of cytoplasmic versus surface PD-L1 on mTORC1 signals, we showed that cytoplasmic PD-L1 restores mTORC1 signals in ES2 cells whereas surface PD-L1 did not (FIG. 12E).

Figure 13A:
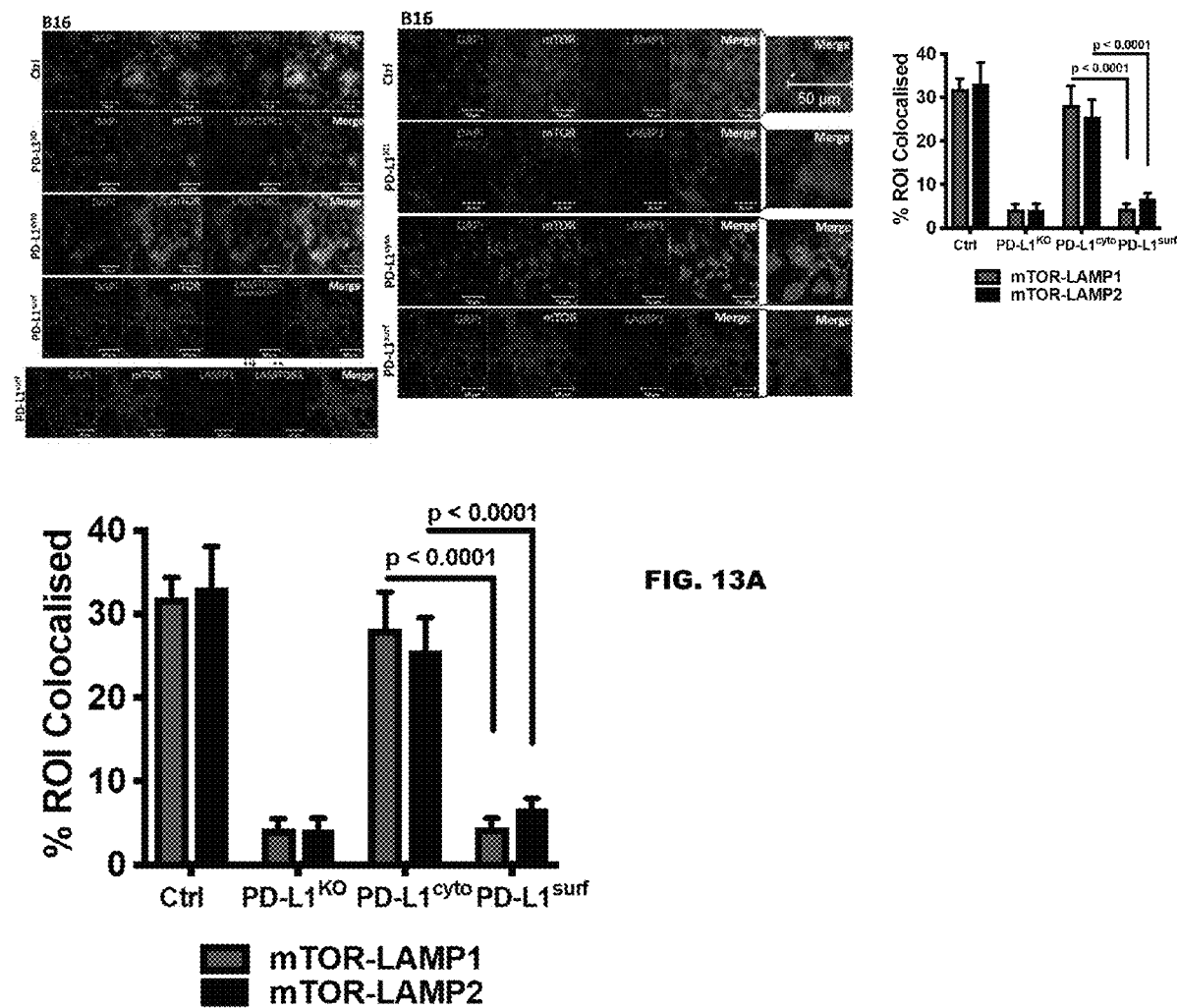
FIG. 13A-B: PD-L1$^{cyto}$ but not PD-L1$^{surf}$ restores Lamtor expression, Ragulator/mTORC1 and mTORC1/lysosomal associations and mTORC1 signals.
Figure 13B:
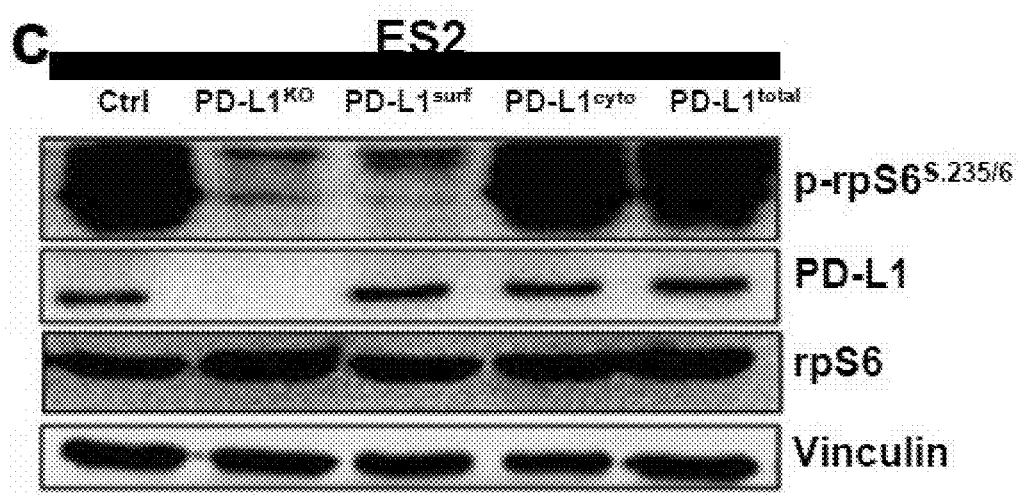

To determine if cytoplasmic PD-L1 signaled through its known cytoplasmic tail signals identified in mouse cells (Gato-Canas et al., 2017) for these outcomes, we considered naturally-occurring human PD-L1 isoform 2 that lacks N-terminal amino acids 19-132 but retains the cytoplasmic tail and is essentially only expressed in cytoplasm (He et al., 2005). We expressed PD-L1 isoform 2 only in cytoplasm of PD-L1$^{KO}$ ES2 cells using the surface expression vector described above (PD-L1$^{cyto-iso2}$ ES2) plus a tet-inducible promoter to titrate expression. PD-L1$^{cyto-iso2}$ did not increase Lamtor expression or co-localise with mTOR or lysosomes, or restore mTORC1 association lysosomes or mTORC1 signals in ES2 cells contrasting with PD-L1$^{cyto}$ ES2 cells expressing full length PD-L1 even when PD-L1 isoform 2 was over-expressed 50-fold above its basal level (FIGS. 13A,B). Therefore, cytoplasmic, but not surface PD-L1 mediates Lamtor expression for mTORC1 activation and these cytoplasmic effects differ from described PD-L1 cytoplasmic tail signals.

Lamtor Content Predicts Survival in Ovarian Cancer and Melanoma

Figure 14A:
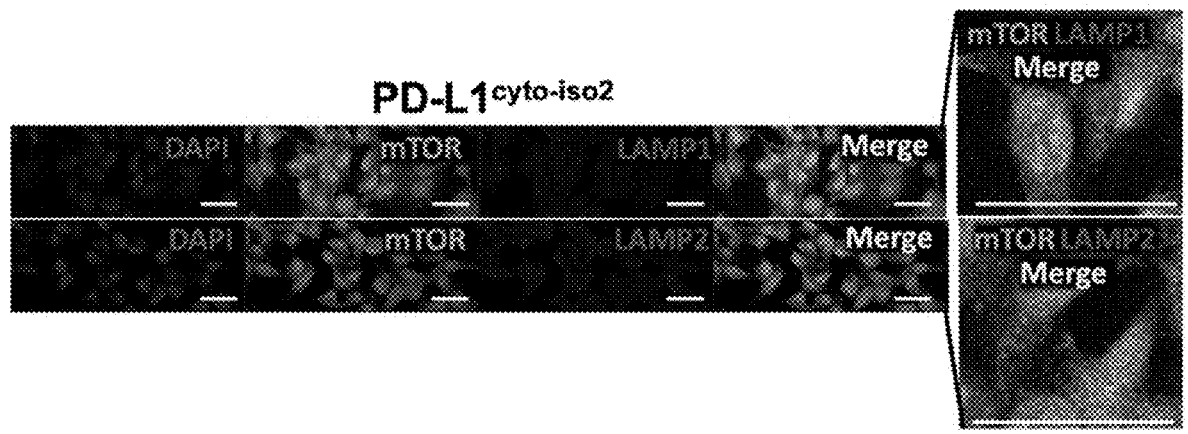
FIG. 14A-B: PD-L1 isoform 2 does not rescue Lamtor content, mTORC1/lysosome or mTORC1/Ragulator associations in ES2 cells.
Figure 14B:
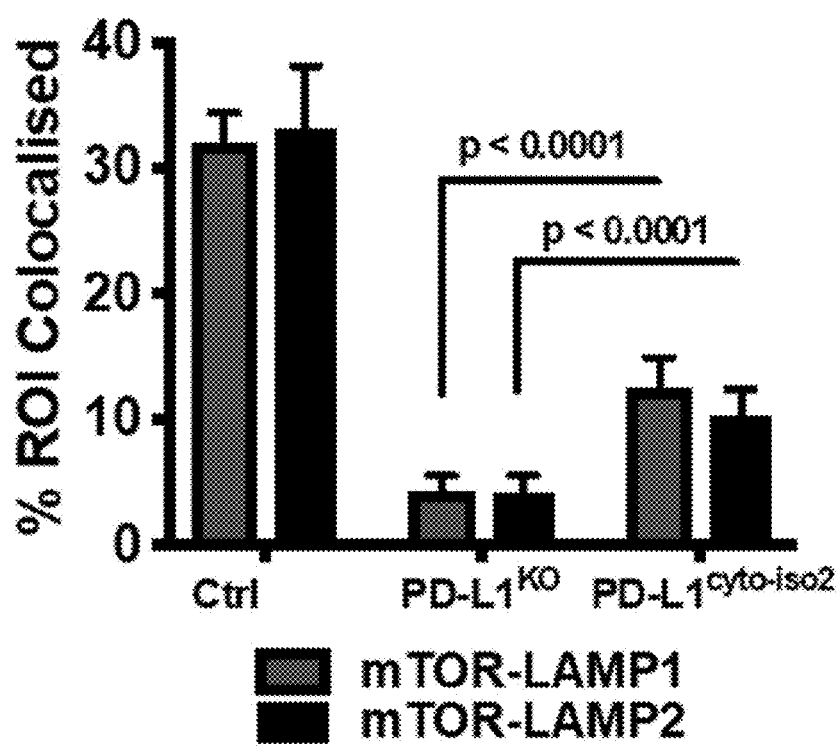

The Cancer Genome Atlas data was mined and an inverse overall survival in PD-L1-expressing melanomas and ovarian cancers versus Lamtor1 or Lamtor2 (FIGS. 14A,B) was observed. Because this data is from messenger RNA that potentially unreliably reflects PD-L1 protein (Burr et al., 2017), the inventors used both ovarian and melanoma tissue microarrays to confirm that tumour PD-L1 protein reliably predicted tumour Lamtor1 protein, and that specifically cytoplasmic PD-L1 reliably positively predicted tumor LAMTOR content (FIGS. 14C,D). Further, because these data are from human patients and not from human tumor cell lines, these tissue microarray data prove that the connection between cytoplasmic tumor PD-L1 and tumor LAMTOR content is valid. The TCGA survival data support the concept that tumor LAMTOR content has prognostic significance in human ovarian cancer and melanoma. In some embodiments, tumor PD-L1 can be used to predict tumor LAMTOR content or survival in other cancers including, but not limited to breast cancer and bladder cancer.

In some embodiments, LAMTOR downstream signals such as mTORC1 activation could predict survival alone or in combination with tumor PD-L1 or LAMTOR expression.

Naturally Occurring Tumours can Predominantly Express Surface or Cytoplasmic PD-L1

Figure 15:
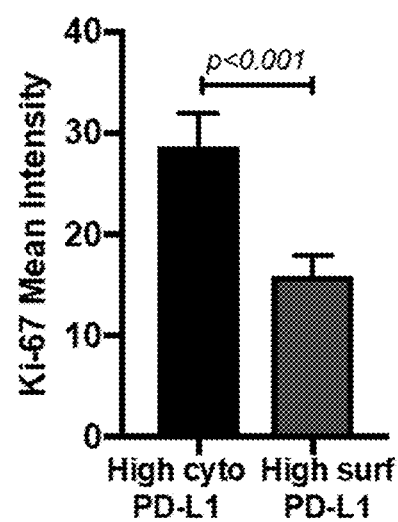
FIG. 15: Lamtor2 in tumor predicts survival in ovarian cancer. LAMTOR2 expression in melanoma predicts overall survival. MDACC melanoma TMA. 99 untreated stage III patients. Cytoplasmic PD-L1 predicts Ki67 proliferation marker in melanoma tumors.

Among 99 microarray melanomas, confocal imaging and Imaris software identified 21 expressing largely cytoplasmic PD-L1, 19 largely surface, and 59 with mixed PD-L1 demonstrating naturally-occurring, disparate subcellular PD-L1 expression, and this in ovarian cancers (FIG. 15). Cytoplasmic, but not total or surface PD-L1 significantly correlated with tumour Lamtor1 and Lamtor2 in melanomas and ovarian cancers (FIG. 14C,D) and correlated with the Ki67 proliferation marker (FIG. 14E). Thus, naturally-occurring tumours express cytoplasmic PD-L1 that predicts virulence.

Figure 16A:
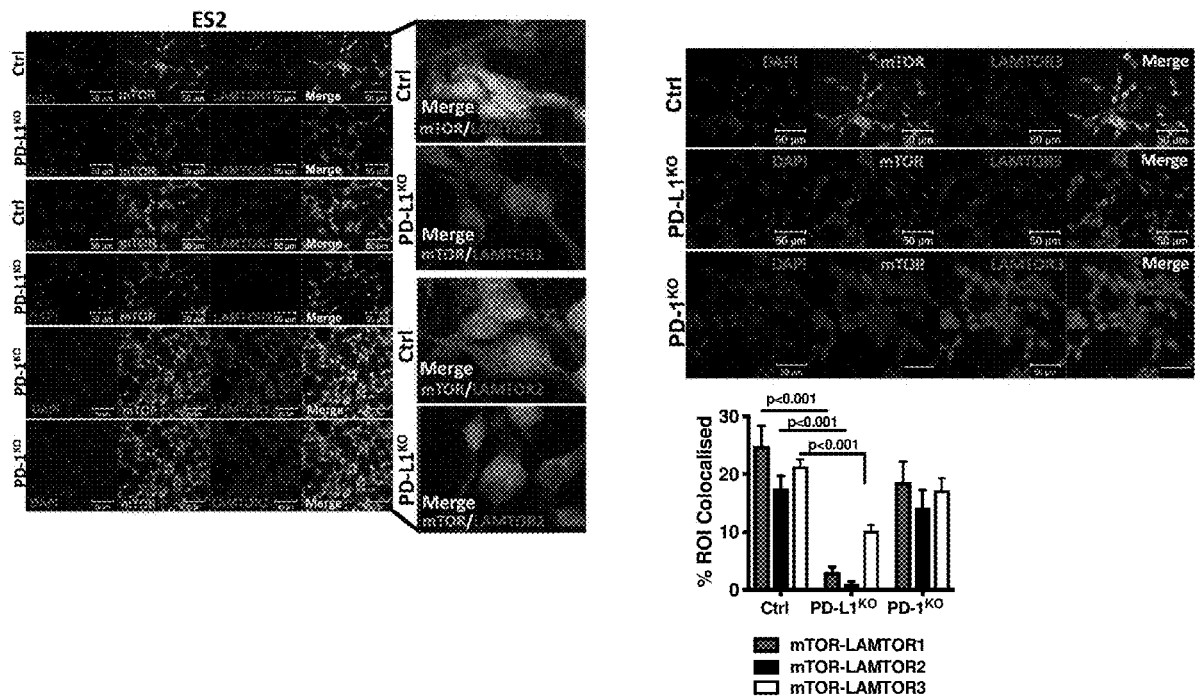
FIGS. 16A-C: Tumor PD-1 does not predict Lamtor content, mTORC1/Ragulator association, mTORC1/lysosome association or mTORC1 signals in ES2 ovarian cancer cells.
Figure 16B:
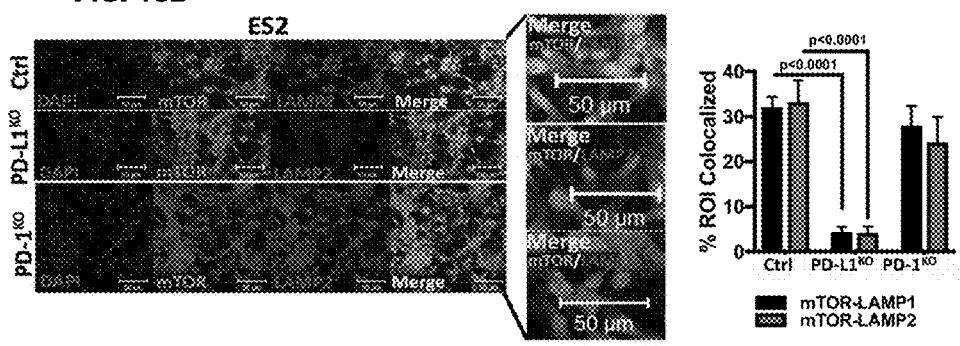
Figure 16C:
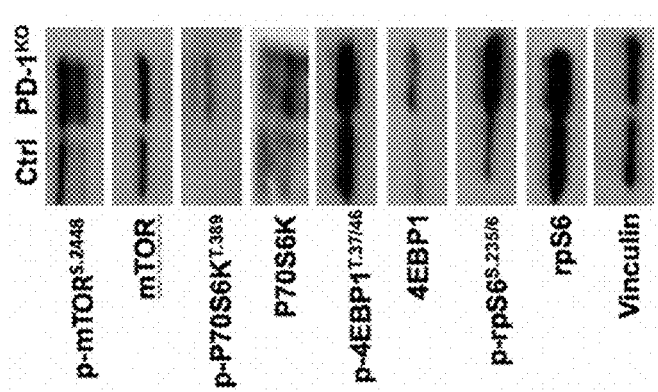

PD-1 is a natural binding partner for PD-L1. To assess effects of tumor PD-1, we used CRISPR/Cas9 to KO PD-1 from human ES2 ovarian cancer cells and mouse B16 melanoma cells. As shown in FIG. 15, PD-1$^{KO}$ ES2 cells maintained LAMTOR content, mTORC1/Ragulator association, mTORC1/lysosome associations, and mTORC1 signals, all similar to parental control ES2 cells whereas PD-1$^{KO}$ B16 cells were deficient in LAMTOR content, mTORC1 activation, mTORC1/Ragulator associations and mTORC1/lysosome associations and resembled PD-L1$^{KO}$ cells (FIG. 16).

Significant melanoma cytoplasmic PD-1 was also detected (FIG. 16C) that predicted mTORC1 lysosomal association. Thus, in some embodiments, tumor PD-1 or cytoplasmic PD-1 or the ratio of surface to cytoplasmic PD-1 can be used to assess treatment responsiveness or prognosis.

Ovarian Cancer Cytoplasmic PD-L1 Expression Predicts αPD-1 Response

Figure 17B:
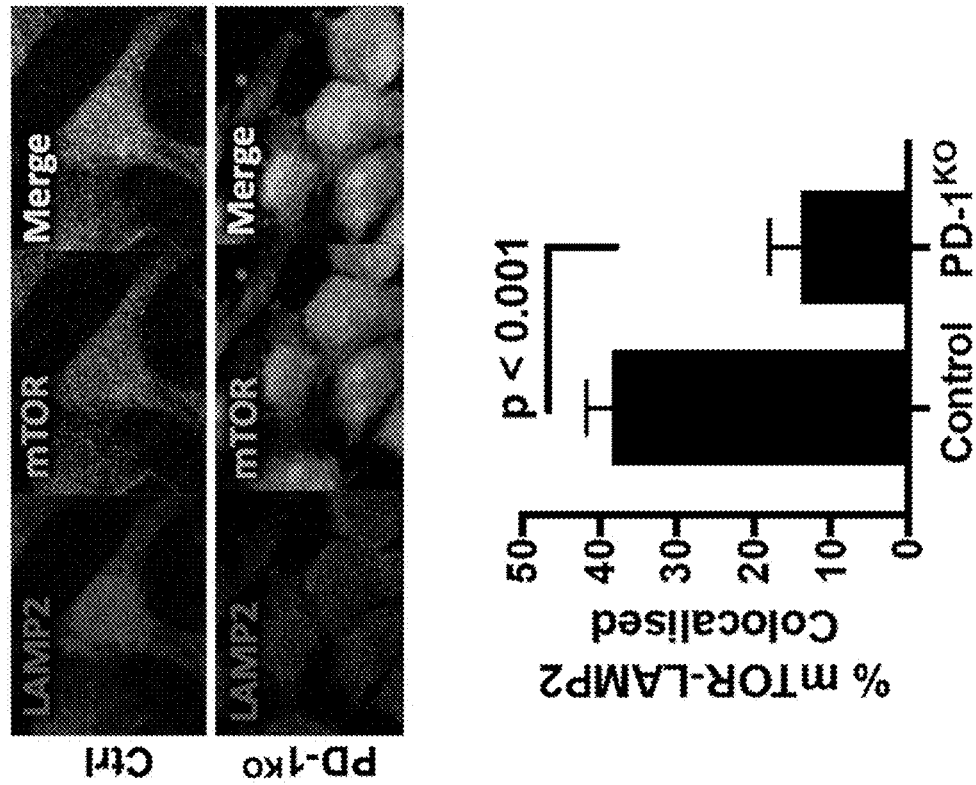
FIGS. 17A-B: Tumor PD-1 does not predict Lamtor content, mTORC1/Ragulator association, mTORC1/lysosome association or mTORC1 signals in B16 melanoma cells.
Figure 17A:
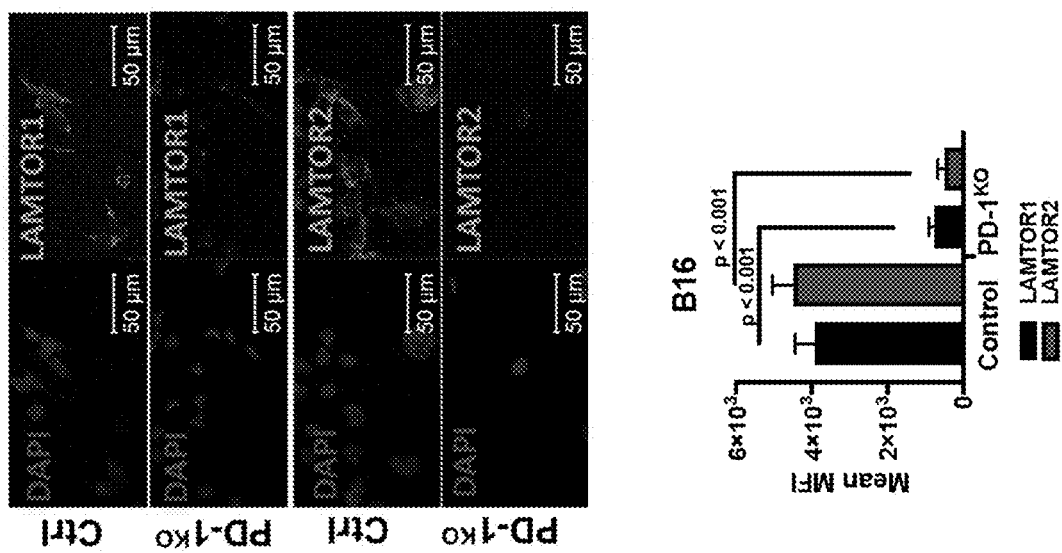
Figure 18A:
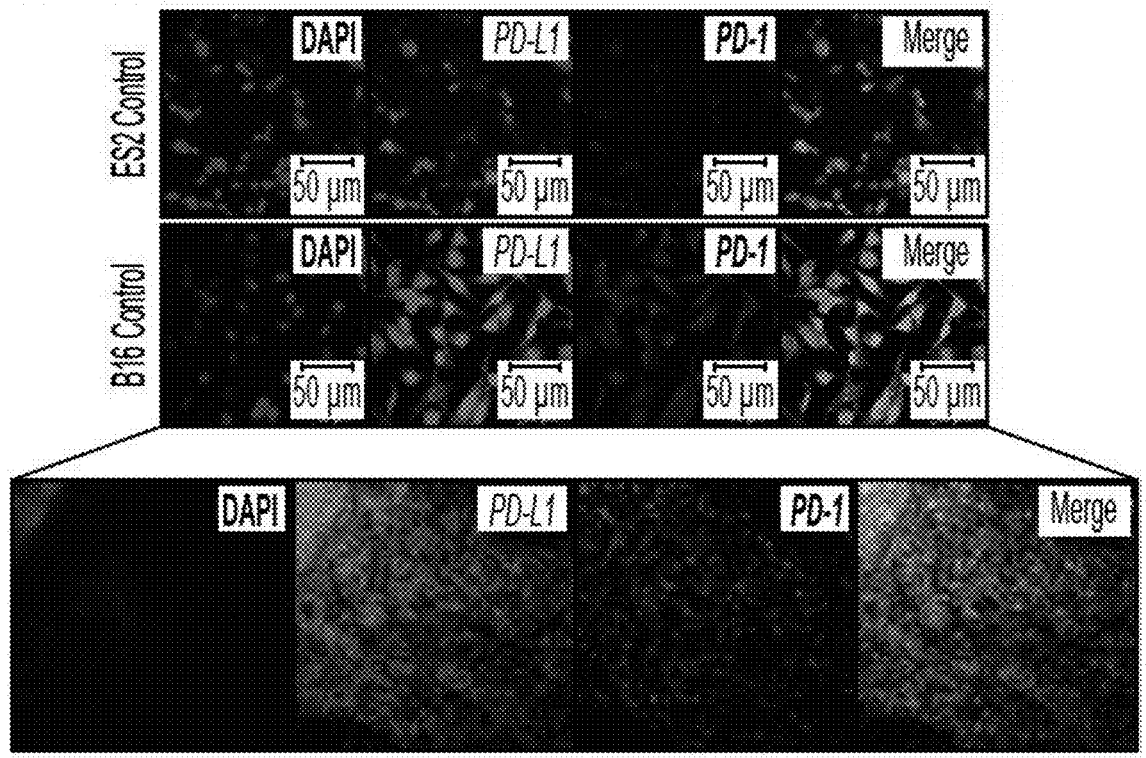
FIGS. 18A-B: PD-1 does not co-localize with PD-L1 in B16 or ES2 cells.
Figure 18B:
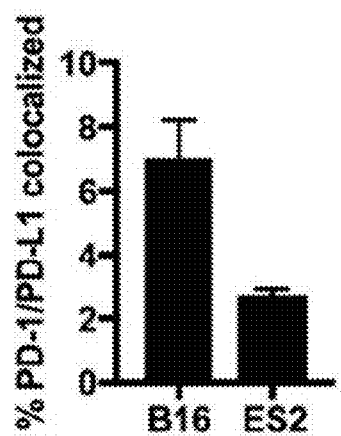
Figure 20:
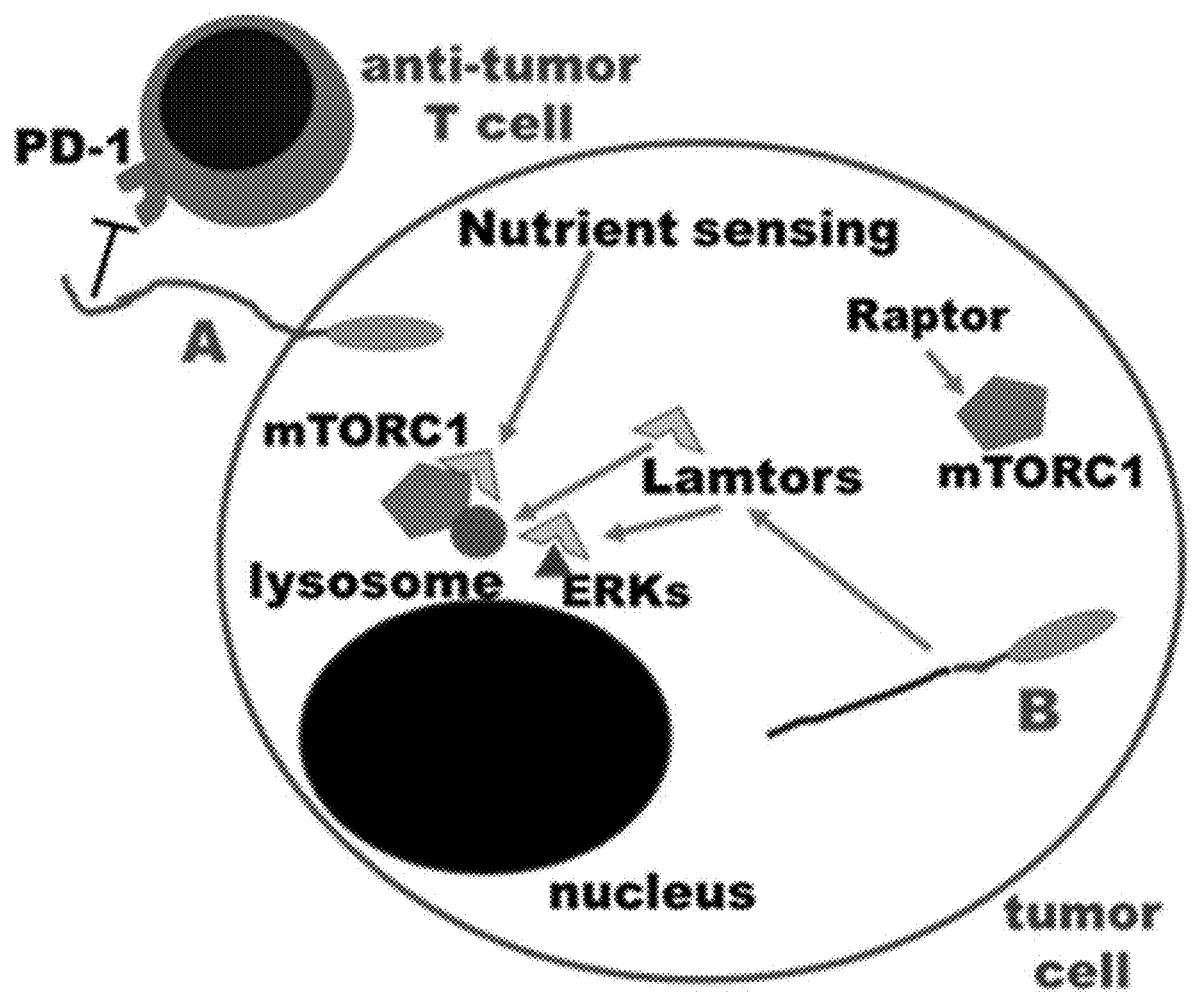
FIG. 20: A model for tumor-intrinsic PD-L1 control of mTORC1 and Lamtors and how that differs from the dogmatic view of tumor surface PD-L1 interactions with T cells. Cytoplasmic PD-L1 drives mTORC1 and other signals for tumor pathology and treatment resistance. Surface PD-L1 has a complex Ig-like N-terminal extracellular structure (blue) attached to a transmembrane domain (red) attached to a short cytoplasmic tail (green). The Ig-like extracellular domain interacts with the Ig-like domain of extracellular PD-1.

In a clinical trial of ovarian cancer patients receiving nivolumab (anti-PD-1), bevacizumab and cyclophosphamide (ClinicalTrials.gov Identifier: NCT02853318), cytoplasmic PD-L1 was measured in tumor biopsies of selected patients as follows. Responders were defined as surviving ≥24 months after treatment initiation before disease progression. Non-responders were defined as surviving <4 months after treatment initiation before disease progression. We tested 3 responder and 3 non-responder ovarian cancer patients. Tumor biopsies were formalin-fixed, paraffin-embedded tumors, cut into 4 micron slices and stained with specific antibodies coupled to barcoded UV-photocleavable oligonucleotides and fluorescent tags from NanoString. Percent surface and cytoplasmic PD-L1 was determined by assessing oligonucleotide location in relationship to tumors in selected regions of interest using FIJI software at 0.325 μm/pixel resolution to map x-y coordinates through the focal plane. Total tumor PD-L1 was determined by Nanostring GeoMx™ Spatial Imaging Platform using mapped x-y coordinates and signal from barcoded oligonucleotides to obtain surface and cytoplasmic data. Total immune cells were identified as CD45+ and total T cells were identified as CD3+. The mean of various signals within 3 regions of interest/patient was assessed by 2-way ANOVA with Tukey's multiple comparisons test. Total CD45$^+$ immune cells and CD3$^+$ T cells increased on treatment in responders but not non-responders as expected (FIG. 17A) supporting assessment validity. At baseline, tumor cytoplasmic PD-L1 was lower in responders versus non-responders. Strikingly, cytoplasmic versus surface PD-L1 fell significantly, whereas it rose significantly in non-responders (FIG. 17B) more easily seen as the significant drop in cytoplasmic/surface ratio in responders versus a significant increase in non-responders (FIG. 17C) whereas total tumor PD-L1 was essentially unchanged and predicted neither treatment response nor immune cell content. Finally, cytoplasmic PD-L1 negatively predicted CD3$^+$ T cell increase on treatment (R=−0.88, p=0.004), Without wishing to be bound by any theory, the data supports the proposed mechanism of action of tumor cytoplasmic PD-L1 shown in FIG. 18. Cytoplasmic PD-L1 drives mTORC1 and other signals for tumor pathology and treatment resistance. The data provided herein shows that important tumour immunopathology and treatment resistance mechanisms can be driven distinctly by cytoplasmic versus surface PD-L1 and Lamtor expression. This evidence requires a re-thinking of the current paradigm focused on surface-expressed PD-L1 interactions with T cells, and suggests novel treatment approaches and response biomarkers in ovarian cancer and melanomas. It is anticipated that these actions of cytoplasmic PD-L1 may affect a wide variety of or all of cancers that express PD-L1.

Example 6

Tumor PD-L1 Promotes the ATM/Chk2 DDR Signaling Axis.

Figure 28:
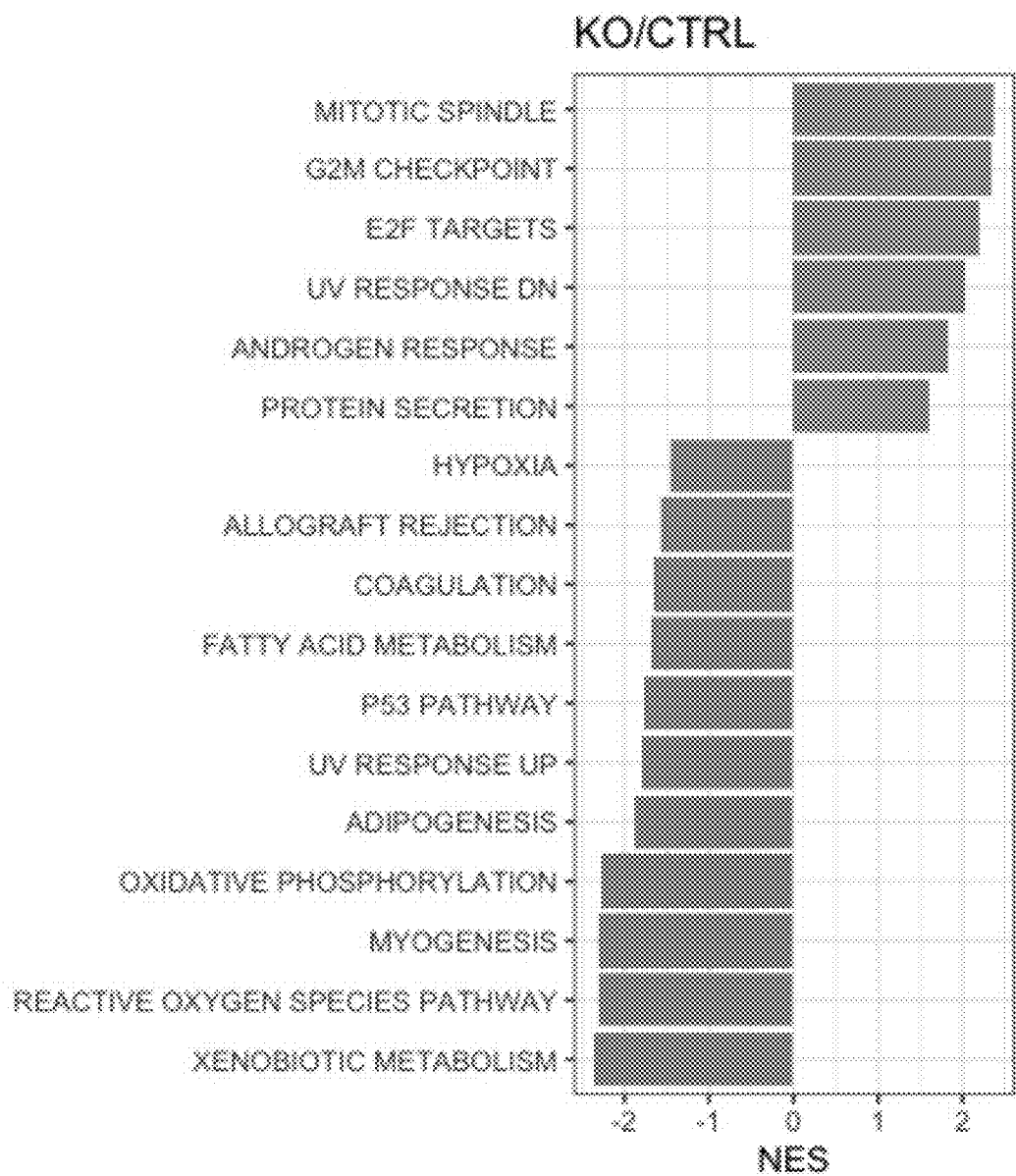
FIG. 28: RNA-seq identifies several differentially expressed pathways dependent on tumor PD-L1.
Figure 29A:
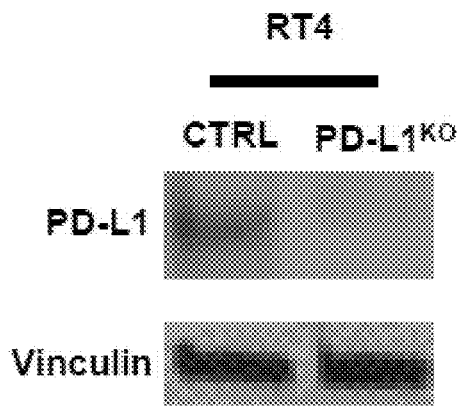
FIGS. 29A-E: PD-L1 promotes gemcitabine chemoresistance and suppresses DNA damage accumulation in RT4 bladder cancer cells.
Figure 29B:
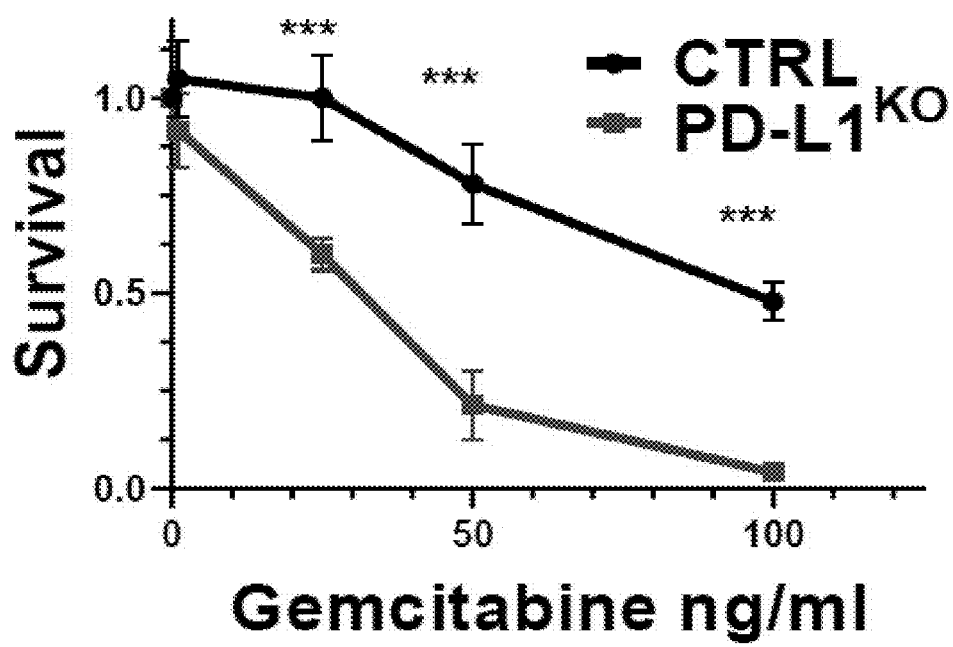
Figure 29C:
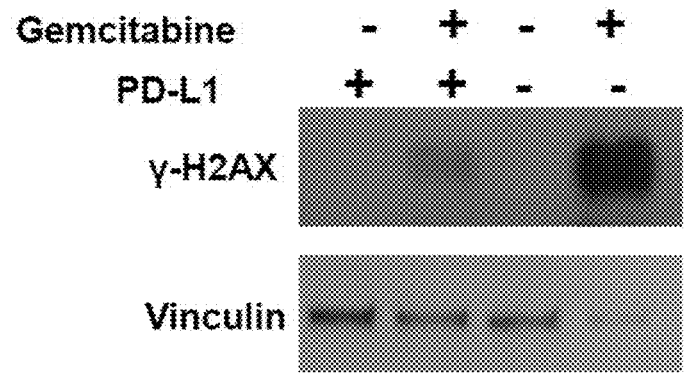
Figure 29D:
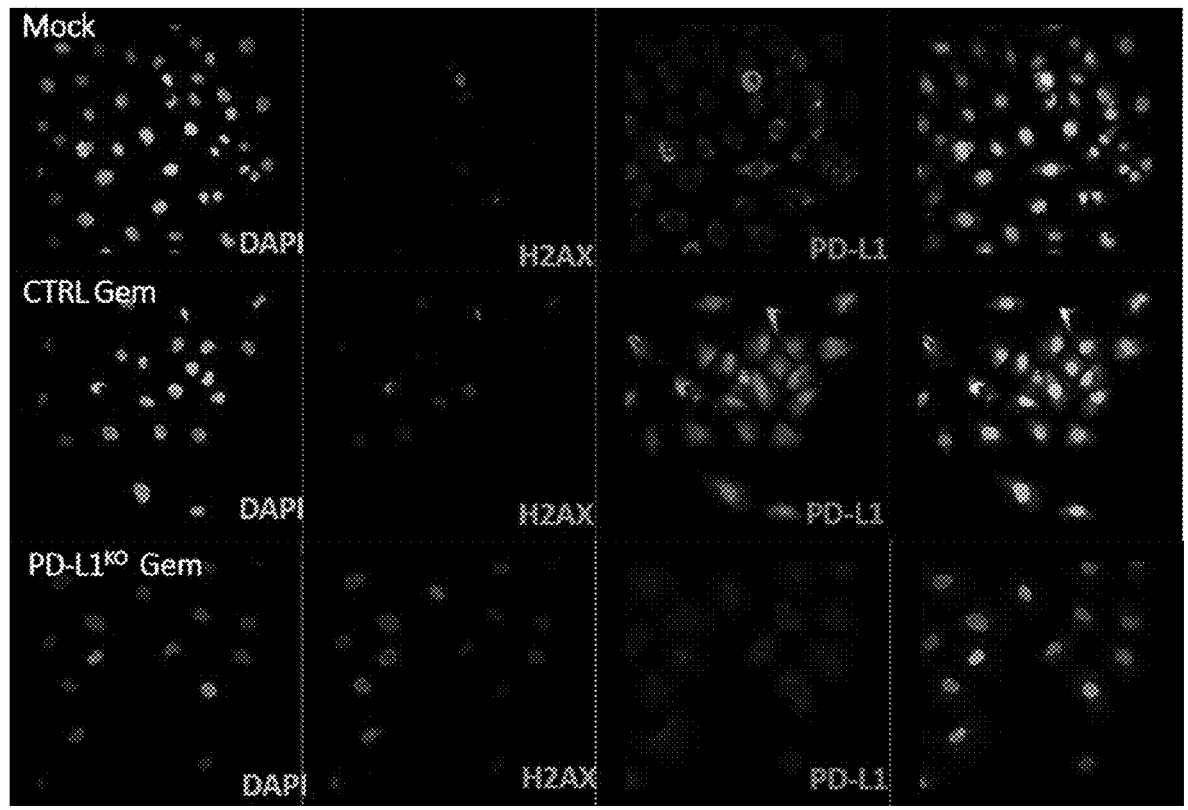
Figure 29E:
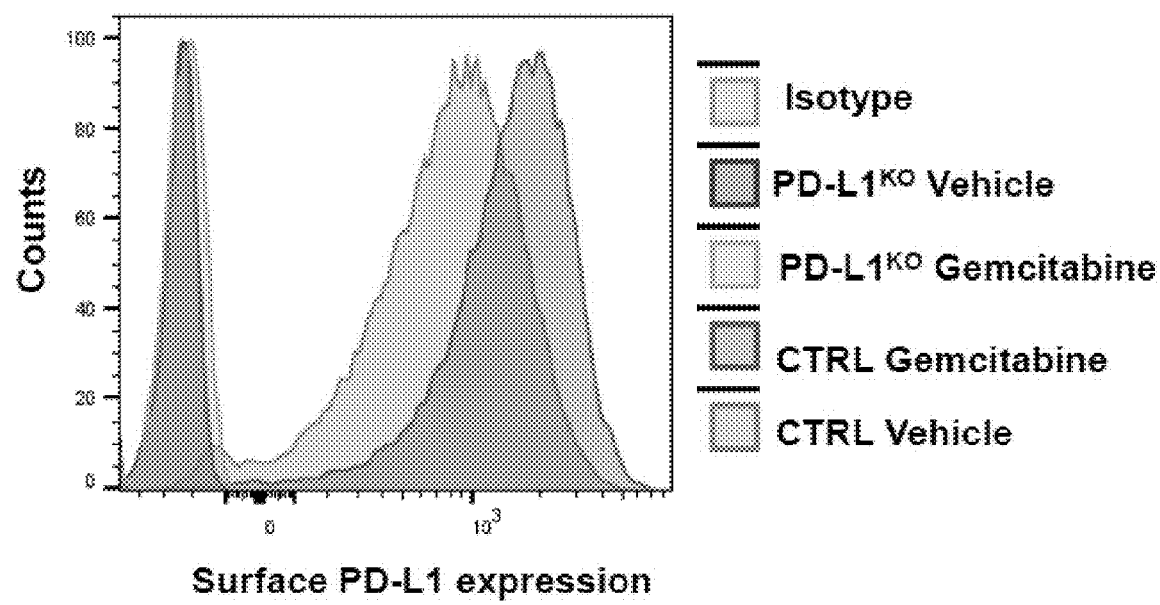

Tumor-intrinsic PD-L1 control of critical canonical pathways including mTORC1 has been observed in melanoma and ovarian cancer (Clark et al., 2016). To identify additional tumor-intrinsic signaling pathways altered by PD-L1, PD-L1 knockout (PD-L1$^{KO}$) B16-F10 murine melanoma cells were generated using CRISPR/Cas9 genome engineering and respective PD-L1 replete controls (CTRL). RNA-sequencing (RNA-seq) of gene transcripts in CTRL versus PD-L1$^{KO}$ B16-F10 identified multiple pathways by Gene Set Enrichment Analysis influenced by tumor PD-L1 silencing including DDR checkpoints as a top altered hit (FIG. 28). Following DNA damage, eukaryotic cells rely most significantly on the ATM/Chk2 and ATR/Chk1 DDR signaling axes to initiate effective DNA repair and promote cellular survival. Interrogation of these central axes by immunoblotting identified a specific reduction of total Chk2 expression in PD-L1$^{KO}$ cells without significant alteration of total ATM, ATR, or Chk1 (FIGS. 21A-B). Consistent with an impaired ATM/Chk2 DDR axis, PD-L1 silencing resulted in accumulation of DNA damage under homeostatic conditions measured by γH2AX nuclear foci, a marker of DNA double stranded breaks (FIGS. 1A, C-D), supporting the idea that tumor PD-L1 can suppress cell stress from endogenous sources of DNA damage.

Although tumor PD-L1 can promote resistance to DNA damaging agents such as cytotoxic chemotherapy or radiation (Fujita et al., 2015; Wu et al., 2018; Cao et al., 2019), specifics of tumor-intrinsic PD-L1 control of specific DDR pathways remain unknown. The RT4 human bladder cancer cell line that has recapitulated many cell-intrinsic PD-L1 signaling properties (Clark et al., 2016) was utilized. Following gemcitabine exposure, a standard-of-care cytotoxic chemotherapeutic (von der Maase et al., 2000; Messing et al., 2018), PD-L1$^{KO}$ RT4 cells exhibited substantially lower viability compared to CTRL cells, and accumulated more γH2AX by immunoblotting corroborated by confocal imaging of γH2AX nuclear foci (FIGS. 29A-D), in line with a recent report in breast and colon cancer cells (Tu et al., 2019). Genetic PD-L1 silencing potently reduced total Chk2 following gemcitabine treatment but not ATM, ATR, or Chk1. Consistent with total Chk2 reduction, the inventors observed markedly reduced phosphorylated Chk2 (Thr-68) in PD-L1$^{KO}$ RT4 cells confirming an impairment in DNA damage-induced Chk2 activation (FIGS. 21E-F). The ATM/Chk2 pathway can play an important role in nuclear DNA double strand break repair (Stolz et al., 2010; Zhang et al., 2004). Consistent with reduced nuclear Chk2 in PD-L1$^{KO}$ cells versus CTRLs, PD-L1 deficiency delayed X-ray induced DNA repair kinetics measured by time to recovery of γ-H2AX foci (FIGS. 21G-H). Without wishing to be bound by any theory, these data support the idea that tumor-intrinsic PD-L1 is a regulator of the DDR, under both homeostatic and following exogenous DNA damage, by supporting Chk2 expression.

Example 7

Figure 30A:
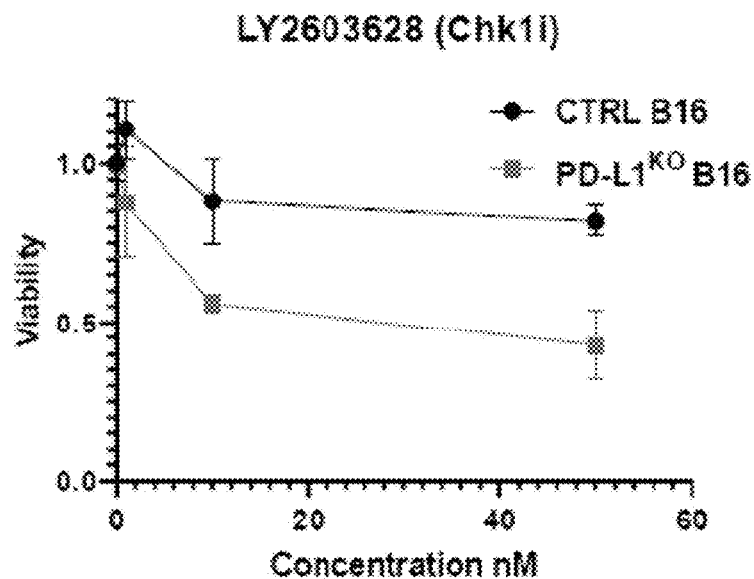
FIGS. 30A-F: Genetic PD-L1 targeting in human and mouse tumor lines enhances ATR/Chk1i synthetic lethality.
Figure 30B:
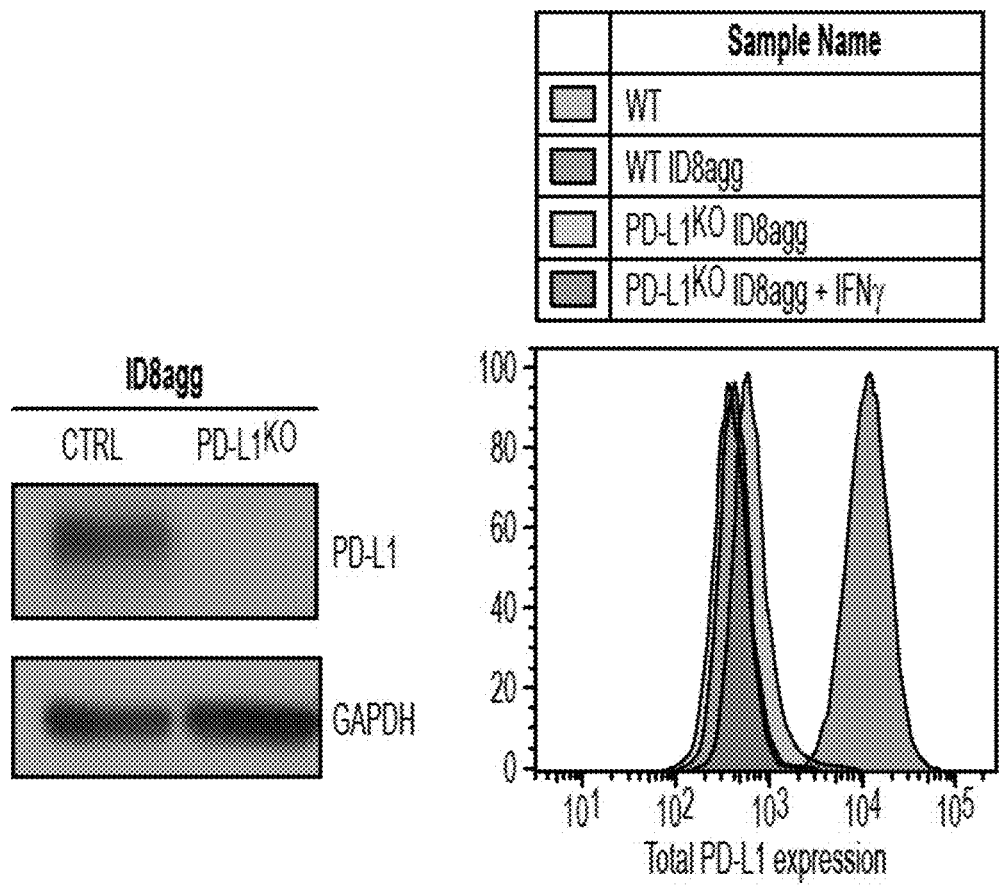
Figure 30C:
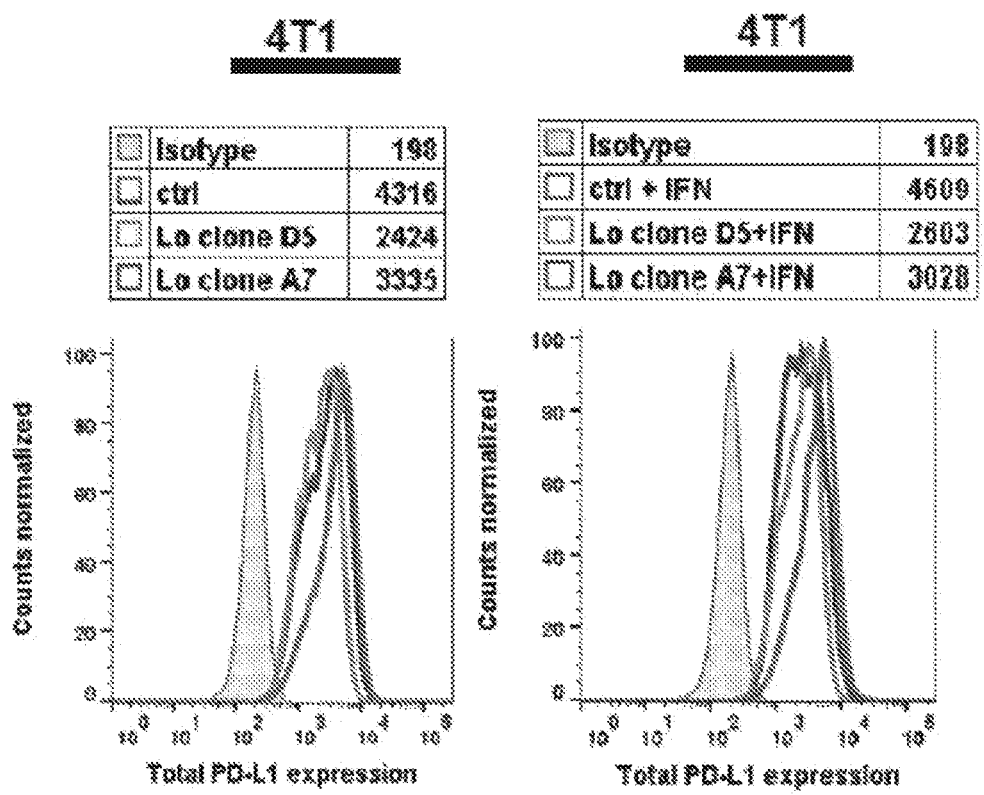
Figure 30D:
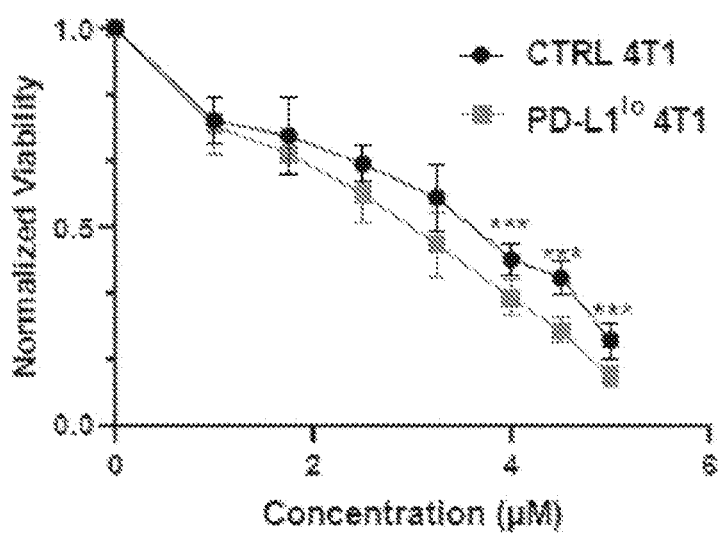
Figure 30E:
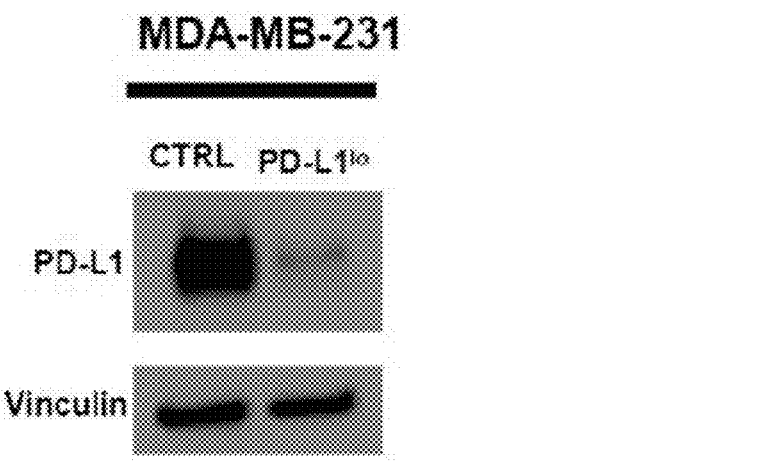
Figure 30F:
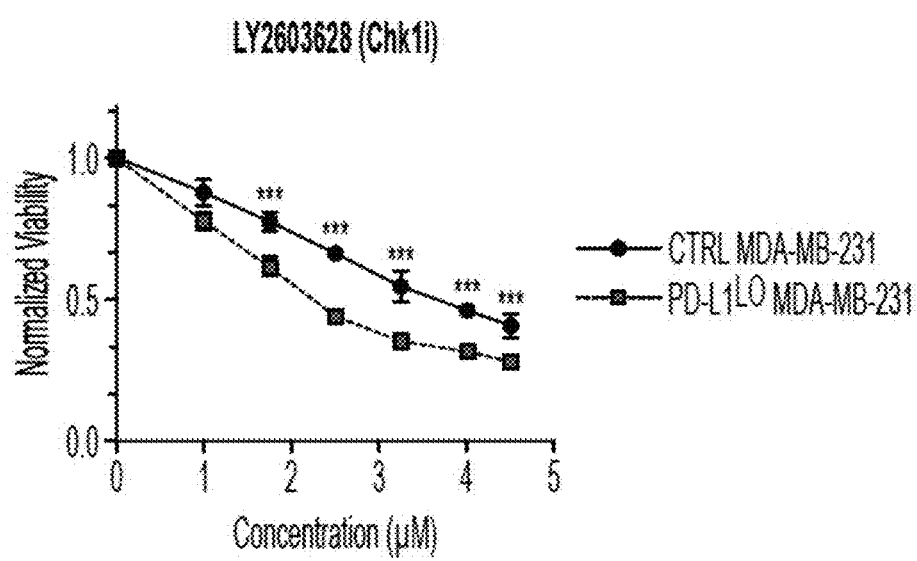

Genetic PD-L1 Targeting Enhances ATR/Chk1 Inhibitor Synthetic Lethality In Vitro and In Vivo Although the ATM/Chk2 and ATR/Chk1 DDR axes are distinct, they share overlapping and compensatory capabilities under certain conditions. Impairment of Chk2 in PD-L1$^{KO}$ B16-F10 cells was accompanied by increase in phosphorylated ATR (Ser-428) and phosphorylated Chk1 (Ser-345) (FIG. 21B) suggesting increased reliance on activated ATR/Chk1 pathway signals to cope with DNA damage in PD-L1 deficient cells. The inventors hypothesized that simultaneously disrupting the ATR/Chk1 pathway using DDRi in PD-L1 deficient cells could induce synthetic lethality. Consistent with observed DDR defects (FIGS. 21A-H), striking cytotoxicity in PD-L1$^{KO}$ versus CTRL RT4 and B16 cells treated with the highly selective Chk1i, rabusertib (LY2603618) in vitro (FIG. 22A and FIG. 30A) was observed. PD-L1$^{KO}$ cells were significantly less sensitive to the ATRi, AZD6738 (FIG. 22B) but not to the ATMi AZD0156 (FIG. 22C) supporting the importance of the ATR/Chk1 axis for cell survival during tumor PD-L1 deficiency. The consequences of genetic PD-L1 depletion on ATRi or Chk1i synthetic lethality were further tested in murine 4T1 triple negative breast and ID8agg ovarian cancer cells on the Balb/c and BL6 genetic backgrounds, respectively. Notably, these tumors are resistant to αPD-L1 immune checkpoint blockade immunotherapy despite expressing PD-L1. PD-L1 knockdown by shRNA (PD-L1$^{lo}$) in 4T1 and PD-L1 deletion by CRISPR/Cas9 (PD-L1$^{KO}$) in ID8agg enhanced sensitivity to Chk1i or ATRi versus respective CTRLs in vitro (FIGS. 22D-F and FIGS. 30B-D) and confirmed with clonogenic assays (FIGS. 22G-H), consistent with RT4 effects. Also consistent with mouse 4T1 Chk1i sensitivity, PD-L1$^{lo}$ human MDA-MB-231 triple negative breast cancer cells were more sensitive versus CTRL to Chk1i in vitro (FIGS. 30E-F). To demonstrate further that targeting intracellular PD-L1 improves Chk1i synthetic lethality even in the absence of anti-tumor immunity, we challenged NOD.SCID γc-deficient (NSG) mice with control or PD-L1$^{lo}$ 4T1 cells and treated with rabusertib. PD-L1$^{lo}$ but not CTRL 4T1 tumors in severely immunodeficient NSG females were particularly sensitive to single agent rabusertib treatment (FIGS. 22J-L). These results show that tumor PD-L1 depletion can improve synthetic lethality with ATR inhibition and increase potently with Chk1 inhibition in multiple human and mouse tumor cell lines on distinct major histocompatibility complex backgrounds in vitro and in vivo. Tumor PD-L1 status can be used a predictive biomarker for DDRi efficacy.

Figures 31A, 31B, 31C:
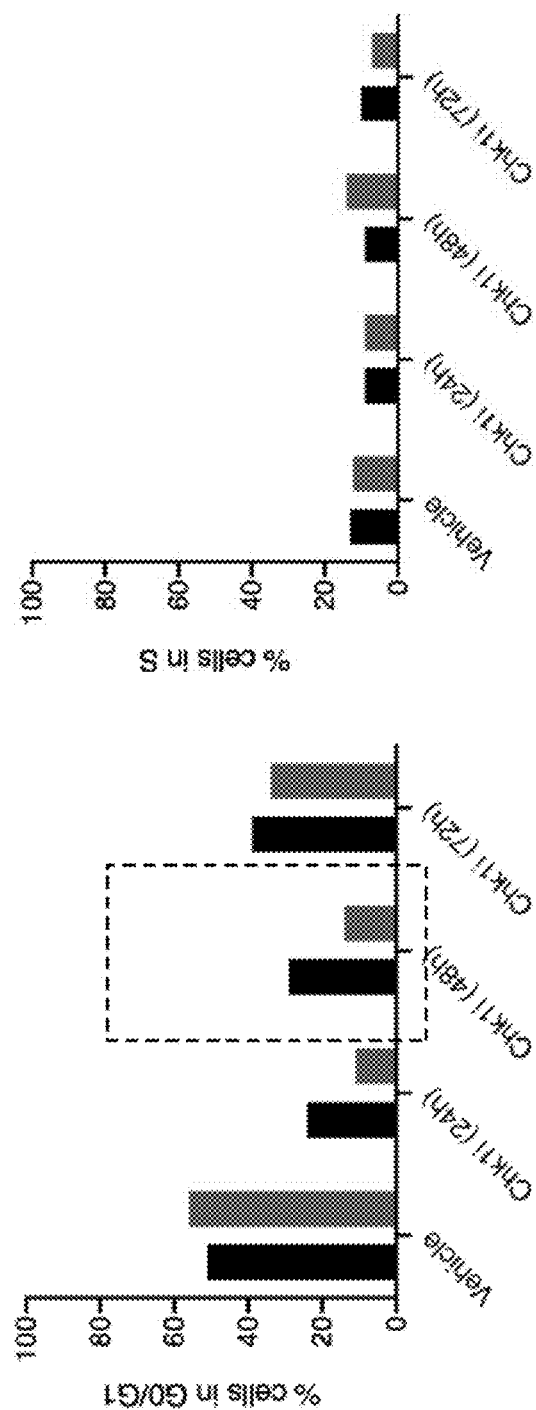

Chk1 and Chk2 are structurally distinct proteins but can exhibit functional cross talk to prevent endogenous DNA damage accumulation from DNA replication and promote the crucial G2M cell cycle checkpoint to allow sufficient time for DNA repair (Zaugg et al., 2007; Bartek & Lukas, 2003; Niida et al., 2010; Wang et al., 2020). Consistent with loss of multiple DNA damage checkpoint mediators, increased accumulation of PD-L1 deficient cells in G2M and fewer cells in G0/G1 relative to CTRL following Chk1i treatment (FIGS. 31A-C) were observed. The G2M checkpoint may be important for Chk1i sensitivity (Li et al., 2020; Parmar et al., 2019). A reverse protein array (RPPA), a sensitive technique to detect multiple phospho-proteins simultaneously, was performed in PD-L1$^{KO}$ versus CTRL cells following Chk1i treatment in vitro. PD-L1 replete, CTRL cells exhibited robust activation of p-Chk2 (Thr-68) while PD-L1$^{KO}$ cells instead accumulated more DNA damage measured by γ-H2AX (FIG. 31D) implicating the importance of Chk2 functionality for cell survival upon challenge with Chk1i in PD-L1 replete cells.

To determine whether tumor PD-L1 regulation of Chk2 content was responsible for enhanced Chk1i synthetic lethality, re-expression of Chk2 in PD-L1$^{KO}$ cells was forced under a constitutively active promoter. Chk2 knock-in (Chk2$^{KI}$) fully reversed Chk1i synthetic lethality in PD-L1$^{lo}$ 4T1 cells and partially restored it in PD-L1$^{KO}$ RT4 cells (FIGS. 23H-I). Chk2$^{KI}$ improved DDR signaling, and γH2AX accumulation following Chk1i, and Chk2 protein was fully restored to parental levels in both tumors (FIGS. 23J-K). The partial reversal of synthetic lethality from Chk1i in RT4 PD-L1$^{KO}$ suggests either a requirement for some PD-L1 availability to inhibit Chk1i synthetic lethality, or additional mechanisms that could reflect the specific mutational landscapes of distinct tumors. In contrast to a prior report investigating alternative mechanisms for Chk1i sensitivity (Pfister et al., 2015), the inventors did not observe significant changes in ribonucleotide reductase content, an important mediator of DNA replication stress (FIG. 31E) following PD-L1 depletion. However, the CDK4/6 inhibitor Palbociclib, which inhibits Rb activation (Witkiewicz et al., 2018), partially reversed Chk1i sensitivity in PD-L1$^{KO}$ significantly greater than control RT4 (FIG. 31F), suggesting Rb signals could be involved in PD-L1-dependent Chk1i sensitivity. Thus, tumor PD-L1 could be considered along with other known biomarkers of Chk1i sensitivity including tumor Rb or p53 status (Witkiewicz et al., 2018; Ma et al., 2012). Nonetheless, these data show the importance of PD-L1-dependent Chk2 regulation for effective DDR.

Example 8

Intracellular but not Surface PD-L1 Restores Chk2

The inventors next sought to understand the mechanism for tumor PD-L1 regulation of Chk2 content. PD-1 is a major PD-L1 receptor (Dong et al., 1999) central to the PD-L1/PD-1 canonical signaling axis that can affect immune checkpoint blockade immunotherapy, but PD-1 can also mediate tumor intracellular PD-L1 signaling (Kleffel et al., 2015; Wang et al., 2020). The inventors observed PD-1 expression on B16-F10 and considered whether PD-L1 effect on Chk2 was dependent on PD-1. However, in PD-1$^{KO}$ B16-F10 cells (CRISPR/Cas9) γ-H2AX and ATM/Chk2 signals were unaffected versus CTRL cells (FIG. 23A). Similarly, genetic PD-1 knockdown by short hairpin RNA (shRNA) or anti-PD-1 treatment (PD-1 blocking antibodies) failed to enhance Chk1i sensitivity in vitro in RT4 cells (FIGS. 32A-B) that contain functional PD-1 signals (Zhang et al., 2021). Without wishing to be bound by any theory, these results support the idea that PD-L1 control of Chk2 does not require PD-1.

PD-L1 is distributed throughout cell surface, cytoplasm, and nucleus (Burr et al., 2017; Mezzadra et al., 2017; Gao et al., 2020; Hou et al., 2020) and as observed in FIG. 29D. Nonetheless, specific intracellular signals ascribed to either surface or intracellular PD-L1 has not been clearly delineated. Subcellular PD-L1 location effects on Chk2 were tested. Using PD-L1$^{KO}$ B16-F10 cells, PD-L1 was re-expressed to be retained intracellularly (PD-L1$^{cyto}$) by introducing an N-terminal myristoylation tag or only on the surface (PD-L1$^{surf}$) using a commercially available surface display vector (FIG. 23B). Immunoblotting confirmed that PD-L1$^{cyto}$ cells demonstrated PD-L1 essentially in the cytoplasmic fraction while PD-L1$^{surf}$ cells exhibited PD-L1 essentially in the plasma membrane fraction (FIG. 23C). Further validation by confocal imaging demonstrated a membranous pattern of staining in cells transfected with the PD-L1$^{surf}$ vector versus an intracellular staining pattern when transfected with PD-L1$^{cyto}$ (FIG. 32C-D). To gain a global understanding of the impact of PD-L1 subcellular distribution on tumor-intrinsic signaling consequences, we performed RNA-seq on B16-F10 PD-L1$^{KO}$ stably transduced with either PD-L1$^{surf}$ or PD-L1$^{cyto}$. PD-L1$^{surf}$ compared to PD-L1$^{cyto}$ mediated a distinct gene-expression profile by hierarchical clustering analysis and GSEA analysis of top altered pathways (FIGS. 23D-E). A GSEA signature associated with G2M checkpoints was more enriched in PD-L1$^{cyto}$ (NES=2.7, FDR=4e10$^{-20}$ vs. NES=1.53, FDR=0.012) while a GSEA signature associated with epithelial to mesenchymal signature was significantly enriched in PD-L1$^{surf}$ (FIGS. 23F-G). These results support the idea that the specific subcellular tumor PD-L1 location can drive specific cellular pathways.

The inventors next investigated the subcellular PD-L1 effect on Chk2 expression. PD-L1$^{surf}$ did not restore Chk2 protein content, reduce γH2AX or reverse rabusertib synthetic lethality, whereas remarkably, PD-L1$^{cyto}$ had all these consequences (FIG. 23H). Surface-specific PD-L1 enhanced vimentin expression, an epithelial mesenchymal transition marker, distinctly from PD-L1$^{cyto}$ (FIG. 23H) and consistent with RNA-seq (FIG. 23G), thus confirming a surface-specific PD-L1 function. Intracellular PD-L1 was observed to be sufficient to affect signals and functions including control of the ATM/Chk2 DDR pathway, whereas surface PD-L1 was observed to be not required, although it may mediate distinct tumor-intrinsic signals and functions.

Example 9

PD-L1 Controls Chk2 Protein Content in Lysosomes

Given that intracellular PD-L1 was observed to be important for regulation of Chk2 expression, the inventors investigated if tumor PD-L1 could directly promote Chek2 by regulating its mRNA stability (Tu et al., 2019) or act as a nuclear co-transcription factor (Gao et al., 2020; Hou et al., 2020) as previously reported. We assessed Chek2 transcripts in CTRL and PD-L1$^{KO}$ B16-F10 cells and found no significant difference in RNA-seq datasets (FIG. 24A). To corroborate this finding, PD-L1 elimination also had no obvious effect on Chek2 mRNA levels by qRT-PCR at baseline or following DDRi (rabusertib) treatment (FIG. 24B). Tumor PD-L1 depletion suppresses mTORC1 activation (Clark et al., 2016; Chang et al., 2015). Since mTORC1 can enhance mRNA translation, the inventors assessed whether PD-L1 dependent mTORC1 activation regulated Chk2 content. Neither the mTORC1 inhibitor, rapamycin nor genetic knockdown of Raptor by short-hairpin RNA (Raptor$^{lo}$), the principal component of the mTORC1 complex, affected Chk2 protein content in B16-F10 cells (FIG. 24C). Using the cycloheximide chase assay for protein stability, Chk2 half-life, but not ATM half-life, was greatly reduced by PD-L1 deficiency (FIGS. 24D-E). Thus, tumor PD-L1 regulates specific proteins post-translationally that can affect cellular stress responses. Treatment of PD-L1$^{KO}$ but not CTRL B16-F10 cells with the lysosome inhibitor Bafilomycin A1 led to Chk2 accumulation (FIGS. 24A-G) suggesting PD-L1 dependent promotion of Chk2 stability may occur by suppressing lysosomal mediated degradation. In support of lysosomal degradation, live cell imaging showed that PD-L1 and Chk2 co-localized with each other, especially in lysosomes

Example 10

PD-L1 Control of Chk2 is PD-L1 Tail-Independent

PD-L1 intracellular effects have been entirely attributed to its short (30 amino acid) cytoplasmic tail (Tu et al., 2019; Gao et al., 2020; Hou et al., 2020; Gato-Canas et al., 2017). To elucidate mechanisms for tumor PD-L1 control of Chk2 further, expression constructs encoding RFP-tagged full-length PD-L1 (PD-L1$^{full}$, aa 1-290), PD-L1 lacking only the c-terminal cytoplasmic tail (PD-L1$^{del.tail}$, aa 1-260), or the PD-L1 cytoplasmic tail only (PD-L1$^{tail}$, aa 260-290) were generated. These constructs were transfected into PD-L1$^{KO}$ B16 F-10 cells and expressed effectively at the expected size and cellular locations by immunoblotting and confocal imaging (FIGS. 25A-B, see methods). Both PD-L1$^{full}$ and PD-L1$^{tail}$ restored Chk2 content whereas PD-L1$^{tail}$ did not, consistent with a transcriptional/post-transcriptional independent mechanism of gene regulation (FIG. 25C). Co-immunoprecipitation suggested a physical PD-L1/Chk2 interaction (FIG. 25D), basally and following DNA damage stress, that was also consistent with the requirement for cytoplasmic PD-L1 for Chk2 control (FIGS. 23A-H). These data show a tail independent PD-L1 function in controlling Chk2 protein through post-translational stability and suggest a direct participation of intracellular PD-L1 in the DDR.

Example 11

De Novo Induced PD-L1KO Tumors Phenocopy CRISPR/Cas9 PD-L1KO of Established Tumors Intracellular PD-L1 signals have compared effects of genetic PD-L1 depletion in established tumor cells versus PD-L1-replete established CTRL cells. The inventors questioned if PD-L1 signals effects from such methods actually reflected underlying signaling, or instead reflected consequences of PD-L1 loss from a PD-L1-replete tumor cell. A model in which mice lack PD-L1 only in melanocytes, the melanoma cell-of-origin, was generated by crossing a transgenic mouse with CD274 flanked by LoxP sites with a well-established tamoxifen inducible Tyrosinase: $Cre^{ER}$ $Nras^{Q61R}$/CDKN2A ($TpN^{61R}$) mouse (Burd et al., 2014; Hennessey et al., 2017), to create $CD274^{fl,fl}$ $TpN^{61R}$ mice. PD-L1 null (Nras $CD274^{-/-}$) or PD-L1 replete (Nras CTRL) melanomas are induced in these mice versus littermate controls by tamoxifen induction alone or can be accelerated by UV irradiation (Hennessey et al., 2017). Nras is the most common oncogene in UV-induced melanomas worldwide (Platz et al., 2008; Hennessey et al., 2017). Tumor latency after tamoxifen induction was delayed in $CD274^{fl,fl}$ $TpN^{61R}$ mice compared to littermate controls $TpN^{61R}$ but was equally accelerated by UV irradiation (FIG. 26A), implicating alternative mechanisms for immune evasion aside from PD-L1 in UV-driven melanomagenesis. Tumors were obtained from autochthonous melanomas in mice after UV plus tamoxifen induction and confirmed basal and interferon-gamma inducible PD-L1 expression in Nras $CD274^{+/+}$ versus $CD274^{-/-}$ cells (FIG. 26B). Induced PD-L1$^{KO}$ tumors had defective Chk2 expression, increased YH2AX and exhibited synthetic lethality to the selective Chk1 inhibitors rabusertib and prexasertib in vitro (FIGS. 26D-E) consistent with genetic PD-L1 depletion in established tumors (FIGS. 22A-O). Tumors were cultivated ex vivo and were used to challenge C57BL/6J wild type mice, and these experiments showed that rabusertib controlled in vivo growth significantly better in PD-L1 null versus PD-L1 replete tumors (FIGS. 26F-H). These data established that PD-L1 effects on ATM/Chk2 DDR and Chk1i synthetic lethality are not from compensatory mechanisms in established PD-L1-expressing following PD-L1 depletion, and further support the notion that tumors with low/negative PD-L1, as is this case with immunologically "cold" tumors (Taube et al., 2012; Ribas et al., 2016), can exhibit superior responses to Chk1i.

Example 12

PD-L1-Driven ATM/Chk2 DDR Exposes an Unexpected αPD-L1 Treatment Vulnerability

The translatable potential of PD-L1-controlled Chk2 expression was shown using small molecule Chk1i inhibitors. αPD-L1 can directly signal to tumor cells to slow growth and metastatic spread in an immune independent manner (Clark et al., 2016). To test αPD-L1 effects on DDR, human RT4 cells were incubated with atezolizumab (FDA-approved αPD-L1) in vitro, which slightly reduced viability in the absence of immune cells as reported (Zhang et al., 2018). Rabusertib, a highly selective Chk1 inhibitor, gave the expected dose-response toxicity but strikingly, αPD-L1 plus rabusertib was essentially 100% lethal in control RT4 cells with no effect on PD-L1KO RT4 cells (FIGS. 27A-B). Immunoblot assessment of atezolizumab plus Chk1i treated CTRL RT4 cells demonstrated reduced Chk2 content and increased DNA damage (FIG. 27C) phenocopying effects seen with genetic PD-L1 depletion (FIGS. 21A-H and FIGS. 22A-O). αPD-L1 also promoted in vitro synthetic lethality with Chk1i (rabusertib) (FIG. 27D) and induced Chk2 depletion in 4T1 cells (FIG. 7E).

To test the translational relevance of in vitro data the inventors first tested whether αPD-L1 could sensitize tumors to Chk1i in vivo in immunocompromised NSG hosts to exclude potential immune effects. Combination of αPD-L1 with rabusertib (a selective Chk1i) significantly decreased highly tumorigenic murine 4T1 tumors in vivo in highly immunodeficient NSG mice (FIG. 27F), consistent with immune-independent effects of tumor PD-L1 targeting. Wild type mice similarly failed to benefit from either agent alone, whereas the combination of αPD-L1 plus rabusertib significantly treated 4T1 tumors suggesting combination treatment is also beneficial in an immunologically intact host (FIGS. 27G-H). Without wishing to be bound by any theory, these findings support the idea that PD-L1 pathway interference, including with αPD-L1, can expose targetable tumor cell-intrinsic DDR treatment vulnerabilities independent from known effects on anti-tumor immunity. These data support the idea that DDR signals can be used to identify treatment-responsive patients.

Example 13

Anti-Cancer Effects of PMEG and Chlorambucil

Materials and Methods

High throughput Screening: B16 PD-L1 RFP cells were treated with 2.5 and 10 µM compounds from the Prestwick and LOPAC Libraries for 48 hours using the Agilent Bravo liquid pipetting platform. Then, cells were washed with PBS, and fixed with 4% paraformaldehyde (Electron Microscopy Sciences, Hatsfield, PA, Cat 15714S) and labeled with 2 µg/ml DAPI, (Molecular Probes, Cat D1306) and 1 µg/ml Cell Mask-Blue (Invitrogen, Cat. H32720). Plates were then imaged using the Operetta High Content Imaging System, Perkin Elmer, Waltham (DAPI and Cell Mask Blue, Ex 360-400, Em 410-480), and the RFP channels (Ex 520-550, Em 560-630) channels. Agents effecting ≥2-fold PD-L1 reduction in the RFP reporter without loss of ≥20% cell viability were candidate PD-L1 depletion agents.

Cell lines and in vitro treatments: Human OVCAR5 were obtained from David Curiel Washington University. Mouse B16-F10 melanoma (herein "B16" for simplicity) and human ES2 ovarian cancer cells were purchased from ATCC (Manassas, VA). ID8agg-luc and PD-L1$^{KO}$ or PD-L1$^{lo}$ ID8agg cells were generated as we described (Derup et al., 2020). All cell lines were negative for *Mycoplasma* in periodic testing using MycoAlert *Mycoplasma* Detection Kits (Lonza, Cat #LT07-318), according to manufacturer directions. Mouse cells were used in passages <5 and maintained in 5% fetal bovine serum (FBS)-containing RPMI-1640 (Roswell Park Memorial Institute, RT4). Human cells were used in passages <5 and maintained in 10% FBS-containing Gibco Dulbecco's Modified Eagle Medium, all supplemented with 1% penicillin/streptomycin, 1% L-glutamate, and 1% 4-(2-hydroxyethyl)-1-piperazineethanesulfonic acid. Cells were treated with chlorambucil (CAMB) for 48 hours in in vitro work shown here.

Cell proliferation and viability assays: Cells (0.5-1×10$^3$) were plated in 96-well plastic culture plates in 100 µL medium and treated with CAMB. Cell viability was determined by a cell counting kit-8 (CCK-8) (Sigma). Absorbance was measured at 450 nm using a BioTek Synergy 2

Multi-Mode Plate Reader. Proliferation was assessed in triplicate in three separate experiments for in vitro all data shown.

Mice and in vivo treatments: Wild-type (WT) C57BL/6 mice NSG were purchased from Jackson Labs (Bar Harbor, ME), bred in our animal facility and used at 7-20 weeks old. All mice were given ad libitum water and food and housed under specific pathogen-free conditions. Mice used here were matched for sex and age in each experiment. $1\times10^5$ control or PD-L1$^{KO}$B16 cells were given subcutaneously (SQ, both sexes). $4\times10^6$ control or PD-L1$^{lo}$ ID8agg cells in log growth phase were given intraperitoneally (females only). B16 tumor growth was measured with Vernier calipers and volume was calculated as (length×width$^2$)/2. Intraperitoneal ID8agg tumor growth was determined by IVIS Lumina Imaging System (Perkin Elmer; Waltham, MA) 15 minutes after i.p. injection of 3 mg of PBS-dissolved d-luciferin K+ (Gold Biotechnology; St. Louis, MO) with 30 second exposures, medium binning, and F/stop=1. Identical regions of interest were drawn over each subject's abdomen and average radiance (photons/see/cm2/sr) was quantified with Living Image software version 4.2. Body weight was measured every week for PD-L1$^{lo}$ ID8agg mice as a surrogate for tumor growth, and tumors were weighed at end-experiment in confirmation. Survival was determined as >1500 mm$^3$ for SQ tumors and distress or >20% mouse weight gain for PD-L1$^{lo}$ ID8agg tumors. Intraperitoneal injection of chlorambucil was given at indicated doses (optimized for each tumor and treatment condition in preliminary assessments not shown) for 3 treatment cycles starting 7 days after tumor cell challenge. Each chlorambucil cycle was 5 consecutive days of a single injection followed by two days of rest. αPD-L1 (clone 10F.9G2) or respective isotype control was injected intraperitoneally at 100 µg/mouse every 5 days starting on day 7 after tumor challenge for times indicated.

Flow cytometry: Mice were sacrificed by cervical dislocation after induction of deep isoflurane anesthesia. ID8agg tumors were collected and cells were stained as described (Derup et al., 2020) using LSR II hardware and analyzed by FACS Diva (BD Bioscience) or Flow Jo software (Flow Jo, LLC). Anti-mouse (clone 10F.9G2) and human (clone 29E.2A3) PD-L1 [both PE/Cy7, Cat #124314 (mouse) 329718 (human)] were matched with isotype control. Apoptosis assessment used Annexin V and propidium iodide (Thermo Scientific) per manufacturer instruction.

Western blotting and immunoprecipitation: To prepare whole cell lysates, cells were harvested and lysed in RIPA (radioimmunoprecipitation assay) buffer plus 1 mM phenylmethylsulphonyl fluoride and Halt protease/phosphatase inhibitor cocktail (Thermo Scientific) at 4° C. Protein concentrations were measured by BCA Protein Assay Kit (Thermo Scientific). Protein was run on precast 4-15% sodium dodecyl sulfate polyacrylamide gels (Bio-Rad), transferred to polyvinylidene fluoride membranes (GE Water and Process Technologies), and then blocked in 5% non-fat milk for 1 hour at room temperature. The membranes were then incubated with 1:1000 diluted primary antibodies against indicated proteins (Cell Signaling). Specific antibody binding was detected by chemiluminescence using Western Lightening Plus regent (Perkin Elmer). Cells for (co) immunoprecipitation experiments were seeded in 15-cm dishes and cultured as described, using 6 million cells per immunoprecipitation reaction. For protein ubiquitination, cells were lysed in denaturing buffer (50 mM Tris-HCl, 0.5 mM EDTA and 1% SDS) followed by heating at 95° C. for 10 minutes and then quenched with 9 volumes of quenching buffer (0.5% Triton X-100, 20 mM Tris-HCl (pH 8.0), 137 mM NaCl, 10% glycerol, 2 mM EDTA). Protease inhibitor cocktail (Roche) was added fresh to all buffers. Cell lysates were incubated on a rotator for 30 minutes at 4° C., and then centrifuged at 20,000 g for 15 minutes at 4° C. Supernatants were subsequently incubated with anti-PD-L1 antibody overnight and processed using Dynabeads Protein G for Immunoprecipitation (Thermo Fisher Scientific). The final eluate was processed and Western blotting was performed.

Quantitative Real-Time Reverse Transcriptase Polymerase Chain Reaction: Total RNA was isolated from homogenized whole lung tissue with Trizol reagent (Invitrogen) according to manufacturer instructions. Subsequently, cDNA was synthesized with 1-2 µg of total RNA using the, SuperScript III reverse transcriptase (Invitrogen). Quantitative PCR (qPCR) was conducted using the Bio-Rad Real-Time PCR System (Applied Biosystems), amplified with transcript-specific primers with SYBR Green (Thermo Scientific), according to manufacturer instructions. Mouse primers were: Tyr, 5'-CTCTGGGCTTAGCAGTAGGC-3' (SEQ ID NO: 1) and 5'-GCAAGCTGTGGTAGTCGTCT-3' (SEQ ID NO: 2); gp100, 5'-ACATTTCATCACCAGCAGGGTGCC-3' (SEQ ID NO: 3) and 5'-ID NO: 4); Trp-2, 5'-AACAAGTGGGTGCTGGCC-3' (SEQ GTCCTCCACTCTTTTACAGACG-3' (SEQ ID NO: 5) and 5'-ATTCGGTTGTGACCAATGGGT (SEQ ID NO: 6); Trp-1, 5' CCCCTAGCCTATATCTCCCTTTT-3' (SEQ ID NO: 7) and 5'-TACCATCGTGGGGATAATGGC-3' (SEQ ID NO: 8); and GPDH, 5'-AACGACCCCTTCATTGAC-3' (SEQ ID NO: 9) and 5'-TCCACGACATACTCAGCAC-3' (SEQ ID NO: 10) as the internal control. Human primers PD-L1, 5'-GCTTTTCAATGTGACCAGCA-3' (SEQ ID NO: 11) and 5'-ATTTGGAGGATGTGCCAGAG-3' (SEQ ID NO: 12). Data were normalized to the endogenous reference gene GAPDH levels by the comparative CT (ΔΔCt) method.

Statistics: Prism software from GraphPad was used for statistical analyses. In bar graphs, data are shown as mean±SEM. We used two-way ANOVA corrected with Bonferroni post-tests to compare repeated means in tumor growth analyses. The log-rank test was used to analyze mouse survival from survival plots generated with the method of Kaplan-Meier. We used an unpaired t-test for other analyses and considered P<0.05 as statistically significant.

Results

Figure 33D:
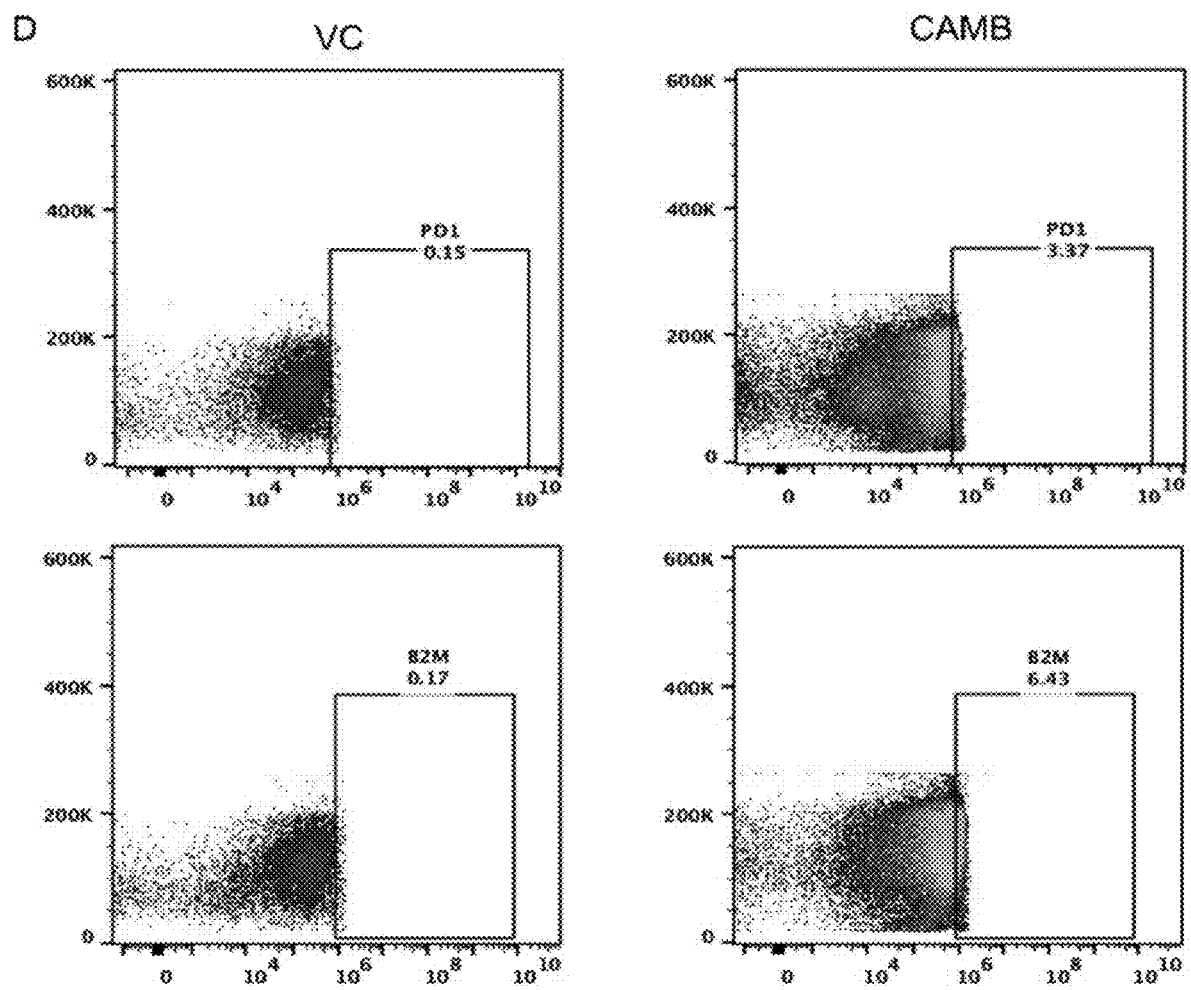

Chlorambucil (CAMB) reduces tumor cell PD-L1 in vitro: To validate PD-L1 depletion from candidates identified by high throughput drug screening, immunoblots were used (FIGS. 33A-B). Next, PD-L1 depletion effects of CAMB in vivo were examined. In ID8agg challenge, CAMB reduced tumor PD-L1 in ascites (FIG. 33C). Upregulation of PD-1 and β2M on the cell surface by chlorambucil was observed (FIG. 33D).

Figure 34A:
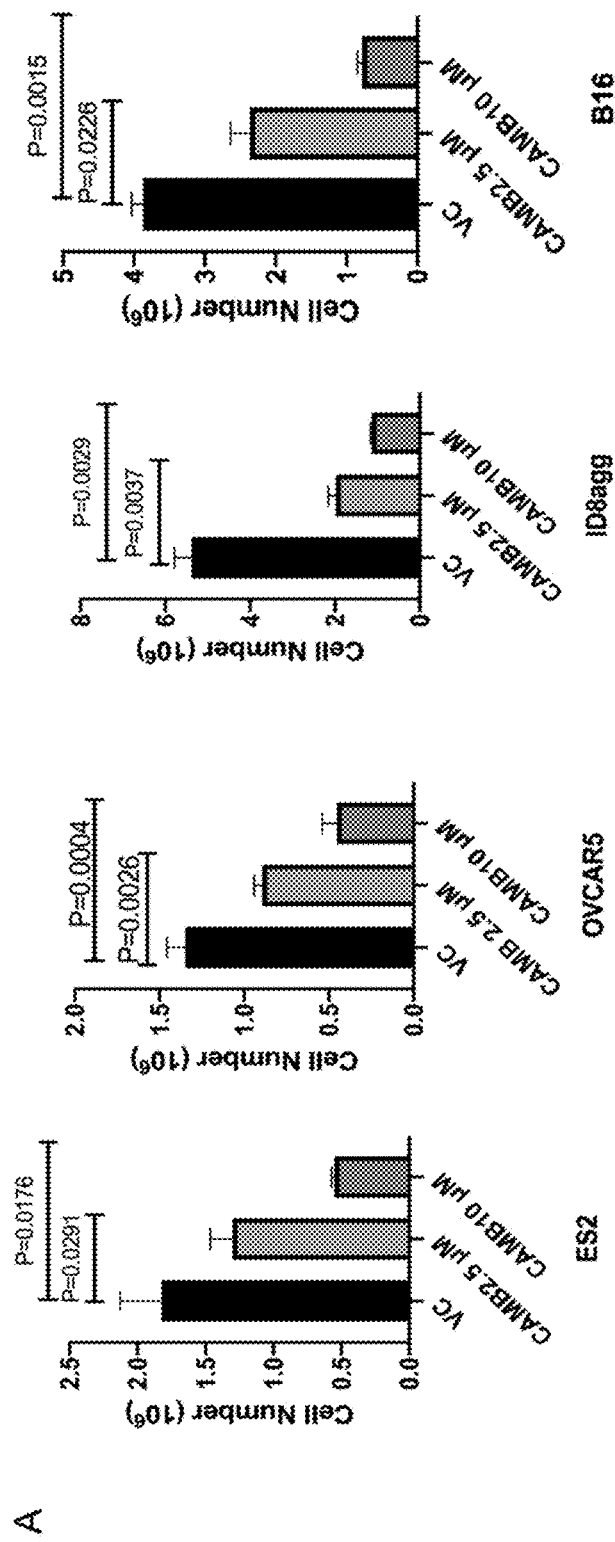

CAMB slows in vitro tumor cell growth without inducing apoptosis: Chlorambucil inhibited cell growth in vitro with little or no killing (FIG. 34A) or apoptosis (FIG. 34B). Immunogenic cell death (ICD) is a type of tumor cell death which plays a major role in stimulating anticancer immune response (Apetoh et al., 2020). Cell surface calreticulin, a measure of ICB was significantly increased by CAMB (FIG. 34C). Interestingly, compared with PD-L1$^{lo}$ or PD-L1$^{KO}$ cells, CTRL cells were more sensitive to CAMB (FIG. 34D). These data indicate that CAMB inhibits cell growth in a tumor PD-L1-dependent manner.

Chlorambucil is a DNA-damaging agent, and DNA damage is usually associated with increased PD-L1. It did not seem likely that cells we studied all had an aberrant PD-L1 response to DNA damage. We thus damaged DNA with X-rays, gemcitabine or rabusertib. These DNA damaging agents increased PD-L1, confirming the selective capacity of chlorambucil to reduce PD-L1 independent of its FDA-approved mechanism of action (FIGS. 34A-D).

CAMB inhibits tumor growth in vivo: Wild type mice were challenged with ID8agg cells and treated with CAMB, which significantly reduced tumor volume and prolonged mouse survival (FIGS. 35A-B). Similar data was observed in B16 challenge into wild-type (WT) mice. To test immune requirements, severely immunodeficient NSG mice were challenged with either ID8agg or B16, and found that chlorambucil effectively treated both (FIGS. 35E-F) similar to effects in wild type mice.

CAMB efficacy in vivo depends on tumor PD-L1 expression: WT mice were challenged with PD-L1-depleted PD-L1$^{lo}$ tumors to test tumor PD-L1-dependence for CAMB efficacy as PD-L1$^{KO}$ ID8agg forms tumors very poorly in WT mice. CAMB at the dose and schedule as for ID8agg was unable to suppress PD-L1$^{lo}$ ID8agg growth (FIG. 35D), suggesting that CAMB-mediated tumor growth inhibition depends on tumor PD-L1 expression. Consistent with ID8agg tumor challenge data, CAMB treatment efficacy was significantly reduced in PD-L1$^{KO}$ B16 challenge into WT mice (FIGS. 35G-I). These data are consistent with the concept that tumor PD-L1 dependence on CAMB treatment independent of tumor type or anatomic location.

CAMB improves αPD-L1 treatment in vivo: Anti-PD-L1 was been shown as ineffective against ID8agg challenge (Derup et al., 2020). Nonetheless, CAMB sensitized ID8agg to αPD-L1 at a CAMB dose that was ineffective as a single agent (FIG. 36A). The inventors then tested if CAMB could also sensitize PD-L1$^{lo}$ ID8agg to αPD-L1. The combination of CAMB plus anti-PD-L1 effectively treated PD-L1$^{lo}$ and PD-L1$^{KO}$ ID8agg tumors in WT mice (FIGS. 36C-F). These data suggested that although CAMB efficacy as a single agent could be immune-independent, immunity could also contribute to combination efficacy. We found that chlorambucil induced ICD independent of tumor PD-L1 status, which could improve anti-PD-L1 efficacy against control or PD-L1-depleted tumors. Further, CAMB did not induce apoptosis, which is not immunogenic, in ID8agg or B16 cells (FIG. 36B). Thus CAMB could promote treatment αPD-L1 efficacy through PD-L1-independent tumor immunogenicity induction.

CAMB plus αPD-L1 enhance anti-tumor immunity: To test immune effects in vivo we performed immune analyses by FACS. In ID8agg tumors, CAMB plus αPD-L1, but not either single treatment, significantly increased tumor-infiltrating activated CD8$^+$ T cells (FIG. 37A, left panel) with enhanced IFN-γ production (FIG. 5A, right panel). This combination of CAMB and anti-PD-L1 additively increased CD44$^+$CD62L$^-$ effector memory and CD44$^+$CD62L$^+$ central memory T cells. Naïve T cells were unchanged (FIG. 37B). In PD-L1$^{KO}$ B16 tumors, the combination increased CD8+ T cells and reduced PD1+CD8+ T cells (FIG. 38A). In agreement with the effect on tumor regression, co-treatment of CAMB and anti-PD-L1 induced significant NK cell increase with a less exhausted phenotype (FIG. 38B) and a decrease in CD11b$^+$CD3$^-$ myeloid cells in the tumor microenvironment (FIG. 38C).

CAMB promotes PD-L1 degradation through the ubiquitin-proteasome pathway: To understand how CAMB reduced PD-L1 content we first assessed transcription. PD-L1 mRNA in OVCAR5 cells was little changed by CAMB treatment, whereas PD-L1 mRNA in ID8agg cells was significantly reduced (FIG. 39A). These data suggested the drug-mediated PD-L1 depletion mechanism can differ in human versus mouse cells or could differ due to underlying mutational differences in distinct tumors. Homeostatic PD-L1 regulation includes its degradation through ubiquitination. OVCAR5 cells were incubated with MG132, a proteasome inhibitor, which increased PD-L1 expression by 6 hours after MG132 treatment (FIG. 39B) and abolished CAMB-mediated PD-L1 reduction (FIG. 39B) suggestion ubiquitin-mediated PD-L1 degradation. To examine how CAMB influences PD-L1 degradation, a co-immunoprecipitation (Co-IP) assay was performed, showing that the amount of ubiquitinated PD-L1 was increased after CAMB treatment (FIG. 39C), suggesting that CAMB promotes PD-L1 degradation through ubiquitin-proteasome pathway.

Figure 40C:
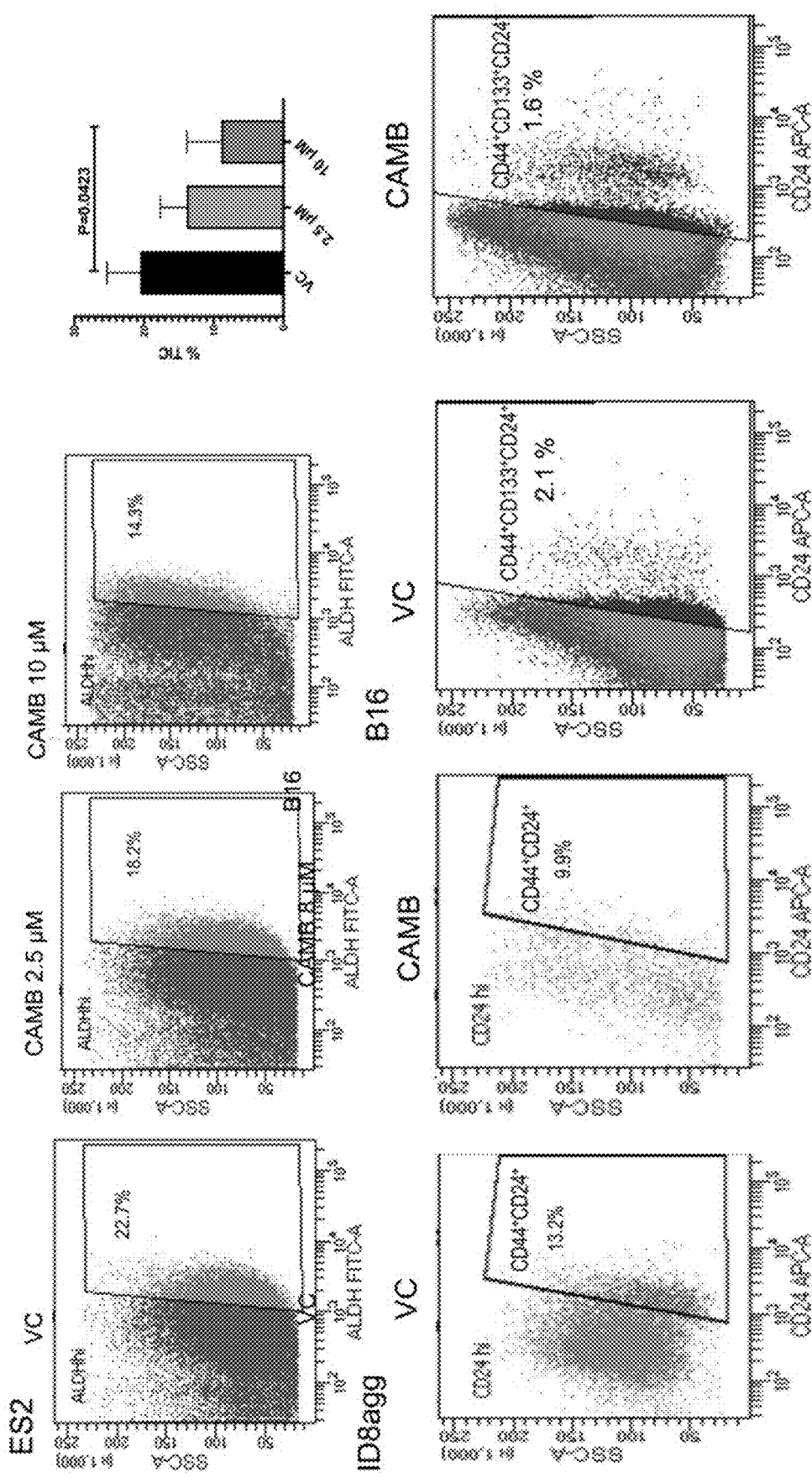

CAMB inhibits mTORC1 signaling and reduces TIC numbers in vitro: mTOR is a serine/threonine kinase regulating cellular growth and metabolism that is elevated in many cancers. mTORC1 can be increased by tumor PD-L1. Western blots showed that chlorambucil inhibits mTORC1 signaling as assessed by P70S6K$^{T389}$ phosphorylation and 4EBP1 phosphorylation. Chlorambucil reduced phosphorylation of P70S6K and 4EBP1 in a dose-dependent manner and also increased LC3 lipidation (LC3 1 and II) (FIGS. 40A-B), consistent with increased autophagic flux. These results are consistent with o data that tumor PD-L1 promotes mTORC1 and suppresses autophagy. Tumor intracellular PD-L1 can promote tumor-initiating cell (TIC) generation, asked whether chlorambucil could suppress TIC numbers. TIC expression was evaluated in ES2, ID8agg and B16 cells by flow cytometry using well-accepted TIC markers for each. Chlorambucil significantly reduced the ALDH$^{hi}$ TIC population in ES2 cells (FIG. 40C, upper panel) and CD44$^+$CD24$^+$ and CD44$^+$CD133$^+$CD24$^+$ TIC populations in B16 and ID8agg cells, respectively.

Example 14

Cephalosporins Deplete PD-L1

Figure 41:
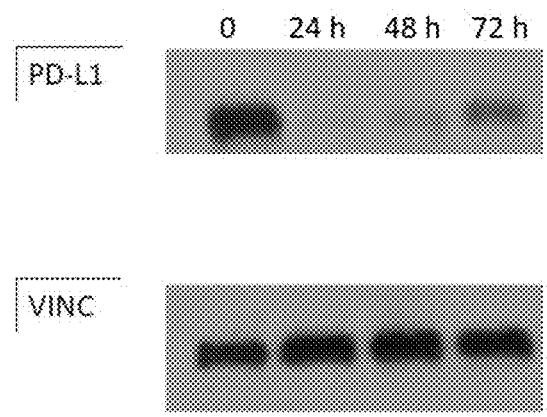
FIG. 41: Cefepime depletes PD-L1 in vitro.

Experiments were performed to see if beta-lactam antibiotics may deplete PD-L1 in cancer cells. RT4 cells were incubated at 80 μM cefepime. Cefepime was observed to deplete PD-L1 expression in vitro. Results and incubation times are shown in FIG. 41.

Figure 42:
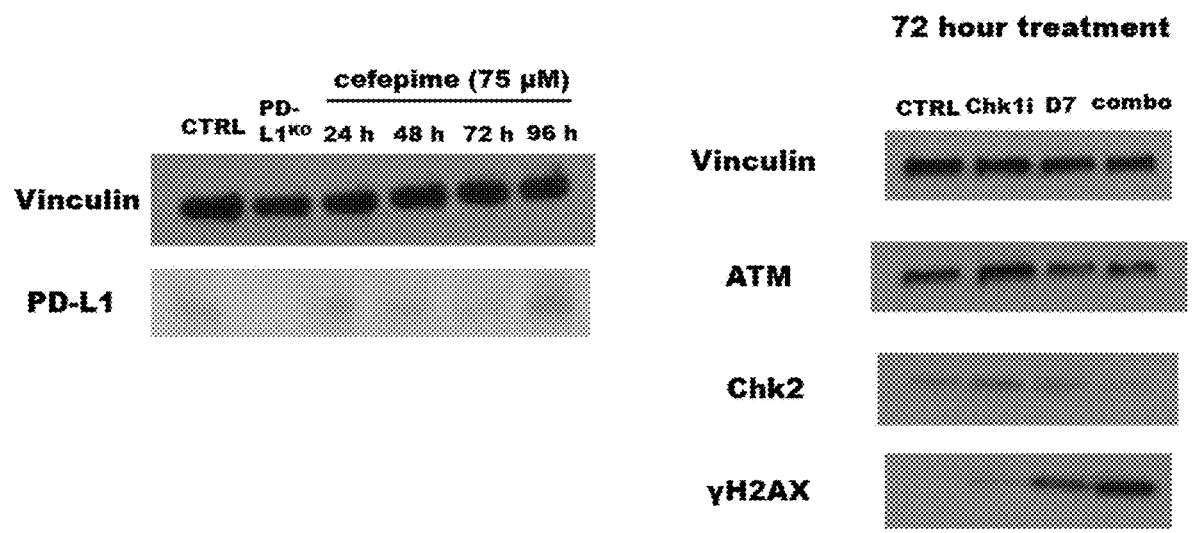
FIG. 42: Cefepime depletes Chk2 in vitro.

Next experiments were performed to see if beta-lacatam antibiotics can deplete Chk2 in vitro. RT4 cells were treated with 1 μM rabusertib (Chk1i), 75 μM cefepime (D7), or combination. Protein lysates were collected at 24, 48, 72, and 96 hours. Cefepime was observed to deplete Chk2 in vitro, and results are shown in FIG. 42.

Figure 43:
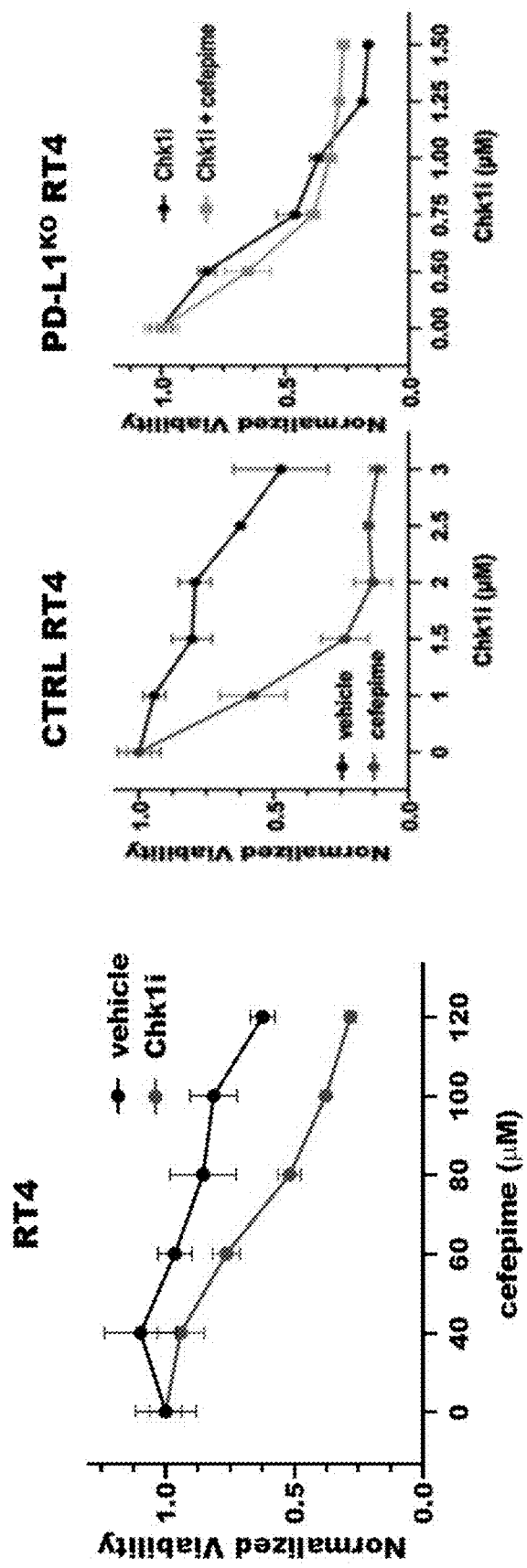
FIG. 43: Cefepime elicits Chk1 inhibitor synthetic lethality in a PD-L1-dependent manner. Chk1i=rabusertib, 1 μM.

Additional experiments were performed, as follows. MB49 were plated at 2,000 cells/well in 96 well flat bottom plates and treated with PD-L1 depleting drugs, olaparib (2.5 μM), and combination for 96 hours. RT4 were plated at 2,000 cells/well in 96 well flat bottom plates and treated with cefepime, rabusertib (1 μM), praxasertib, or combination for 96 hours. ID8agg, 4T1, and B16 cells were plated on fibronectin at 500 cells/well and treated with cefepime, rabusertib, or combination for 96 hours. Normalized treatment combination to DDR inhibitor alone, and PD-L1 depleting drug to vehicle alone (DMSO) were evaluated. Cefepime elicited Chk1 inhibitor synthetic lethality in a PD-L1-dependent manner. Results are shown in FIG. 43.

Cefepime depleted PD-L1 and Chk2 and increased DNA damage, as measured via gH2AX. Results are shown in FIGS. 44A-B.

Figure 45B:
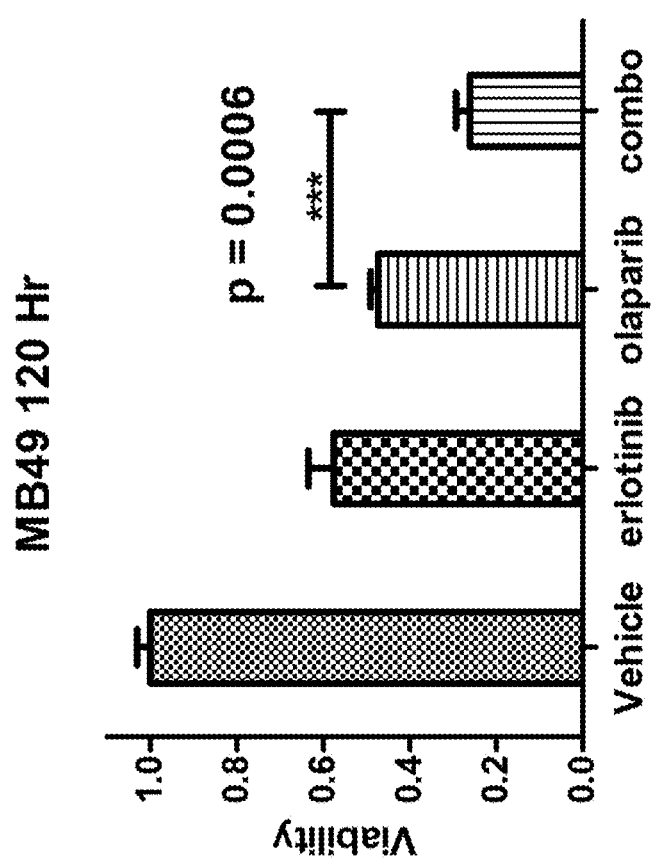

50,000 MB49 cells were plated in 6 well plates. Cells were treated with erlotinib, olaparib, combination, or vehicle the following day. Wells were harvested in triplicates and counted with cell counter. Drug and media were replenished in DMEM every 48 hours Growth curve for 5 days. Results are shown in FIGS. 45A-B.

Figure 46A:
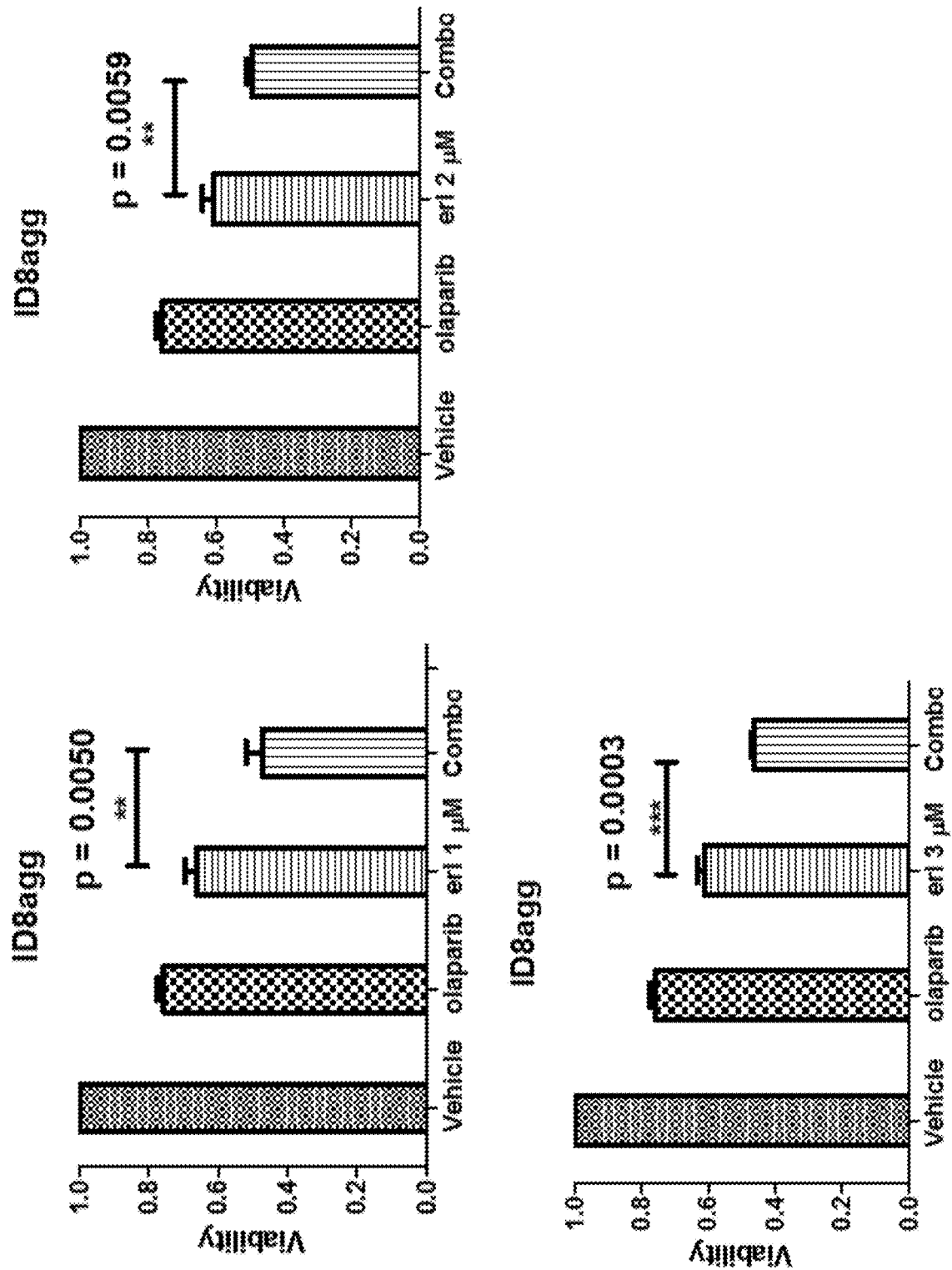
FIGS. 46A-B.
Figure 46B:
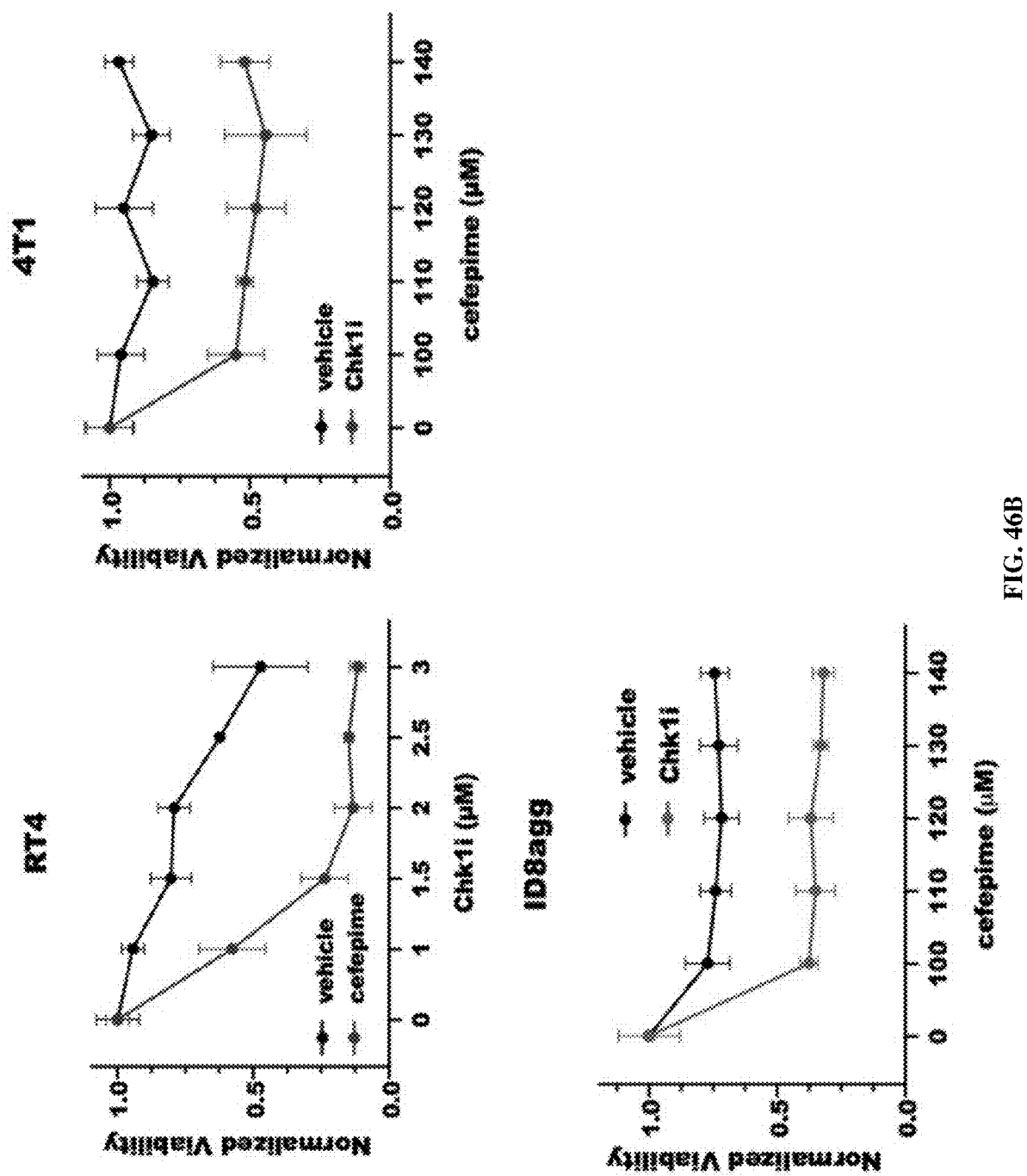

1,000 ID8agg cells were plated per well in 96 well plates. Cells were treated with 1, 2, or 3 µM of erlotinib and 5 µM or olaparib. Cells were incubated for 48 hours before read via MTT protocol Rationale for short incubation: previous western has shown that erlotinib only depletes PD-L1 for short periods of time (24 hours, but not at 48 hours). MTT cannot be easily re-drugged. Therefore, cells were plated at higher confluency and treatment time was shortened. Results are shown in FIGS. 46A-B.

Figure 47A:
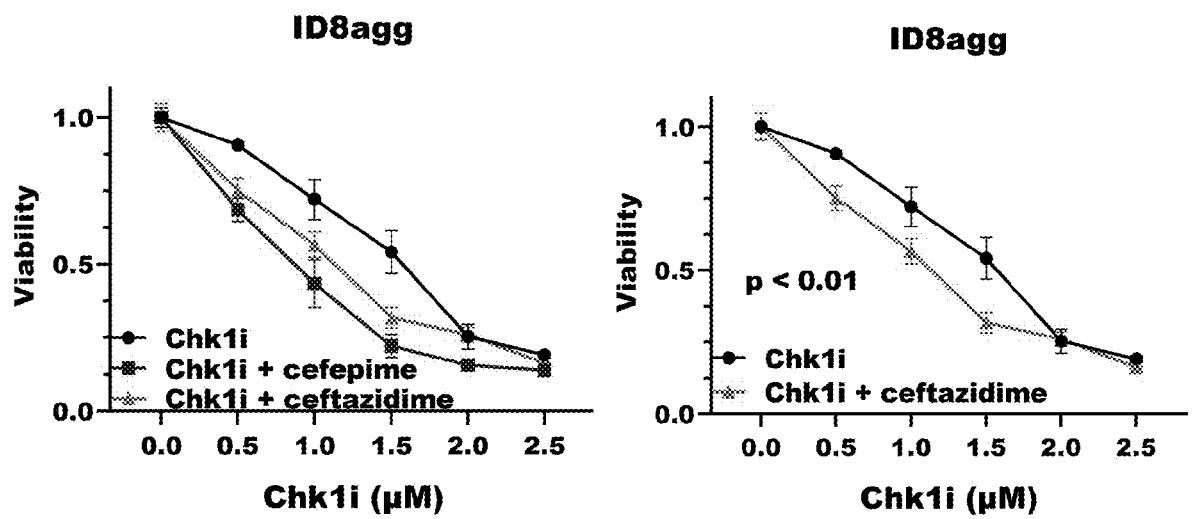
FIGS. 47A-D.
Figure 47B:
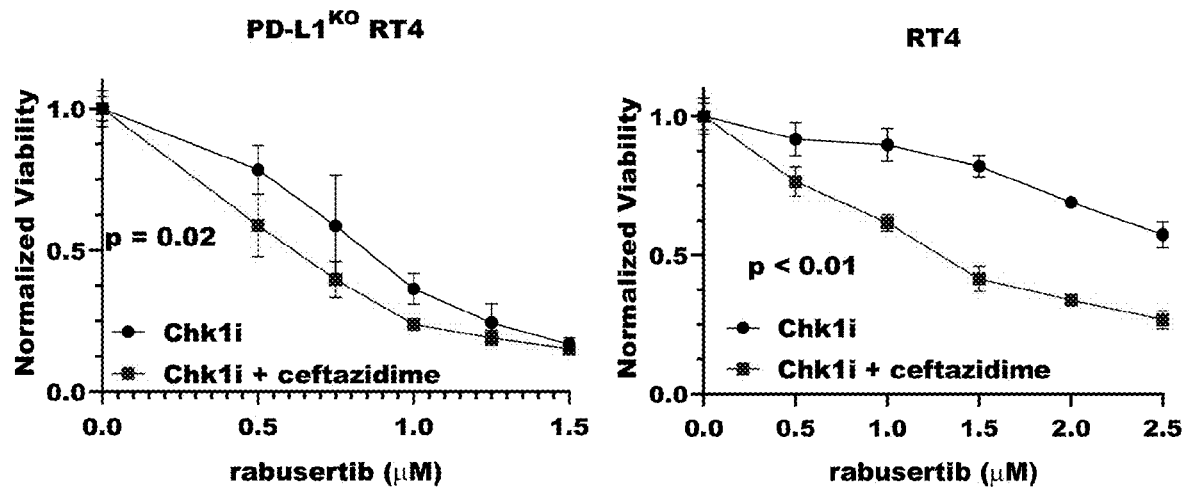
Figure 47C:
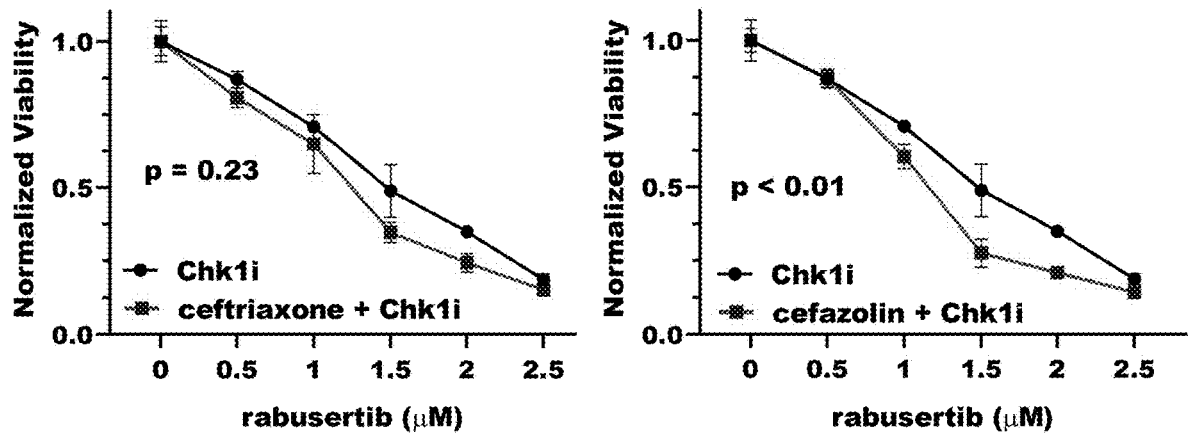
Figure 47D:
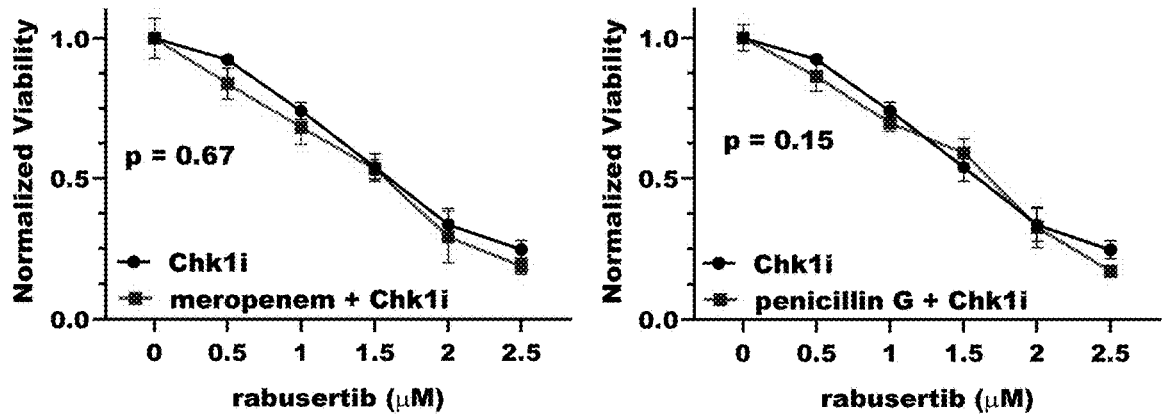

Additional experiments were performed using the cephalosporin ceftazidime. Ceftazidime was observed to induce synthetic lethality in RT4 and ID8agg cells. Results are shown in FIG. 47A. As shown in FIG. 47B, ceftazidime synthetic lethality was observed to be PD-L1 dependent. In contrast, antibiotics Penicillin G and meropenem were observed to not induce synthetic lethality with Chk1i in RT4 cells (FIG. 47D).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,636,505
U.S. Pat. No. 5,869,467
Apetoh et al., *Nature Medicine* 2007 September; 13 (9): 1050-9.
Bartek & Lukas, *Cancer Cell* 3, 421-429, 2003.
Bhattacharya et al., *Nucleic Acids Res.*, 45:4590-4605, 2017.
Burd et al., *Cancer Discov* 4, 1418-1429, 2014.
Burr et al., *Nature* 549, 101-105, 2017.
Burr et al., *Nature*, 2017.
Cao et al., Retinoic Acid-Related Orphan Receptor C Regulates Proliferation, Glycolysis, and Chemoresistance via the PD-L1/ITGB6/STAT3 Signaling Axis in Bladder Cancer. 79, 2604-2618, 2019.
Chang et al., *Cell*, 162, 1229-1241, 2015.
Chang, et al., Metabolic competition in the tumor microenvironment is a driver of cancer progression. 162, 1229-1241, 2015.
Clark et al., *American Association for Cancer Research Annual Meeting* abstract number 3696, 2017.
Clark et al., *Cancer Res* 76, 6964-6974, 2016.
Cottrell et al., *Ann Oncol* 29, 1853-1860, 2018.
Derup et al., *Cancer Res* 80:5063-75, 2020.
Ding et al., *Cell Rep.*, 25, 2972-2980, 2018.
Dong et al., B7-H1, a third member of the B7 family, co-stimulates T-cell proliferation and interleukin-10 secretion. 5, 1365-1369, 1999.
Dong et al., *Nat Med.*, 8, 793, 2002.
Escors et al., *Signal Transduct Target Ther* 3, 26, 2018.
Ewald et al., *Mol Cancer Ther* 6, 1239-1248, 2007.
Feng et al., *Oncogene*, 1-15, 2019.
Filipek et al., *J Cell Biol* 216, 4199-4215, 2017.
Fong et al., *N Engl J Med* 361, 123-134, 2009.
Fujita et al., *Mol Ther* 23, 717-727, 2015.
Gao et al., *Nat Cell Biol* 22, 1064-1075, 2020.
Gato-Canas et al., *Cell Rep* 20, 1818-1829, 2017.
Ghebeh et al., *Breast Cancer Res.*, 12, R48, 2010.
Gupta et al., *Signal Transduct Target Ther* 1, 16030, 2016.
He et al., *Acta Pharmacol Sin* 26, 462-468, 2005.
Hennessey et al., *Pigment Cell Melanoma Res* 30, 477-487, 2017a.
Hennessey et al., Ultraviolet radiation accelerates NR as-mutant melanomagenesis: A cooperative effect blocked by sunscreen. 30, 477-487, 2017b.
Ho et al., *Advances in Experimental Medicine and Biology*, vol 312. Springer, Boston, MA, 1992.
Hou et al., *Nat Cell Biol* 22, 1264-1275, 2020.
Kleffel et al., *Cell* 162, 1242-1256, 2015.
Lee and Konstantinopoulos, *Trends Cancer*, 5, 524-528, 2019.
Li et al., CHK1 Inhibitor Blocks Phosphorylation of FAM122A and Promotes Replication Stress. 80, 410-422. e416, 2020.
Lord and Ashworth, *Science*, 355:1152-1158, 2017.
Ma et al., Targeting Chk1 in p53-deficient triple-negative breast cancer is therapeutically beneficial in human-in-mouse tumor models. 122, 1541-1552. 2012.
Messing et al., *JAMA* 319, 1880-1888, 2018.
Mezzadra et al., *Nature* 549, 106-110, 2017.
Niida et al., Cooperative functions of Chk1 and Chk2 reduce tumour susceptibility in vivo. 29, 3558-3570, 2010.
O'Connor et al., *Mol Cell.*, 60, 547-560, 2015.
Otto and Sicinski, *Nat Rev Cancer*, 17:93-115, 2017.
Overbye et al., *Oncotarget* 6, 30357-30376, 2015.
Pantelidou et al., *Cancer Discov.*, 9, 722-737, 2019.
Parmar et al., The CHK1 inhibitor prexasertib exhibits monotherapy activity in high-grade serous ovarian cancer models and sensitizes to PARP inhibition. 25, 6127-6140. 2019.
Pfister et al., *Cancer Cell* 28, 557-568, 2015.
Pilié et al., *Nat Rev Clin Oncol.*, 1, 2018.
Platz et al., Human cutaneous melanoma; a review of NRAS and BRAF mutation frequencies in relation to histogenetic subclass and body site. 1, 395-405, 2008.
Qiu et al., *Biochim Biophys Acta Mol Basis Dis.*, 1864, 1754-1769, 2018.
Ribas et al., What does PD-L1 positive or negative mean? 213, 2835-2840 (2016).
Rundle et al., *Cancers* (Basel). 27; 9 (5), 2017.
Sancak et al., *Cell* 141, 290-303, 2010.
Sen et al., *Cancer Discov.*, 9, 646-661, 2019.
Sharma et al., *Cell* 168, 707-723, 2017.
Shiloh and Ziv, *Nat Rev Mol Cell Biol.*, 14:197-210, 2013.
Stolz et al., The CHK2-BRCA1 tumour suppressor pathway ensures chromosomal stability in human somatic cells. 12, 492-499, 2010.
Taube et al., *Sci Transl Med* 4, 127ra137, 2012.
Topalian et al., *Curr Opin Immunol.*, 24, 207-212, 2012.
Topalian et al., *Nat Rev Cancer* 16, 275-287, 2016.

Tu et al., *Mol Cell* 74, 1215-1226 e1214. 2019.
Tu et al., *Mol Cell.,* 2019.
von der Maase et al., *J Clin Oncol* 18, 3068-3077, 2000.
Wang et al., Inhibition of the ATM/Chk2 axis promotes cGAS/STING signaling in ARIDIA-deficient tumors. 130, 2020.
Wang et al., *Onco Targets Ther.* 9:5023-5039, 2016.
Wang et al., Tumor cell-intrinsic PD-1 receptor is a tumor suppressor and mediates resistance to PD-1 blockade therapy. 117, 6640-6650, 2020.
Witkiewicz et al., *Cell Rep* 22, 1185-1199, 2018.
Wu et al., 2016.
Wu et al., *BioRxiv,* 308601, 2018.
Wu et al., Targeting B7-H1 (PD-L1) sensitizes cancer cells to chemotherapy. *Heliyon* 4, e01039, 2018.
Zaugg et al., Cross-talk between Chk1 and Chk2 in double-mutant thymocytes. 104, 3805-3810, 2007.
Zhang et al., *Cancer Medicine,* 2021.
Zhang et al., *Journal of Immunology* 200, 166.127 (2018).
Zhang et al., *Mol Cell Biol* 24, 708-718. 2004.
Zou et al., *Sci Transl Med* 8, 328rv324, 2016.

What is claimed is:

1. A method of treating a melanoma, bladder, breast or ovarian cancer in a human subject, comprising measuring in cells of the melanoma, bladder, breast or ovarian cancer the expression of
i) cytoplasmic or intracellular PD-L1 and/or
ii) one or more Lamtor proteins; and
administering an anti-cancer therapy to the subject having the melanoma, bladder, breast or ovarian cancer, wherein the cancer expresses cytoplasmic or intracellular PD-L1 and/or one or more LAMTOR proteins at a decreased level as compared to such expression in control cells; wherein:
i) when the cancer is melanoma the control cells are B16 cells;
ii) when the cancer is bladder cancer the control cells are RT4 cells;
iii) when the cancer is breast cancer control cells are 4TI cells; and
iv) when the cancer is ovarian cancer and wherein the control cells are ES2 cells.

2. The method of claim 1, wherein the anti-cancer therapy is a DDR inhibitor D(DDRi) or an immune blockade therapy.

3. The method of claim 1, wherein the anti-cancer therapy is a DDR inhibitor (DDRi).

4. The method of claim 2, wherein the DDR inhibitor is a Chk1 inhibitor (Chk1i), a PARP inhibitor (PARPi), ATM inhibitor (ATMi), or an ATR inhibitor (ATRi).

5. The method of claim 1, wherein the PARP inhibitor is rucaprib, olaparib, or niraparib.

6. The method of claim 1, wherein the ATM inhibitor is AZD0156 or KU-55933.

7. The method of claim 1, wherein the ATR inhibitor is VE-821, AZD6738, or VX970.

8. The method of claim 4, wherein the Chk1 inhibitor is MK8776 (SCH900776), rabusertib (LY2603618), prexasertib, CCT245737, or GDC-0575.

9. The method of claim 2, wherein the immune blockade therapy is an antibody that selectively binds PD-L1 or PD-1.

10. The method of claim 9, wherein the antibody selectively binds PD-1, wherein the antibody is cemiplimab, nivolumab, pembrolizumab, spartalizumab (PDR001), camrelizumab (SHR1210), sintilimab (IBI308), tislelizumab (BGB-A317), toripalimab (JS 001), AMP-224, or AMP-514.

11. The method of claim 9, wherein the antibody selectively binds PD-L1, wherein the antibody is atezolizumab, avelumab, durvalumab, KN035, CK-301, AUNP12, CA-170, or BMS-986189.

12. The method of claim 1, wherein the anti-cancer therapy is 9-(2-phosphonylmethoxyethyl) guanine (PMEG) or chlorambucil.

13. The method of claim 12, wherein the anti-cancer therapy is 9-(2-phosphonylmethoxyethyl) guanine (PMEG).

14. The method of claim 12, wherein the anti-cancer therapy is chlorambucil.

15. The method of claim 1, wherein the anti-cancer therapy is a beta-lactam antibiotic.

16. The method of claim 15, wherein the beta-lactam antibiotic is a penam, carbapenem, an oxapenam, a penem, a carbapenem, a monobactam, a cephem, a carbacephem, or an oxacephem.

17. The method of claim 16, wherein the beta-lactam antibiotic is a cephem.

18. The method of claim 17, wherein the cephem is cefazolin, cephalexin, cephalosporin, cephalothin, cefapirin, cefaclor, cefamandole, cefuroxime, cefotetan, cefoxitin, cefixime, cefotaxime, cefpodoxime, ceftazidime, ceftriaxone, cefdinir, cefepime, cefpirome, or ceftaroline.

19. The method of claim 18, wherein the beta-lactam antibiotic is cefepime or ceftazidime.

20. The method of claim 1, wherein the method comprises administering to the mammalian subject both: (a) an antibody that selectively binds PD-L1 or PD-1, and (b) a PARP inhibitor, a Chk1 inhibitor, or chlorambucil.

21. The method of claim 20, wherein the antibody that selectively binds PD-L1 or PD-1 is cemiplimab, nivolumab, pembrolizumab, spartalizumab (PDR001), camrelizumab (SHR1210), sintilimab (IBI308), tislelizumab (BGB-A317), toripalimab (JS 001), AMP-224, AMP-514, atezolizumab, avelumab, durvalumab, KN035, CK-301, AUNP12, CA-170, or BMS-986189.

22. The method of claim 20, wherein the PARP inhibitor is rucaprib, olaparib, or niraparib.

23. The method of claim 22, wherein the PARP inhibitor is olaparib.

24. The method of claim 20, wherein the Chk1 inhibitor is MK8776 (SCH900776), rabusertib (LY2603618), prexasertib, CCT245737, or GDC-0575.

25. The method of claim 20, wherein chlorambucil is administered to the mammalian subject.

26. The method of claim 1, wherein the cancer is a breast cancer.

27. The method of claim 26, wherein the breast cancer comprises a mutation in BRCA1.

28. The method of claim 26, wherein the breast cancer does not comprise a mutation in BRCA2.

29. The method of claim 26, wherein the breast cancer does not comprise a mutation in BRCA1 or BRCA2.

30. The method of claim 1, wherein the cytoplasmic PD-L1 is located within the nucleus.

31. The method of claim 1, wherein the measuring comprises immunohistochemistry, mass spectroscopy, immunoprecipitation, flow cytometry, or digital imaging.

32. The method of claim 1, wherein the method further comprises detecting a mTORC1 signal in the cancer.

33. The method of claim 32, wherein the one or more LAMTOR protein is LAMTOR1, LAMTOR2, LAMTOR3, LAMTOR4, or LAMTOR5.

34. The method of claim 1, wherein the anti-cancer therapy is an immune checkpoint blockade therapy.

35. The method of claim 34, wherein the immune checkpoint blockade therapy is an antibody that selectively binds PD-1 or PD-L1.

36. The method of claim 1, wherein the anti-cancer therapy is a chemotherapeutic, an immunotherapy, a gene therapy, a radiotherapy, a small molecule, a DNA therapy, an RNA therapy, a cryotherapy, a cellular therapy, a toll-like receptor agonist, a dual-targeting agent, a triple-targeting agent, or a surgery.

37. The method of claim 36, wherein the anti-cancer therapy is cyclophosphamide or bevacizumab.

38. The method of claim 1, wherein the cancer is a bladder cancer, a breast cancer, or a melanoma; and wherein the DDR inhibitor is a Chk1 inhibitor (Chk1i) or a PARP inhibitor (PARPi).

39. The method of claim 1, wherein the cancer is a melanoma or an ovarian cancer; and wherein the anti-cancer therapy is pembrolizumab, bevacizumab, or cyclophosphamide.

40. The method of claim 1, wherein the method does not comprise measuring surface PD-L1 expression in the cancer.

41. The method of claim 1, wherein the method further comprises measuring surface PD-L1 expression in the cancer.

42. The method of claim 1, wherein greater than 50% of the total expressed PD-L1 in the cancer is cytoplasmic or intracellular PD-L1.

43. The method of claim 41, wherein the ratio of cytoplasmic or intracellular PD-L1:surface PD-L1 is at least 1.5, or wherein the cancer expresses at least 1.5 times more cytoplasmic or intracellular PD-L1 than surface PD-L1.

44. The method of claim 41, wherein the ratio of cytoplasmic or intracellular PD-L1:surface PD-L1 is at least 3, or wherein the cancer expresses at least 3 times more cytoplasmic or intracellular PD-L1 than surface PD-L1.

45. The method of claim 1, wherein the cancer is melanoma and wherein the control cells are B16 cells.

46. The method of claim 1, wherein the cancer is blader cancer and wherein the control cells are RT4 cells.

47. The method of claim 1, wherein the cancer is breast cancer and wherein the control cells are 4TI cells.

48. The method of claim 1, wherein the cancer is ovarian cancer and wherein the control cells are ES2 cells.

\* \* \* \* \*

UNITED STATES PATENT AND TRADEMARK OFFICE
CERTIFICATE OF CORRECTION

| | | |
|---|---|---|
| PATENT NO. | : 12,404,332 B2 | Page 1 of 1 |
| APPLICATION NO. | : 17/200729 | |
| DATED | : September 2, 2025 | |
| INVENTOR(S) | : Tyler J. Curiel and Anand Kornepati | |

It is certified that error appears in the above-identified patent and that said Letters Patent is hereby corrected as shown below:

In the Claims

Claim 1, Column 53, Line 7, 'lamtor' should be 'LAMTOR'.

Signed and Sealed this
Eleventh Day of November, 2025

John A. Squires
*Director of the United States Patent and Trademark Office*

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial sequence
<220> FEATURE:
<223> OTHER INFORMATION: Synthetic primer

<400> SEQUENCE: 1
ctctgggctt agcagtaggc                                                 20

<210> SEQ ID NO 2
<211> LENGTH: 20
<212> TYPE: DNA
<213> ORGANISM: Artificial sequence
<220> FEATURE:
<223> OTHER INFORMATION: Synthetic primer

<400> SEQUENCE: 2
gcaagctgtg gtagtcgtct                                                 20

<210> SEQ ID NO 3
<211> LENGTH: 24
<212> TYPE: DNA
<213> ORGANISM: Artificial sequence
<220> FEATURE:
<223> OTHER INFORMATION: Synthetic primer

<400> SEQUENCE: 3
acatttcatc accagcaggg tgcc                                            24

<210> SEQ ID NO 4
<211> LENGTH: 18
<212> TYPE: DNA
<213> ORGANISM: Artificial sequence
<220> FEATURE:
<223> OTHER INFORMATION: Synthetic primer

<400> SEQUENCE: 4
aacaagtggg tgctggcc                                                   18

<210> SEQ ID NO 5
<211> LENGTH: 22
<212> TYPE: DNA
<213> ORGANISM: Artificial sequence
<220> FEATURE:
<223> OTHER INFORMATION: Synthetic primer

<400> SEQUENCE: 5
gtcctccact cttttacaga cg                                              22

<210> SEQ ID NO 6
<211> LENGTH: 21
```

```
<212> TYPE: DNA
<213> ORGANISM: Artificial sequence
<220> FEATURE:
<223> OTHER INFORMATION: Synthetic primer

<400> SEQUENCE: 6
attcggttgt gaccaatggg t                                              21

<210> SEQ ID NO 7
<211> LENGTH: 23
<212> TYPE: DNA
<213> ORGANISM: Artificial sequence
<220> FEATURE:
<223> OTHER INFORMATION: Synthetic primer

<400> SEQUENCE: 7
cccctagcct atatctccct ttt                                            23

<210> SEQ ID NO 8
<211> LENGTH: 21
<212> TYPE: DNA
<213> ORGANISM: Artificial sequence
<220> FEATURE:
<223> OTHER INFORMATION: Synthetic primer

<400> SEQUENCE: 8
taccatcgtg gggataatgg c                                              21

<210> SEQ ID NO 9
<211> LENGTH: 18
<212> TYPE: DNA
<213> ORGANISM: Artificial sequence
<220> FEATURE:
<223> OTHER INFORMATION: Synthetic primer

<400> SEQUENCE: 9
aacgacccct tcattgac                                                  18

<210> SEQ ID NO 10
<211> LENGTH: 19
<212> TYPE: DNA
<213> ORGANISM: Artificial sequence
<220> FEATURE:
<223> OTHER INFORMATION: Synthetic primer

<400> SEQUENCE: 10
tccacgacat actcagcac                                                 19

<210> SEQ ID NO 11
<211> LENGTH: 20
<212> TYPE: DNA
<213> ORGANISM: Artificial sequence
<220> FEATURE:
<223> OTHER INFORMATION: Synthetic primer

<400> SEQUENCE: 11
gcttttcaat gtgaccagca                                                20

<210> SEQ ID NO 12
<211> LENGTH: 20
<212> TYPE: DNA
<213> ORGANISM: Artificial sequence
<220> FEATURE:
<223> OTHER INFORMATION: Synthetic primer

<400> SEQUENCE: 12
```

-continued atttggagga tgtgccagag                                                         20

<210> SEQ ID NO 13
<211> LENGTH: 18
<212> TYPE: DNA
<213> ORGANISM: Artificial sequence
<220> FEATURE:
<223> OTHER INFORMATION: Synthetic primer

<400> SEQUENCE: 13
ctccaaagga cttgtacg                                                           18

<210> SEQ ID NO 14
<211> LENGTH: 17
<212> TYPE: DNA
<213> ORGANISM: Artificial sequence
<220> FEATURE:
<223> OTHER INFORMATION: Synthetic primer

<400> SEQUENCE: 14
gcaagtgatt cagtttg                                                            17

<210> SEQ ID NO 15
<211> LENGTH: 17
<212> TYPE: DNA
<213> ORGANISM: Artificial sequence
<220> FEATURE:
<223> OTHER INFORMATION: Synthetic primer

<400> SEQUENCE: 15
tgctgcataa tcagcta                                                            17

<210> SEQ ID NO 16
<211> LENGTH: 17
<212> TYPE: DNA
<213> ORGANISM: Artificial sequence
<220> FEATURE:
<223> OTHER INFORMATION: Synthetic primer

<400> SEQUENCE: 16
tcccaaggac ctatatg                                                            17

<210> SEQ ID NO 17
<211> LENGTH: 17
<212> TYPE: DNA
<213> ORGANISM: Artificial sequence
<220> FEATURE:
<223> OTHER INFORMATION: Synthetic primer

<400> SEQUENCE: 17
atagtagcta cagacag                                                            17

<210> SEQ ID NO 18
<211> LENGTH: 17
<212> TYPE: DNA
<213> ORGANISM: Artificial sequence
<220> FEATURE:
<223> OTHER INFORMATION: Synthetic primer

<400> SEQUENCE: 18
cgctgcatga tcagcta                                                            17